United States Patent
Burns

(10) Patent No.: US 10,632,145 B2
(45) Date of Patent: Apr. 28, 2020

(54) BIOAVAILABLE POLYAMINES

(71) Applicant: AMINEX THERAPEUTICS INC., Newcastle, WA (US)

(72) Inventor: Mark R Burns, Bothell, WA (US)

(73) Assignee: Aminex Therapeutics, Inc., Newcastle, WA (US)

(*) Notice: Subject to any disclaimer, the term of this patent is extended or adjusted under 35 U.S.C. 154(b) by 0 days.

(21) Appl. No.: 15/753,291

(22) PCT Filed: Mar. 20, 2017

(86) PCT No.: PCT/US2017/023250
§ 371 (c)(1),
(2) Date: Feb. 17, 2018

(87) PCT Pub. No.: WO2017/165313
PCT Pub. Date: Sep. 28, 2017

(65) Prior Publication Data
US 2019/0008892 A1    Jan. 10, 2019

Related U.S. Application Data

(60) Provisional application No. 62/313,657, filed on Mar. 25, 2016.

(51) Int. Cl.
| | | |
|---|---|---|
| *A61K 31/785* | (2006.01) | |
| *A61K 9/20* | (2006.01) | |
| *A61K 9/28* | (2006.01) | |
| *A61K 45/06* | (2006.01) | |
| *A61P 35/00* | (2006.01) | |

(52) U.S. Cl.
CPC .......... *A61K 31/785* (2013.01); *A61K 9/2054* (2013.01); *A61K 9/2846* (2013.01); *A61K 9/2886* (2013.01); *A61K 45/06* (2013.01); *A61P 35/00* (2018.01)

(58) Field of Classification Search
CPC .................................................... A61K 31/785
See application file for complete search history.

(56) References Cited

U.S. PATENT DOCUMENTS

| | | |
|---|---|---|
| 6,963,010 B2 | 11/2005 | Burns et al. |
| 7,144,920 B2 | 12/2006 | Burns et al. |
| 7,160,923 B1 | 1/2007 | Vermeulin et al. |
| 7,432,302 B2 | 10/2008 | Burns et al. |
| RE43,327 E | 4/2012 | Burns et al. |
| 2006/0122279 A1 | 6/2006 | Burns et al. |
| 2011/0027172 A1 | 2/2011 | Wang et al. |
| 2011/0256161 A1 | 10/2011 | Burns et al. |

OTHER PUBLICATIONS

Berge et al., J. Pharm. Sci. 1977, vol. 66 1-18.*
International Search Report and Written Opinion dated Jun. 21, 2017, for Application No. PCT/US2017/023250.
Chen et al., "Combination therapy with 2-difluoromethylornithine and polyamine transport inhibitor against murine squamous cell carcinoma", Int. J. Cancer, 2006, vol. 118, pp. 2344-2349.
European Extended Search Report for Application No. 17770923.5 dated Oct. 15, 2019.
Maher, S. et al., "Safety and efficacy of sodium caprate in promoting oral drug absorption: from in vitro to the clinic," Advanced Drug Delivery Reviews, Elsevier, v. 61, No. 15, Dec. 17, 2009, pp. 1427-1499.

* cited by examiner

*Primary Examiner* — Ana Z Muresan
(74) *Attorney, Agent, or Firm* — BioMed IP PLLC

(57) ABSTRACT

Disclosed herein are pharmaceutical salts of a cationic protonated polyamine pharmaceutical agent and an anionic organic carboxylate which is hydrophobic when in protonated form, particularly suited for oral administration, where these salts have good bioavailability in solid dosage forms and may be used in the treatment of cancer and other medical conditions for which the pharmaceutical agent is intended.

12 Claims, 25 Drawing Sheets

DENSpm

DEHSpm

Squalamine

Deoxyspergualin

F14512

Trientine

Mozobil

Gentamicin

Polymyxin B

BIOAVAILABLE POLYAMINES

CROSS-REFERENCE TO RELATED APPLICATION

This application is a national phase application under 35 U.S.C. § 371 of International Application No. PCT/US2017/023250, filed Mar. 20, 2017, which claims the benefit under 35 U.S.C. § 119(e) of U.S. Provisional Patent Application No. 62/313,657 filed Mar. 25, 2016, where each application is incorporated herein by reference in its entirety for all purposes.

FIELD OF THE INVENTION

The present invention relates generally to pharmaceutical compositions, and more specifically to polyamines that are in a bioavailable form, and the manufacture and use thereof.

BACKGROUND

Polyamines have demonstrated many useful biological properties and are under study as active pharmaceutical agents for many medical conditions. See, e.g., Senanayake T. et al. Essay Biochem., 46:77-94 (2013); Zini M. et al. Chemico-Biological Interactions, 181:409-416 (2009); Kaur N. et al. J. Med. Chem., 51:2551-2560 (2008); Boncher, T. et al. Biochem. Soc. Trans., 35(2):356-363 (2007); Melchiorre C. et al. J. Med. Chem., 53:5906-5914 (2010); and Polyamine Drug Discovery, edited by Patrick Woster and Robert Casero, RCS Publishing, 2011, DOI:10.1039/9781849733090.

For example, certain polyamines have been identified as inhibitors of monoamine oxidase A and B (MAO A and MAO B) and vascular adhesion protein 1 (VAP-1), suggesting they may be useful in anti-neurodegenerative and anti-depressant therapies such as Parkinson's and Alzheimer's diseases, and affective disorders. See, e.g., Bonaiuto E. et al., Eur. J. Med. Chem., 70:88-101 (2013). For other reports of the neuroprotective effects of polyamines and/or their use in treating mental and neurological disorders, see, e.g., Zhang X. et al. Acta Pharmaceutica Sinica B, 5(1):67-73 (2015); Saiki R. et al. Bioorganic & Medicinal Chem. Letters, 23:3901-3904 (2013); Fiori L M et al. J. Psychiatry Neurosci., 33(2):102-110 (2008); and Gilad G M and Gilad V H, J. Pharmacology and Experimental Therapeutics, 291(1):39-43 (1999).

Cancer chemotherapy and chemoprevention is another utility for polyamine pharmaceuticals. See, e.g., Murray-Stewart T. et al. Amino Acids, 46(3):585-594 (2014); Casero R A, Cancer Discovery, 975-977 (September 2013); Minarini A. et al. European J. Medicinal Chem., 67:359-366 (2013); Casero R A and Woster P M, J. Med. Chem., 52:4551-4573 (2009); Rossi T. et al. Anticancer Research, 28:2765-2768 (2008); Seiler N. and Raul F. J. Cell. Mol. Med. 9(3):623-642 (2005).

Polyamines are also under investigation as treatment for tropical diseases. See, e.g., Verlinden B K et al. Bioorganic & Medicinal Chemistry, 23:5131-5143 (2015); and O'Sullivan M C et al. Bioorganic & Medicinal Chemistry, 23:996-1010 (2015).

The immunomodulatory effect of increased polyamine metabolism has been detailed in many scientific reports. Several studies have demonstrated an immunological inhibitory effect of increased levels of polyamines surrounding tumors. For example, Moulinoux and coworkers described experiments where a complete depletion of polyamine levels in mice grafted with 3LL (Lewis lung) carcinoma was accomplished by treatment with DFMO, a polyamine oxidase inhibitor and neomycin to prevent the gut microbial flora from providing polyamines. In these mice, tumor growth was reduced and immune system abnormalities seen in tumor-bearing animals were reversed. See, e.g., Chamaillard, L, et al. Polyamine deprivation prevents the development of tumor-induced immune suppression. British Journal of Cancer, 76:365-370 (1997). The decreased spleen cell interleukin 2 (IL-2) production and CD4+ and CD8+ lymphocyte populations observed prior to treatment with drugs were reversed and previously increased polyamine levels in the spleen were lowered. It was necessary to maintain a total blockage of all major polyamine sources to see these reversals. The T-lymphocyte population restoration did not depend upon the stage of tumor growth. No other vaccine activation or tumor-directing antigens were required.

Additionally, Moulinoux and coworkers examined the effects of more total polyamine depletion in mice grafted with 3LL carcinoma in relation to the re-stimulation of the non-specific immune system specializing in tumor cell killing. See, e.g., Chamaillard, L., et al. Polyamine deprivation stimulates natural killer cell activity in cancerous mice. Anticancer Research, 13:1027-1033 (1993). The decrease in the cytotoxic activity of the mouse's natural killer (NK) cells was reversed in these polyamine depleted animals. The authors conclude that polyamines, secreted by the tumor itself as well as absorbed through the gastrointestinal tract, can be considered not only as autocrine growth factors but also as natural immunosuppressive factors.

Soda and coworkers studied the effects of polyamines on cellular immune function. See, e.g., Kano, Y., et al. Increased blood spermine levels decrease the cytotoxic activity of lymphokine-activated killer cells: a novel mechanism of cancer evasion, Cancer Immunology, Immunotherapy, 56:771-781 (2007). Peripheral blood mononuclear cells (PBMCs) from healthy volunteers were cultured with spermine, spermidine or putrescine and the results on immune cell function were examined. Treatment resulted in decreased adhesion of non-stimulated PBMCs to tissue culture plastic in a dose- and time-dependent manner without affecting cell viability or activity. This decreased adhesion was also associated with a decrease in the number of CD11a positive and CD56 positive cells. In a group of 25 cancer patients, changes in blood spermine levels after surgery were negatively correlated with changes in lymphokine-activated killer cells (LAK) cytotoxicity. These authors concluded that increased blood spermine levels maybe an important factor in the suppression of antitumor immune cell function.

A study reported by Bowlin noted the effect of the polyamine biosynthesis inhibitor DFMO on immune system cell expression in normal and tumor-bearing (B16 melanoma) C57BL/6 mice. See, e.g., Bowlin, T. L, et al. Effect of polyamine depletion in vivo by DL-alpha-difluoromethylornithine on functionally distinct populations of tumoricidal effector cells in normal and tumor-bearing mice. Cancer Research, 46:5494-5498 (1986). They observed that DFMO treatment of these immune competent mice for 6 days reduced splenic leukocyte polyamine levels and resulted in the induction of cytotoxic T-lymphocytes in both normal and tumor-bearing animals. While putrescine and spermidine levels were significantly reduced, spermine levels were not. This led the authors to suggest that the generation of CTLs is sensitive to spermine levels.

Another study by the same authors explored the effect of treatment by each of three different ornithine decarboxylase inhibitors on tumoricidal macrophage activities in vivo. See, e.g., Bowlin, T. L, et al. Effects of three irreversible inhibitors of ornithine decarboxylase on macrophage-mediated tumoricidal activity and antitumor activity in B16F1 tumor-bearing mice. Cancer Research 50:4510-4514 (1990). Tumor-bearing mice that were treated with 0.5 to 2.0% oral DFMO had two-fold augmented macrophage mediated cytolysis of B16F1 cells ex vivo. An earlier study by Bowlin showed that polyamine oxidation down-regulates IL-2 production by human peripheral blood mononuclear cells. See, e.g., Flescher, E., et al. Polyamine oxidation down-regulates IL-2 production by human peripheral blood mononuclear cells. Journal of Immunology, 142:907-912 (1989).

Gensler reported studies exploring the ability of DFMO to prevent skin carcinogenesis and immunosuppression induced by ultraviolet irradiation in immuno-competent BALB/c mice. Gensler, H. L. Prevention by alpha-difluoromethylornithine of skin carcinogenesis and immunosuppression induced by ultraviolet irradiation. Journal of Cancer Research and Clinical Oncology 117:345-350 (1991). Mice pretreated for 3 weeks with 1% DFMO in their drinking water and then irradiated with UVB radiation had a reduced, 9% occurrence of skin cancer whereas the untreated control group developed cancers in 38% of the mice. The degree of removal of immunosuppression in the DFMO-treated mice was measured by a passive-transfer assay. Splenocytes from UV-irradiated mice when transferred to naïve mice prevented their normal ability to reject UV-induced tumor challenges (20 of 24 of mice grew tumors). When the splenocytes from UV-irradiated mice that where treated with DFMO were transferred to naïve mice, the majority of tumors were rejected (only 2 of 24 grew).

Gervais reported experiments looking at the phenotype and functional activity of dendritic cells from cancer patients and investigated the effect of putrescine on these immune cells. See, e.g., Gervais, A., et al. Dendritic cells are defective in breast cancer patients: a potential role for polyamine in this immunodeficiency. Breast Cancer Res., 7:R326-335 (2005). Cells from cancer patients yielded a lower yield of dendritic cells and these cells showed a weaker expression of MHC class II molecules. By adding putrescine to dendritic cells from normal donors, it was possible to reduce the final cytolytic activity of lymphocytes, mimicking the defective dendritic cell function of cancer patients.

Evans observed that spermine suppresses the sensitivity of cervical carcinoma cells to cytotoxic LAK lymphocytes collected from more than half the human subjects studied. See, e.g., Evans, et al. Spermine-directed immunosuppression of cervical carcinoma cell sensitivity to a majority of lymphokine-activated killer lymphocyte cytotoxicity. Nat. Immun., 14:157-163 (1995).

Tracey has reported that spermine has an immune inhibitory effect. See, e.g., Zhang, M., et al. Spermine inhibits pro-inflammatory cytokine synthesis in human mononuclear cells: a counterregulatory mechanism that restrains the immune response. J Exp. Med., 185:1759-1768 (1997). Specifically, Tracey observed that LPS stimulation of monocytes causes an increase in the uptake of spermine by the polyamine transport apparatus of the cell. They used a polyamine transport inhibitor, 4-bis(3-aminopropyl)-piperazine (BAP) to block the inhibitory activity of spermine on monocyte TNF production.

Experiments using carrageenan-induced inflammation in rats showed BAP enhanced the production of TNFα and increased the resulting edema in the foot pad. See, e.g., Zhang, M., et al. Spermine inhibition of monocyte activation and inflammation. Mol. Med., 5:595-605 (1999). See also Gervais, A., et al. Ex vivo expansion of antitumor cytotoxic lymphocytes with tumor-associated antigen-loaded dendritic cells. Anticancer Research 25, 2177-2185 (2005) and Susskind, B. M. & Chandrasekaran, J. Inhibition of cytolytic T lymphocyte maturation with ornithine, arginine, and putrescine. Journal of Immunology, 139:905-912 (1987).

Szabo and colleagues reported studies exploring the mechanism of the inhibitory effect of polyamines on the induction of nitric oxide synthase (NOS). See, e.g., Szabo, C., et al. The mechanism of the inhibitory effect of polyamines on the induction of nitric oxide synthase: role of aldehyde metabolites. Br. J. Pharmacol., 113:757-766 (1994).

The NO produced by the enzyme iNOS is a central effector molecule in the innate immune response to pathogens and is the focus of many groups working towards understanding the role of the microbe H. pylori plays in the pathogenesis of stomach ulcers and gastric cancer. Casero and Wilson observed that spermine may inhibit the production of the macrophage-derived NO coming from the inducible NO synthase (iNOS). See, e.g., Bussiere, F. I., et al. Spermine causes loss of innate immune response to Helicobacter pylori by inhibition of inducible nitric-oxide synthase translation. The Journal of Biological Chemistry 280: 2409-2412 (2005) and Chaturvedi, R., et al. Induction of polyamine oxidase 1 by Helicobacter pylori causes macrophage apoptosis by hydrogen peroxide release and mitochondrial membrane depolarization. The Journal of Biological Chemistry, 279:40161-40173 (2004).

A review article by Soda provides an overview of the immunosuppressive role played by increased polyamine metabolism. See, e.g., Soda, K. The mechanisms by which polyamines accelerate tumor spread. J. Exp. Clin. Cancer Res., 30:95 (2011). However, despite the promise of polyamine pharmaceutical agents, not all reported experiments demonstrate good clinical efficacy for these agents.

N1,N11-diethylnorspermine (DENSpm; DENSPM) was clinically evaluated for therapeutic effect against previously treated metastatic breast cancer, see e.g. Wolff, et al. Clinical Cancer Res., 9:5922-5928 (2003). In this study, DENSpm was delivered as its free base by intravenous infusions over a 15 minute period. Treatment cycles involved injections of 100 mg/m$^2$/day over 5 days every 21 days. A short plasma half-life of 0.5 to 3.7 h was observed. An additional report using DENSpm i.v. infusions for non-small cell lung cancer treatment also failed to demonstrate clinical benefits (Hahm, H. A. et al Clinical Cancer Res., 8:684-690 (2002)).

N1,N14-diethylhomospermine (DEHSpm; DEHSPM) is an additional bis-ethylated polyamine analog tested for clinical efficacy in human oncology trials. Twice daily, subcutaneous injections of this agent as its tetrahydrochloride salt at 12.5, 25 and 37.5 mg/kg in solid tumor patients showed peak drug levels at 15 to 30 minutes after injection. The drug was not observed in plasma of treated patients 2-4 hrs. post-injection (Wilding, G. et al. Investigational New Drugs, 22:131-138 (2004)). None of the 15 patients were found to have an objective response and significant toxicities at the highest dose limited further evaluation in cancer patients.

Squalamine is a chemically synthesized aminosterol, originally isolated from the liver of the dogfish shark. Studies in tumor-bearing mice have shown that squalamine acts as an inhibitor of angiogenesis and shows activity against several models of cancer in mice including lung, breast, ovarian and prostate. Clinical testing of squalamine, as its lactate salt, against advanced non-small cell lung cancer has been reported (Herbst, R. S. Clinical Cancer Res., 9:4108-4115 (2003)). Limited clinical activity was observed in this testing, where squalamine was delivered by continuous i.v. infusions over 3 h at dose levels of 100 to 400 mg/m$^2$/day. Plasma half-life of squalamine was measured to be between 1 and 2 h. An earlier report on the clinical testing of squalamine lactate salt used 120 h continuous i.v. infusion as the delivery method (Bhargava, P. et al. Clinical Cancer Res. 7:3912-3919 (2001)).

Deoxyspergualin is a synthetic analog of the bacteria derived sperqualin and has strong immunomodulatory effects on lymphocytes, macrophages and neutrophils. It is approved for treatment of steroid-resistant transplant rejection in Japan. It is delivered by subcutaneous injections at 0.5 mg/kg/day for up to 21 days. The pharmacokinetic behavior of deoxyspergualin delivery by 3 h intravenous infusions has been reported (Dhingra, K. et al Cancer Research, 55:3060-3067 (1995)) and showed a very short half-life of 1.8 h.

F14512 is a polyamine-epipodophyllotoxin conjugate that is able to target cancer cells with high polyamine transporter activity (Kruczynski, A. et al Leukemia 27:2139-2148 (2013)). It is being developed for use against AML and solid tumors and a recent publication showing its development against canine tumor showed it is delivered by i.v. injections (Tierny, D. Clinical Cancer Res., 21(23):5314-5323 (2015)). Plasma levels of F14512 in dogs treated with 0.05, 0.060, 0.070, 0.075 and 0.085 mg/kg by intravenous 3 hr. infusions increased with dose and were estimated to be within therapeutic range at approximately 2 to 3 hrs. for most dogs.

Mozobil is a bicyclam polyamine-containing drug approved for stem cell mobilization prior to hematopoeitic progenitor cell transplants during cancer chemotherapy (De Clercq, E. Pharmacology and Therapeutics, 128:509-518 (2010)). This drug is administered by subcutaneous injection. Subcutaneous delivery to healthy volunteer patients at 40, 80, 160, 240 and 360 µg/kg showed dose proportional pharmacokinetics and clearance by 10 hrs. Plasma half-life of Mozobil is 3 hrs. (Lack, N. A., et al. Clin. Pharmacol. Ther., 77:427-436 (2005)).

Trientine is a polyamine analog approved for use in Wilson's disease. This polyamine analog acts as a copper chelating agent, aiding in the elimination of excess copper associated with Wilson's disease. Although Trientine is delivered orally, as its hydrochloride salt in the clinic, its oral bioavailability is poor (8 to 30%). It has a relatively short half-life in humans (2 to 4 h). A review covering the preclinical and clinical applications of Trientine has been published. See Lu, J. Triethylenetetramine pharmacology and its clinical applications. Molecular Cancer Therapeutics, 9:2458-2467 (2010).

Methylglyoxal bis(guanylhydrazone), also known as 1,1' [methylethanediylidene]dinitrilodiguanidine and often abbreviated as MGBG, is a polyamine that functions as a competitive polyamine inhibitor of 2-adenosyl methionine decarboxylase (AMD-1), which catalyzes the synthesis of spermidine. It is described as useful in, e.g., the treatment of pain, such as inflammatory pain. See U.S. Pat. Nos. 8,258,186 and 8,609,734.

Oral delivery of spermidine has recently been shown to improve heart health and longevity of mice (Eisenburg, T. et al. Nature Medicine, 22(12):1428-1438 (2016)). Spermidine provided in the diet of mice enhanced cardiac autophagy, mitophagy and mitochondrial respiration and improved the mechano-elastical properties of cardiomyocytes in vivo. The authors attributed the spermidine extension of lifespan of mice to the autophagy inducing activities of spermidine (Eisenburg, T. et al. Autophagy, 13(4):1-3 (2017)).

Lipinski devised a set of parameters that could predict the ability of chemical substances to be orally bioavailable (Lipinski C A, et al. Adv. Drug Deliv. Rev., 46(1-3):3-26 (2001)). Known in the art as 'The Rule of 5' these parameters were based on the molecule's chemical structure and included the number of hydrogen bond donors, hydrogen bond acceptors, molecular weight and lipophilicity measurements. Many exceptions to these rules have been found and these parameters are now considered more of a guidance used to predict a molecule's oral bioavailability.

While polyamines have desirable biological properties, the inventor(s) consider that their limited oral bioavailability remains an unsolved hurdle in an effort to bring these materials to practical therapeutic use. In particular, the bioavailability of polyamines by oral administration has been a problem. Surprisingly, oral delivery of polyamine drugs as salts with hydrophobic carboxylic acids greatly improves their bio availabilities. Thus, there exists a need for a pharmaceutical composition that can deliver polyamines and protonated forms thereof to a patient in need, and which overcome one or more of the shortcoming associated with the prior art.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

The present invention relates to salts between protonated polyamine pharmaceutical agents (PPA) and deprotonated hydrophobic carboxylic acids (HCA). For example, in one embodiment the present disclosure provides a salt of a cationic protonated polyamine pharmaceutical agent and an anionic hydrophobic carboxylate, wherein (a) the anionic hydrophobic carboxylate is a carboxylate form of a hydrophobic carboxylic acid as described herein, e.g., a fatty acid selected from $C_8$-$C_{18}$ fatty acids; (b) the cationic protonated polyamine pharmaceutical agent is a protonated form of a therapeutically effective polyamine such as are described herein, for example, polyamines having from 2 to 4 amine groups that are independently protonatable in water, and optionally excluding peptides and proteins; and (c) and at least one of the protonatable amine groups of the polyamine is protonated to provide the cationic protonated polyamine pharmaceutical agent.

Optionally, the salts of the present disclosure may be characterized by one or more (two, three, four, etc.) additional features such as disclosed in embodiments herein, including one or more of the following features. The salt may have two moles of anionic hydrophobic carboxylate for each one mole of cationic protonated polyamine pharmaceutical agent, which may be named a PPA(HCA)$_2$ or PPA:(HCA)$_2$ salt. The cationic protonated polyamine pharmaceutical agent may be a protonated form of a polyamine of formula (1). The anionic hydrophobic carboxylate may be a carboxylate form of a fatty acid selected from $C_8$-$C_{14}$ fatty acids. The cationic protonated polyamine pharmaceutical agent may be a di-protonated form of a polyamine of formula AMXT 1501 and the anionic hydrophobic carboxylate is deprotonated capric acid, and the salt has two moles of deprotonated capric acid for each one mole of protonated AMXT 1501, so as to provide the dicaprate salt of AMXT 1501, optionally denoted as AMXT 1501:(caprate)$_2$. The salt may be essentially pure, e.g., it is not in admixture with more than 5 wt % of any other solid or liquid chemical. The salt may be a pharmaceutically active salt.

The present disclosure also provides, for example, methods for producing PPA-HCA salts, methods of formulating the salts into a pharmaceutical composition or a precursor thereof, solid dosage forms of these salts, methods of administrating the salts to a subject in need thereof, and other compositions that include a salt of the present disclosure as a component. For example, the present disclosure provides pharmaceutical compositions that contain a PPA:HCA salt as described herein. The pharmaceutical composition may be in a form as described herein, e.g., a solid form for oral dosage, i.e., a solid oral dosage form such as a pill or tablet.

Thus, the present disclosure provides methods for producing PPA-HCA salts. For example, in one embodiment the present disclosure provides a method comprising: combining a polyamine, a hydrophobic carboxylic acid and a solvent so as to provide a solution; and thereafter isolating a solid residue from the solution, wherein the residue comprises a PPA-HCA salt formed between the polyamine and the hydrophobic carboxylic acid. Optionally, the method may be further characterized by any one or more (e.g., any two, any three, any four) of the following: the polyamine is any of the pharmaceutically active polyamines identified herein; the hydrophobic carboxylic acid is any of the hydrophobic carboxylic acids identified herein; each of the polyamine and the hydrophobic carboxylic acid is at least 90% or at least 95% pure on a weight basis; about 1.0 mole, e.g., 0.9-1.1 moles of hydrophobic carboxylic acid are combined with each 1.0 mole of polyamine, or about 2.0 moles, e.g., 1.8-2.2 moles of hydrophobic carboxylic acid are combined with each 1.0 mole of polyamine, or about 3.0 moles, e.g., 2.7-3.3 moles of hydrophobic carboxylic acid are combined with each 1.0 mole of polyamine, or about 4.0 moles, e.g., 3.6-4.4 moles of hydrophobic carboxylic acid are combined with each 1.0 mole of polyamine; the solvent is selected from a pure polar protic solvent and a mixture of solvents comprising a polar protic solvent; the solvent comprises water, e.g., a water selected from deionized water and distilled water; the solvent comprises methanol; the polyamine and the hydrophobic carboxylic acid are added to the solvent so as to provide the solution; the method is performed in a batch process; the solvent is removed from the solution by a process selected from evaporation and distillation, so as to isolate the residue from the solution, or a co-solvent (an example being acetonitrile (ACN)) is added to the solution so as to form a supernatant and the residue in the form of a precipitate, and wherein the supernatant is separated from the residue so as to isolate the residue from the solution, or the solution is chilled so as to form a supernatant and the residue in the form of a precipitate, and wherein the supernatant is separated from the residue so as to isolate the residue from the solution; the polyamine, the hydrophobic carboxylic acid and the solvent are combined so as to provide a clear solution; the polyamine, the hydrophobic carboxylic acid and the solvent are combined at a temperature within the range of 10-30° C.; the residue comprises at least 50%, or at least 95%, or at least 99% by weight of the salt; the method further comprises combining the residue or a portion thereof with additional components so as to form a pharmaceutical composition suitable for ingestion, e.g., the method further comprises forming a solid dosage form selected from a pill, a tablet, a capsule, a lozenge, a caplet, and a pastille, from the residue or a portion thereof. Additionally, continuous flow techniques could be used for the production and isolation of the PPA:HCA salt forms described. Use of available flow apparatus, wherein solutions of the polyamine free base, in a suitable solvent such as methanol, are mixed with a co-solvent in which the salt is not soluble, such as acetonitrile, in a flow cell apparatus, allowing the continuous production of the insoluble, or soluble form of the PPA:HCA salt.

In addition, the present disclosure provides for the therapeutic use of the PPA:HCA salts. For example, the present disclosure provides a method of treating cancer comprising administering to a subject in need thereof a therapeutically effective amount of a PPA:HCA salt. Optionally, the therapeutically effective amount of the salt is administered to the subject as a solid dosage form.

In addition, the present disclosure provides PPA:HCA salts as disclosed herein for use in medicine, or for use as a medicament, or for use in manufacturing a medicament. For example, the present disclosure provides salts of the PPA AMXT 1501, where the HCA component is derived from a $C_{8-14}$ fatty acid or a $C_{10-12}$ fatty acid such as decanoic acid, also known as capric acid, for use in medicine, e.g., for use as a medicament. Furthermore, the present disclosure provides PPA:HCA salts as disclosed herein for use in the treatment of cancer. Thus, the present disclosure provides PPA:(HCA)$_1$, PPA:(HCA)$_2$ and PPA:(HCA)$_3$ salts, including salts wherein the PPA is known as AMXT 1501, and wherein the HCA component is derived from a fatty acid, e.g., $C_{8-14}$ or $C_{10-12}$ fatty acids such as capric acid, including the use of those salts in the treatment of cancer. In one embodiment, the present disclosure provides PPA:(HCA)$_2$ salts, wherein the PPA is known as AMXT 1501, and wherein the HCA component is capric acid, including the use of that salt in the treatment of cancer This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Embodiments of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings. One or more embodiments are described hereinafter with reference to the accompanying drawings in which:

FIG. 8A) or repeat once daily (Day 5; FIG. 8B) PO dosing of AMXT 1501 monotherapy of AMXT 1501 dicaprate (8, 16 and 32 mg/kg/day) to male and female beagle dogs, according to a study as described herein.

FIG. 9A) or repeat once daily (Day 5; FIG. 9B) PO dosing of 16 mg/kg/day AMXT 1501 monotherapy versus in combination with DFMO (200 mg/kg/day) to male and female beagle dogs, according to a study as described herein.

FIG. 12A shows data for Group 2 (low dose, 80 mg dose), Day 1. FIG. 12B shows data for Group 3 (mid dose, 160 mg dose), Day 1. FIG. 12C shows data for Group 4 (high dose, 320 mg dose), Day 1. FIG. 12D shows data for Group 2 (low dose, 80 mg dose), Day 28. FIG. 12E shows data for Group 3 (mid dose, 160 mg dose), Day 28. FIG. 12F shows data for Group 4 (high dose, 320 mg dose), Day 28, according to a study as described herein.

DETAILED DESCRIPTION

Figure 1:
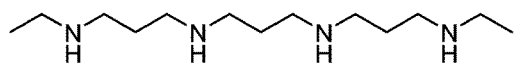
FIG. 1 shows the chemical structures of some exemplary pharmaceutically active polyamines (PPA in neutral form).
Figure 1:
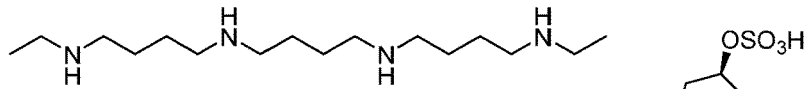
Figure 1:
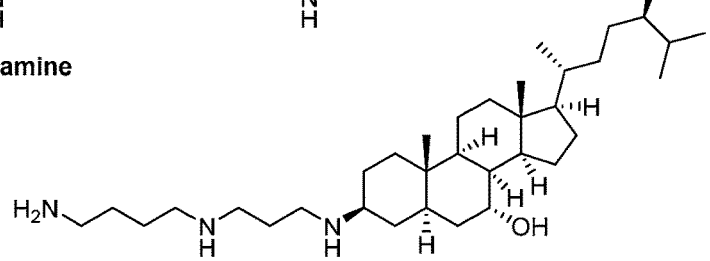
Figure 1:
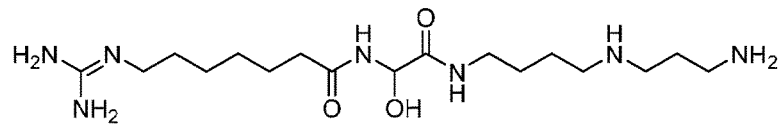
Figure 1:
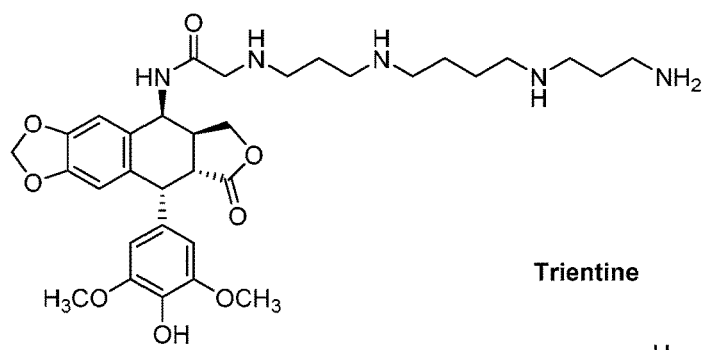
Figure 1:
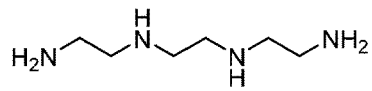
Figure 1:
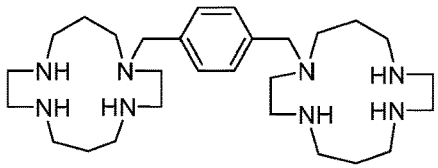
Figure 1:
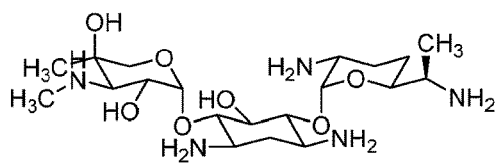
Figure 1:
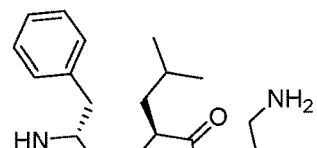
Figure 1:
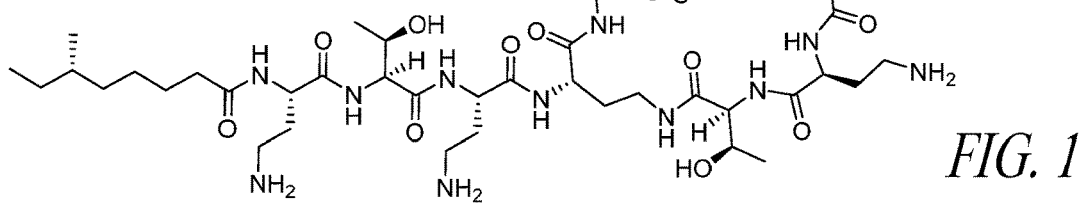

Clinical evaluation of polyamines and polyamine analogs has been hampered by delivery difficulties associated with their polycationic nature. Limitations with their oral bioavailability have resulted in their preclinical and clinical evaluation using less than desirable intravenous or intraperitoneal injection methods. These delivery methods, while sufficient for early preclinical evaluation in animal models, are unsatisfactory for eventual pharmaceutical development. Importantly, intravenous or intraperitoneal injections of polyamine analogs tend to exacerbate their toxic side-effects. High plasma concentrations of these polycationic agents lead to deleterious actions due to the agents' physical and chemical properties. Intravenous or intraperitoneal injections lead to high initial plasma concentrations followed by normal elimination. For many pharmacological targets in mammalian systems, delivery methods that lead to moderate, sustained plasma levels of drug agents are highly desirable. For this reason, oral delivery, with a delayed and sustained plasma exposure to the agent is preferred. It is also highly desirable that each patient absorb the same amount of drug based on a given dosage of drug being administered. In other words, although two patients may be administered the same dose of drug, the drug may not be equally bioavailable for the two patients, due to, e.g., differences in patient composition. A desirable component of bioavailability is that subjects receiving the same dose of a drug also achieve the same or similar plasma concentrations of the active ingredient(s) in the drug. The present disclosure recognizes and addresses these issues.

Briefly stated, in one embodiment the present disclosure relates to salts, and more particularly to salts comprising a first molecule having an ammonium group and a second molecule having a carboxylate group. The ammonium group of the first molecule is selected from the protonated forms of primary, secondary and tertiary amines, i.e., ammonium groups having 3, 2 or 1 hydrogen atom(s) attached to the nitrogen atom of the ammonium group, respectively. The first molecule may be referred to as a protonated polyamine (PPA), which denotes that it contains two or more amine groups, where each of the amine groups may be in a protonated or unprotonated form, although at least one of the amine groups is in a protonated form so as the provide the ammonium group necessary to form the salt. The first molecule is organic and biologically active, e.g., it may be an organic pharmaceutical agent or organic active pharmaceutical ingredient (API) in a formulation. The second molecule is likewise organic, and in one embodiment is a small molecule. The second molecule is hydrophobic, which means that the second molecule is formed, at least in part, from a plurality of carbon atoms bonded to hydrogen atoms, and that an uncharged form of the second molecule is not soluble in water. For convenience, the second molecule may be referred to herein as a hydrophobic carboxylic acid (HCA).

Thus, in one embodiment, the present disclosure is directed to the combination of a polyamine pharmaceutical agent and a hydrophobic carboxylic acid such as a fatty acid. In another embodiment, the present disclosure is directed to the preparation of salts of the present disclosure. In another embodiment, the present disclosure is directed to the administration of a salt formed between a polyamine pharmaceutical agent and a hydrophobic carboxylic acid, such as a fatty acid, to a subject in need thereof, to achieve a therapeutic result. In an additional embodiment, the present invention relates to the surprisingly increased bioavailability of polyamine drugs when delivered as salts associated with hydrophobic carboxylic acids. Prior to setting forth this disclosure in more detail, it may be helpful to an understanding thereof to provide definitions of certain terms to be used herein. Additional definitions are set forth throughout this disclosure. That is, the present disclosure may be understood more readily by reference to the following detailed description of preferred embodiments of the invention and the Examples included herein.

The term "salt" has its standard meaning in the art, and refers to a positively charged species (cation) and a negatively charged species (anion) that are complexed to one another through an ionic interaction. Generally, these salts do not involve covalent bonding between partner molecular components. The salt possesses different biological and pharmacological properties compared to its component cationic and anionic species delivered separately. The term salt also refers to all solvates, for example, hydrates of a parent salt compound. Salts can be obtained by customary methods known to those skilled in the art, for example, by combining a compound with an inorganic or organic acid or base in a solvent or diluent, or from other salts by cation exchange or anion exchange.

"Treatment," "treating" or "ameliorating" refers to medical management of a disease, disorder, or condition of a subject (i.e., patient), which may be therapeutic, prophylactic/preventative, or a combination treatment thereof. A treatment may improve or decrease the severity at least one symptom of a disease, delay worsening or progression of a disease, delay or prevent onset of additional associated diseases, or improve remodeling of lesions into functional (partially or fully) tissue.

A "therapeutically effective amount (or dose)" or "effective amount (or dose)" of a compound refers to that amount sufficient to result in amelioration of one or more symptoms of the disease being treated in a statistically significant manner. When referring to an individual active ingredient administered alone, a therapeutically effective dose refers to that ingredient alone. When referring to a combination, a therapeutically effective dose refers to combined amounts of the active ingredients that result in the therapeutic effect, whether administered serially or simultaneously.

"Pharmaceutically acceptable" refers to molecular entities and compositions that do not produce allergic or other serious adverse reactions when administered to a subject using routes well-known in the art. The term, "pharmaceutically acceptable" is used to specify that an object (for example a salt, dosage form, diluent or carrier) is suitable for use in patients. An example list of pharmaceutically acceptable salts can be found in the Handbook of Pharmaceutical Salts: Properties, Selection and Use, P. H. Stahl and C. G. Wermuth editors, Weinheim/Zurich:Wiley-VCHA/VHCA, 2002.

A "subject in need" refers to a subject at risk of, or suffering from, a disease, disorder or condition (e.g., cancer) that is amenable to treatment or amelioration with a compound or a composition thereof provided herein. In certain embodiments, a subject in need is a mammal, e.g., a human. The subject may be warm-blooded animal such as mice, rats, horses, cattle, sheep, dogs, cats, monkeys, etc.

As mentioned above, an embodiment of the present disclosure relates to salts that comprise positively charged first molecules and negatively charged second molecules, each as defined herein. More particularly the salt comprises a first molecule which is a protonated polyamine pharmaceutical agent (PPA), and a second molecule which is or comprises a carboxylate group attached to a hydrophobic moiety (HCA). The term PPA:HCA as used herein refers to salts that comprise protonated PPA and deprotonated HCA molecules, where the term PPA:HCA does not specify any particular stoichiometry between the PPA and HCA present in the salt, e.g., PPA:HCA refers broadly to all or any one of PPA:HCA salts having a 1:1 PPA:HCA stoichiometry (also referred to as $PPA:(HCA)_1$), and salts having a 1:2 PPA:HCA stoichiometry (also referred to as $PPA:(HCA)_2$), and also refers to salts having a 1:3 PPA:HCA stoichiometry (also referred to as $PPA:(HCA)_3$), as well as salts having a 1:4 PPA:HCA stoichiometry (also referred to as $PPA:(HCA)_4$), etc. depending on how many protonatable amine groups are present in the PPA and how many equivalents of HCA are combined with the PPA. In one embodiment, PPA:HCA as used herein refers to salts of $PPA:(HCA)_2$ stoichiometry.

The salt may comprise more than one second molecule, e.g., two negatively charged carboxylate molecules may each be complexed with a single polyamine that has two positively charged sites. The salt may comprise more than just the first and second molecules. For example, the salt may be a solvate, in which case one or more solvent molecules are complexed to the salt. Also, the salt may comprise more than one anionic species, where that additional one or more anionic species may or may not be a second molecule as defined herein. For example, the salt may comprise a first molecule complexed with both a HCA as defined herein, and a second anionic species, e.g., chloride, which is not an HCA as defined herein. For convenience, and unless otherwise specified, a protonated position of a first molecule is necessarily associated with a negatively charged HCA as defined herein. Control of the production and composition of the PPA:HCA salts also enables formation of specific polymorphs of the specified salts.

Protonated Polyamine Pharmaceutical Agent

The present disclosure provides salts that may be used to deliver molecules to a subject, where after their administration the salts may undergo some change(s) in form, and it is this changed form that actually exerts the desired biological effect. For example, the first molecule may be a pharmaceutically active compound in at least one of a protonated or non-protonated form. In other words, although the first molecule is necessarily protonated in the salts of the present disclosure which are administered to the subject, the biologically active form of the first molecule may or may not have the same amount of protonation as is present in the salt. As another example, the first molecule may be a pro-drug for the biologically active drug. Thus, the first molecule may undergo some changes in vivo, after administration, to generate the desired biologically active form. The first molecule will be referred to herein as being pharmaceutically active, with the understanding that the desired biologically active form of the first molecule may not arise until after the salt formed from the first molecule is administered to a subject.

The first molecule may be a small molecule, which means it has a molecular weight of less than 10,000 g/mol, or in alternative embodiments, of less than 9,000, or less than 8,000, or less than 7,000, or less than 6,000, or less than 5,000, or less than 4,000, or less than 3,000, or less than 2,000, or less than 1,000 g/mol. Optionally, the first molecule excludes one or more of a peptide, polypeptide, poly(amino acid) and protein.

The first molecule comprises two or more ammonium groups, where an ammonium group of the first molecule is selected from the protonated forms of primary, secondary and tertiary amines, i.e., ammonium groups having 3, 2 or 1 hydrogen atom(s) attached to the nitrogen atom of the ammonium group, respectively. The first molecule may be referred to as a protonated polyamine (PPA), which denotes that it contains two or more amine groups, where each of the amine groups may be in a protonated or unprotonated form, although at least one of the amine groups is in a protonated form so as the provide the ammonium group necessary to form a salt complex with a HCA as disclosed herein. In one embodiment, the polyamine comprises amine groups having a pKa/b of 6 to 13. Methods to determine pKa values of the natural, and synthetic polyamines have been described (Blagbrough, I. S.; Mewally, A. A.; Geall, A J. Measurement of polyamine pKa values. Methods Mol. Biol. 2011, 720, 493-503). The influence of protonation of the first amino group in a polyamine towards the pKa of the second amino group is well established in the scientific field. Each protonated amine group thus lowers the pKa of the second amino group. Therefore, formation of salts with monocarboxylic acids may involve protonation of multiple amino groups of the polyamine, even amino groups whose pKa values may be below 7.

In one embodiment, the first molecule has exactly two amine groups, where one or optionally both are in a protonated form. In one embodiment, the first molecule has exactly three amine groups, where one, or optionally two or all three are in a protonated form. In one embodiment, the first molecule has exactly four amine groups, where one, or optionally two or three or all four are in a protonated form.

The first molecule is an organic molecule, meaning that it comprises carbons and hydrogens. The first molecule may be a so-called small molecule, which means that it has a molecular weight of less than 2,000 g/mol, or in alternative embodiments, of less than 1,500, or less than 1,000, or less than 900, or less than 800, or less than 700, or less than 600, or less than, or less than 500 g/mol. Optionally, the first molecule is not a protein or polypeptide, and/or is not a polynucleotide.

In one embodiment, the PPA is a protonated form of a polyamine having the formula (I)

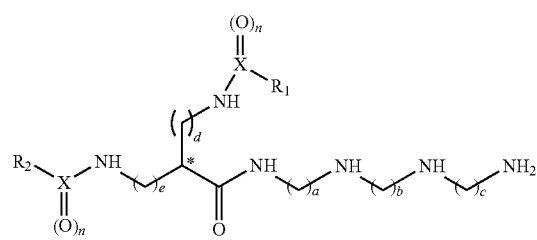

(I)

wherein
a, b, and c independently range from 1 to 10;
d and e independently range from 0 to 30;
each X is independently either a carbon (C) or sulfur (S) atom;
$R_1$ and $R_2$ are independently selected from H or from the group of
a straight or branched $C_{1-50}$ saturated or unsaturated aliphatic, carboxyalkyl, carbalkoxyalkyl, or alkoxy;
a $C_{1-8}$ alicyclic;
a single or multiring aryl substituted or unsubstituted aliphatic;
an aliphatic-substituted or unsubstituted single or multiring aromatic;
a single or multiring heterocyclic;
a single or multiring heterocyclic aliphatic;
a $C_{1-10}$ alkyl;
an aryl sulfonyl;
or cyano; or
$R_2X(O)_n—$ is replaced by H;
wherein * denotes a chiral carbon position; and
wherein if X is C then n is 1; if X is S then n is 2; and if X is C then the XO group may be $CH_2$ such that n is 0. Any one or more of the NH or $NH_2$ groups may be protonated so as to provide a protonated form of the polyamine, with the exception of NH groups adjacent to a carbonyl group, i.e., NH groups that form part of an amide group, since such NH groups are not readily protonated.

In another embodiment, the PPA is a protonated form of a polyamine having the formula (II)

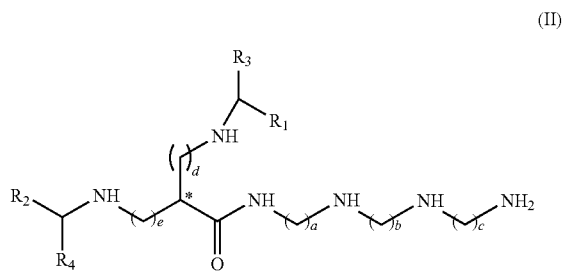

(II)

wherein
a, b, and c independently range from 1 to 10 and d and e independently range from 0 to 30;
$R_1$ and $R_3$ may be the same or different and are independently selected from H or from the group of a straight or branched $C_{1-50}$ saturated or unsaturated aliphatic, carboxyalkyl, carbalkoxyalkyl, or alkoxy; a $C_{1-8}$ alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a $C_{1-10}$ alkyl; an aryl sulfonyl; or cyano; and $R_2$ and $R_4$ may be the same or different and are independently selected from the group of a straight or branched $C_{1-50}$ saturated or unsaturated aliphatic, carboxyalkyl, carbalkoxyalkyl, or alkoxy; a $C_{1-8}$ alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a C1-10 alkyl; an aryl sulfonyl; or cyano. Any one or more of the NH or $NH_2$ groups may be protonated so as to provide a protonated form of the polyamine, with the exception of NH groups that are not basic, such as NH groups adjacent to a carbonyl group, i.e., NH groups that form part of an amide group, since such NH groups are not readily protonated.

In another embodiment, the PPA is a protonated form of a polyamine having the formula (III):

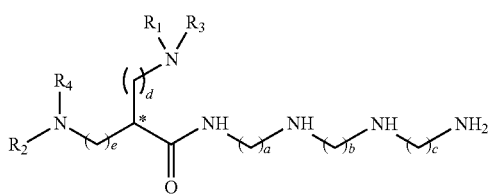

(III)

wherein a, b, and c independently range from 1 to 10 and d and e independently range from 0 to 30;

$R_1$ and $R_3$ may be the same or different and are independently selected from H or from the group of a straight or branched $C_{1-50}$ saturated or unsaturated aliphatic, carboxyalkyl, carbalkoxyalkyl, or alkoxy; a $C_{1-8}$ alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a C1-10 alkyl; an aryl sulfonyl; or cyano; and $R_2$ and $R_4$ may be the same or different and are independently selected from the group of a straight or branched $C_{1-50}$ saturated or unsaturated aliphatic, carboxyalkyl, carbalkoxyalkyl, or alkoxy; a $C_{1-8}$ alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a $C_{1-10}$ alkyl; an aryl sulfonyl; or cyano. Any one or more of the NH or $NH_2$ groups may be protonated so as to provide a protonated form of the polyamine, with the exception of NH groups that are not basic, such as NH groups adjacent to a carbonyl group, i.e., NH groups that form part of an amide group, since such NH groups are not readily protonated.

In another embodiment, the PPA is a protonated form of a polyamine having the formula (IV)

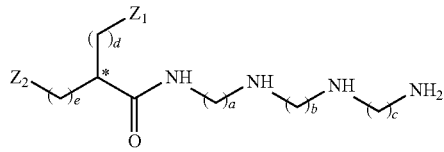

(IV)

wherein a, b, and c independently range from 1 to 10 and d and e independently range from 0 to 30;

$Z_1$ is $NR_1R_3$ and $Z_2$ is selected from —$R_1$, —$CHR_1R_2$ or —$CR_1R_2R_3$ or $Z_2$ is $NR_1R_3$ and $Z_1$ is selected from —$R_1$, —$CHR_1R_2$ or —$CR_1R_2R_3$, wherein $R_1$ and $R_2$ may be the same or different and are independently selected from H or from the group of a straight or branched $C_{1-50}$ saturated or unsaturated aliphatic, carboxyalkyl, carbalkoxyalkyl, or alkoxy; a $C_{1-8}$ alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a $C_{1-10}$ alkyl; an aryl sulfonyl; or cyano; and $R_3$ is selected from the group of a straight or branched $C_{1-50}$ saturated or unsaturated aliphatic, carboxyalkyl, carbalkoxyalkyl, or alkoxy; a $C_{1-8}$ alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a $C_{1-10}$ alkyl; an aryl sulfonyl; or cyano. Any one or more of the NH or $NH_2$ groups may be protonated so as to provide a protonated form of the polyamine, with the exception of NH groups that are not basic, such as NH groups adjacent to a carbonyl group, i.e., NH groups that form part of an amide group, since such NH groups are not readily protonated In another embodiment, the PPA is a protonated form of a polyamine having the formula (1501), where any one or more of the NH or $NH_2$ groups may be protonated so as to provide a protonated form of the PPA, with the exception of NH groups that are not basic, such as NH groups adjacent to a carbonyl group, i.e., NH groups that form part of an amide group, since such NH groups are not readily protonated.

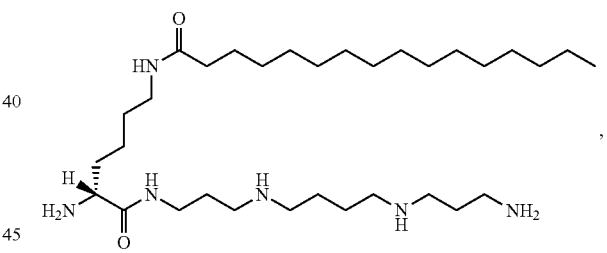

(1501)

where an exemplary salt is formed from components having the structures

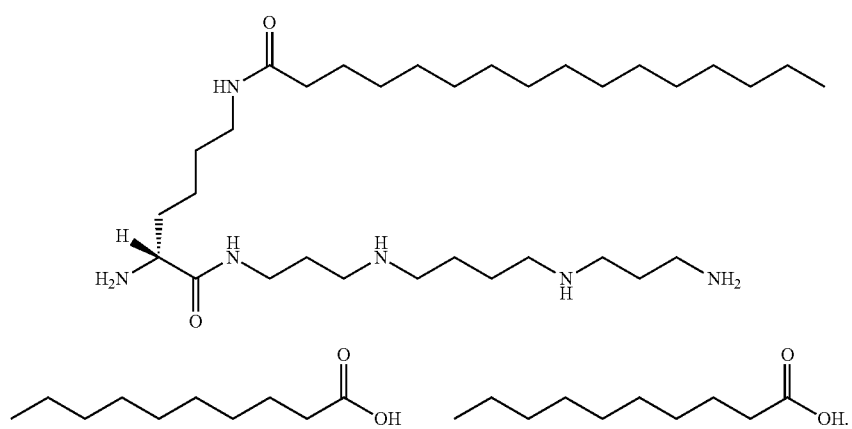

In another embodiment, the PPA is a protonated form of a polyamine having the formula (1505), where any one or more of the NH or NH$_2$ groups may be protonated so as to provide a protonated form of the polyamine, with the exception of NH groups that are not basic, such as NH groups adjacent to a carbonyl group, i.e., NH groups that form part of an amide group, since such NH groups are not readily protonated.

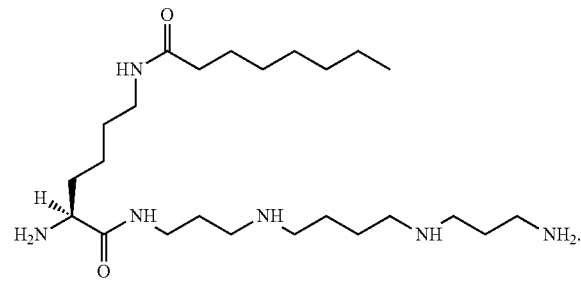

(1505)

In another embodiment, the PPA is a protonated form of a polyamine having the formula (2030), where any one or more of the NH or NH$_2$ groups may be protonated so as to provide a protonated form of the polyamine, with the exception of NH groups that are not basic, such as NH groups adjacent to a carbonyl group, i.e., NH groups that form part of an amide group, since such NH groups are not readily protonated.

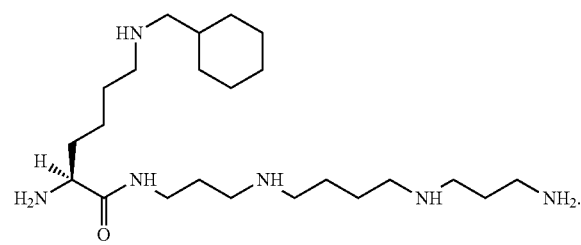

(2030)

In another embodiment, the PPA is a protonated form of a polyamine having the formula (1569), where any one or more of the NH or NH$_2$ groups may be protonated so as to provide a protonated form of the polyamine, with the exception of NH groups that are not basic, such as NH groups adjacent to a carbonyl group, i.e., NH groups that form part of an amide group, since such NH groups are not readily protonated.

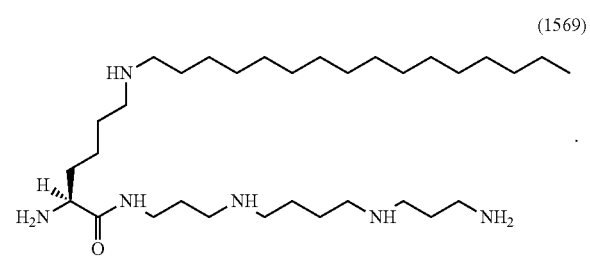 [SMILES: CCCCCCCCCCCCCCCCNCCCC[C@H](N)C(=O)NCCCNCCCCNCCCN]

(1569)

In one embodiment, the PPA is a protonated form of a polyamine having the formula (1426), where any one or more of the NH or NH$_2$ groups may be protonated so as to provide a protonated form of the polyamine, with the exception of NH groups that are not basic, such as NH groups adjacent to a carbonyl group, i.e., NH groups that form part of an amide group, since such NH groups are not readily protonated

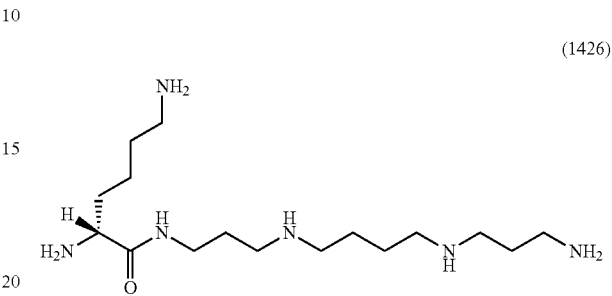

(1426)

Any one or more, e.g., any two, three, four, five, etc. of the polyamines of formulae (I)-(IV), 1426, 1501, 1505, 1569, 2030, DENSpm, DEHSpm, Squalamine, Deoxyspergualin, F14512, Mozobil, Trientine, Gentamicin, Polymyxin B, spermidine, and 1,1'[methylethanediylidene]dinitrilo-diguanidine which is also known as methylglyoxal bis (guanylhydrazone) or MGBG, are exemplary polyamines which in protonated form may be a protonated polyamine pharmaceutical agent of the present disclosure. Other molecules having a plurality of amine groups and suitable biological activity may also be used to provide a PPA of the present disclosure.

Hydrophobic Carboxylic Acid

As mentioned herein, in one embodiment the present disclosure relates to salts of cationic protonated polyamines in combination with anionic molecules comprising a carboxylate group attached to a hydrophobic moiety. These anionic species will be referred to herein for convenience as hydrophobic carboxylic acids (HCAs).

In one embodiment, whether a particular carboxylate-containing molecule is a HCA depends on the water solubility of the corresponding carboxylic acid compound. In other words, whether a carboxylate compound of the formula R—C(=O)O$^-$ is a HCA depends on the water solubility of the corresponding carboxylic acid compound of the formula R—C(=O)OH. In various embodiments, an HCA of the present disclosure is the carboxylate form of a corresponding carboxylic acid where the carboxylic acid-containing compound has a water solubility of less than 10 g/L, or less than 1 g/L, or less than 0.1 g/L, or less than 0.01 g/L in water, as determined at a temperature of 25° C. and a pH of 7. Compendiums of the water solubility of carboxylic acid-containing compounds may be found in, e.g., Yalkowsky S H, Dannenfelser R M; The AQUASOL database of Aqueous Solubility. Fifth ed., Tucson, Ariz.: Univ. AZ, College of Pharmacy (1992); Yalkowsky S H et al; Arizona Data Base of Water Solubility (1989); and The Handbook of Aqueous Solubility Data, Second Edition, edited by Yalkowsky S H, He, Y, and Jain, P, CRC Press (2010).

In one embodiment, the HCA of formula R—C(=O)O$^-$ is characterized in terms of the number of carbon atoms which forms the R group. For example, in various embodiments, the R group has at least 6 carbon atoms, or at least 7 carbon atoms, or at least 8 carbon atoms, or at least 9 carbon atoms, or at least 10 carbon atoms, or at least 11 carbon atoms, or at least 12 carbon atoms, or at least 13 carbon atoms, or at least 14 carbon atoms, or at least 15 carbon atoms, or at least 16 carbon atoms. In addition, or alternatively, the R group may be characterized by a maximum number of carbon atoms present in the moiety. For example, in various embodiments the R group has no more than 24 carbon atoms, or no more than 23 carbon atoms, or no more than 22 carbon atoms, or no more than 21 carbon atoms, or no more than 20 carbon atoms, or no more than 19 carbon atoms, or no more than 18 carbon atoms, or no more than 17 carbon atoms, or no more than 16 carbon atoms, or no more than 15 carbon atoms, or no more than 14 carbon atoms, or no more than 13 carbon atoms, or no more than 12 carbon atoms, or no more than 11 carbon atoms, or no more than 10 carbon atoms.

When the HCA is characterized in terms of the number of carbon atoms which forms the R group, the characterization may take the form of a range of carbon atoms. For example, the R group may be a $C_8$-$C_{16}$ R group, which refers to an R group having at least 8 carbon atoms and not more than 16 carbon atoms. In additional embodiments, the R group is a $C_8$-$C_{14}$ R group, or a $C_8$-$C_{12}$ R group, or a $C_8$-$C_{10}$ R group, or a $C_{10}$-$C_{12}$ R group, or a $C_{10}$-$C_{14}$ R group, or a $C_{10}$-$C_{16}$ R group, or a $C_{10}$-$C_{18}$ R group. The range of carbon atoms may be selected from any two values between 8 and 24, where optionally odd numbers are selected. In one embodiment, the R group is formed solely from carbon and hydrogen atoms, where such an R group may be referred to as a hydrocarbon group, and HCAs having a hydrocarbon R group may be referred to as fatty acid HCAs.

In addition to specifying the number of carbon atoms in the R group, the R group may be characterized in terms of its structure. In one embodiment, the R group is aliphatic as opposed to aromatic. In one embodiment, the R group is a straight chain hydrocarbon, i.e., contains no branches. In another embodiment, the R group is a branched chain hydrocarbon, i.e., contains at least one branch, which refers to a carbon being bonded to 3 or 4 other carbons. In another embodiment, the R group includes a cyclic component such as cyclohexyl, which may be present either as a substituent on the chain, or embedded within the chain to provide a structure such as $C_1$-$C_6$ hydrocarbon chain—cyclohexyl radical—$C_1$-$C_6$ hydrocarbon chain—C(=O)O—. In another embodiment, the hydrocarbon chain is saturated, i.e., does not contain any double or triple or aromatic bonds. In another embodiment, the hydrocarbon chain is unsaturated. In another embodiment, the hydrocarbon group is aliphatic rather than including an aromatic portion.

Fatty acids of formula R—COOH are a convenient precursor to the HCA component of formula R—COO⁻ of the salts of the present disclosure. Optionally, the HCA is derived from a fatty acid, where the fatty acid is pharmaceutical grade fatty acid. Suitable fatty acids are available from many commercial suppliers. For example, Sigma-Aldrich (St. Louis, Mich., USA) or Spectrum Chemical (New Brunswick, N.J., USA) provides suitable fatty acids.

For example, in one embodiment, the HCA is the corresponding carboxylate form of a fatty acid compound, such as a $C_8$-$C_{16}$ straight chain hydrocarbon fatty acid. Exemplary fatty acids of this type include octanoic acid (also known as caprylic acid), nonanoic acid, decanoic acid (also known as capric acid), undecanoic acid, dodecanoic acid (also known as lauric acid), tridecanoic acid, tetradecanoic acid and hexadecanoic acid. In one embodiment, the fatty acid is octanoic acid. In another embodiment, the fatty acid is nonanoic acid. In another embodiment, the fatty acid is decanoic acid. In another embodiment the fatty acid is undecanoic acid. In another embodiment, the fatty acid is dodecanoic acid. In another embodiment, the fatty acid is tridecanoic acid. In another embodiment, the fatty acid is tetradecanoic acid. In another embodiment, the fatty acid is hexadacanoic acid.

As another example, in one embodiment, the HCA is the corresponding carboxylate form of a hydrocarbon group attached to a carboxylic acid group, where the hydrocarbon group may be, for example an aliphatic hydrocarbon group having 8-18, or 10-16 carbon atoms. Such hydrocarbon groups may be straight chain to provide fatty acids such as octanoic acid, decanoic acid, dodecanoic acid, tetradecanoic acid etc. as described above. Alternatively, such hydrocarbon groups may contain one or more branches in the carbon chain.

The HCA may or may not be a pharmaceutically active agent, although in one embodiment the HCA is not a pharmaceutically active agent. Optionally, the HCA is not a polypeptide or protein, and optionally neither of the PPA or the HCA is a polypeptide or protein. Optionally, the HCA is not a polynucleotide, and optionally neither of the PPA or the HCA is a polynucleotide.

In one embodiment the HCA is pure. In other words, the HCA constitutes greater than 90 wt. %, or greater than 95 wt. %, or greater than 96 wt. %, or greater than 97 wt. %, or greater than 98 wt. %, or greater than 99 wt. % of the carboxylate-containing compounds present in the salt molecule.

While the HCA may be the carboxylate form of a fatty acid, the HCA is not necessarily the carboxylate form of a fatty acid. Other carboxylic acid-containing compounds of formula R—COOH which may give rise to a HCA of formula R—C(=O)O— include cholic acid. In additional embodiments, organic carboxylic acids of polyethylene glycol functionality may be used, i.e., the R group of R—COOH may include the $(CH_2-CH_2-O)_n$ group where n is 1-20. In one embodiment, the HCA may contain more than one carboxylate group, e.g., it may be a dicarboxylate or tricarboxylate HCA, where examples include oxalic and citric acids. In one embodiment, the salts of the present disclosure are formed between a protonated polyamine and a lipid sulfonate formed from a lipid sulfonic acid.

Combination of Polyamine and Carboxylic Acid

As mentioned herein, in one embodiment the present invention provides salts of cationic protonated polyamines and anionic hydrophobic carboxylates. The salts may optionally be denoted by the term (polyamine mH⁺) (R—COO⁻)$_m$ where m is 1 when the salt is a monocarboxylate salt, m is 2 when the salt is a dicarboxylate salt, m is 3 when the salt is a tricarboxylate salt, m is 4 when the salt is a tetracarboxylate salt, etc. The R group is selected to that the compound of formula R—COOH is hydrophobic (lipophilic), i.e., not very water soluble and may optionally be described as water insoluble, where exemplary R groups have about 9 carbons (e.g., capric acid) up to about 23 carbons (e.g., cholic acid). The polyamine will be in protonated form where, in general, the more basic amine groups will be protonated first, where tertiary amine groups are generally more basic than secondary amine groups, and secondary amine groups are generally more basic than primary amine groups.

The composition of the salts of the present disclosure will depend, in large part, on the specific components used to prepare the salt, and the relative amounts of the components that are used to prepare the salt. In general, when preparing the salts, the polyamine component may be provided as the neutral free base form or as a charged salt form which includes a counterion, and more specifically an anion. Likewise, the carboxylate component may be provided as the neutral free carboxylic acid form or as a charged salt form which includes a counterion, and more specifically a cation. The charged salt form of the polyamine may be referred to as an acid addition salt of the polyamine, while the charged salt form of the hydrophobic carboxylate may be referred to as the base addition salt of the carboxylic acid. These salts may be prepared by methods as disclosed herein. A therapeutically acceptable salt of the present disclosure comprises a polyamine pharmaceutical agent in cationic (protonated) form and a pharmaceutically acceptable hydrophobic carboxylic acid species in anionic (deprotonated) form, such as disclosed herein.

For example, in one embodiment the present disclosure provides a salt formed between an organic cationic species and an organic anionic species. The cationic species is a protonated polyamine pharmaceutical agent, which refers to a pharmaceutical agent that has at least one amine group in a protonated form. The anionic species is a deprotonated carboxylic acid, which refers to a carboxylic acid that has transferred its acid proton to the polyamine pharmaceutical agent, thereby providing a protonated pharmaceutical agent and a deprotonated carboxylic acid. The salt may optionally be in a solid dosage form, suitable for administration to a patient in a therapeutic method. Optionally, the anionic hydrophobic carboxylate is a carboxylate form of a fatty acid selected from $C_8$-$C_{18}$ fatty acids; the cationic protonated polyamine pharmaceutical agent is a protonated form of a therapeutically effective polyamine, where the polyamine does not include peptides or proteins; and/or the cationic protonated polyamine pharmaceutical agent has from 2 to 4 amine groups that are independently protonatable in water, and at least one of those protonatable amine groups is protonated to provide the cationic protonated polyamine pharmaceutical agent. The salt may be further described by one or more of the following: the salt has two moles of anionic hydrophobic carboxylate for each one mole of the cationic protonated polyamine pharmaceutical agent; the cationic protonated polyamine pharmaceutical agent is a protonated form of a polyamine of Formula (1) and the anionic hydrophobic carboxylate is a carboxylate form of a fatty acid selected from $C_8$-$C_{14}$ fatty acids,

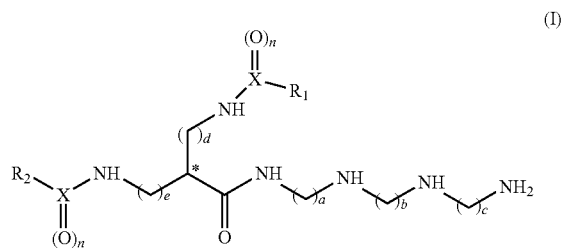

wherein, a, b, and c independently range from 1 to 10; d and e independently range from 0 to 30; each X is independently either a carbon (C) or sulfur (S) atom; $R_1$ and $R_2$ are independently selected from H or from the group of (i) a straight or branched $C_{1-50}$ saturated or unsaturated aliphatic, carboxyalkyl, carbalkoxyalkyl, or alkoxy; (ii) a $C_{1-8}$ alicyclic; (iii) a single or multiring aryl substituted or unsubstituted aliphatic; (iv) an aliphatic-substituted or unsubstituted single or multiring aromatic; (v) a single or multiring heterocyclic; (vi) a single or multiring heterocyclic aliphatic; (vii) a C1-10 alkyl; (viii) an aryl sulfonyl; (ix) or cyano; or (x) R2X(O)n- is replaced by H; wherein * denotes a chiral carbon position; and wherein if X is C then n is 1; if X is S then n is 2; and if X is C then the XO group may be CH2 such that n is 0; optionally, the cationic protonated polyamine pharmaceutical agent is a di-protonated form of a polyamine of formula AMXT 1501 and the anionic hydrophobic carboxylate is deprotonated capric acid, and the salt has two moles of deprotonated capric acid for each one mole of protonated AMXT 1501 having the formula

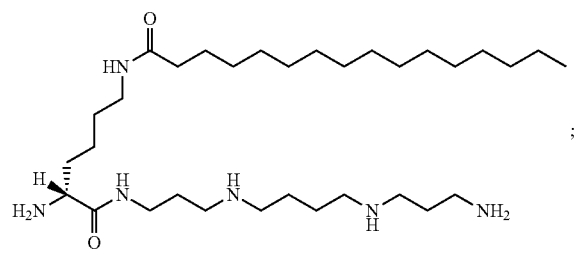

the salt is not in admixture with more than 5 wt % of any other solid or liquid chemical; the salt is in the form of a pharmaceutical composition; the salt is in the form of a pharmaceutical composition for solid dosage administration.

In a convenient process for preparing salts of the present disclosure, the combination of polyamine and fatty acid or other hydrophobic carboxylic acid does not include any additional anions or cations. Such a combination may be prepared by combining the free base form of the polyamine with the free acid form of the fatty acid or HCA. The combination will be in the form of a salt, where the salt forms between the protonated polyamine and the deprotonated fatty acid (or deprotonated HCA). Thus, a convenient process for preparing the salts of the present disclosure is to combine an uncharged polyamine pharmaceutical with an uncharged hydrophobic carboxylic acid in a solvent under proton transfer conditions to form a salt of a positively charged polyamine pharmaceutical, i.e., a cationic polyamine pharmaceutical and a negatively charged hydrophobic carboxylate, i.e., an anionic hydrophobic carboxylate, and separating the salt from the solvent.

For example, a convenient process for preparing salts of the present disclosure entails combining the free base form of the polyamine with the free acid form of the hydrophobic carboxylic acid in a solvent that allows for proton transfer involving the carboxylic acid and the polyamine. Thus, the present disclosure provides a method comprising: combining a polyamine, a hydrophobic carboxylic acid and a solvent so as to provide a solution; and thereafter isolating a solid residue from the solution, wherein the residue comprises a salt formed between the polyamine and the hydrophobic carboxylic acid. Optionally, the method may be further characterized by any one or more (e.g., any two, any three, any four) of the following.

The polyamine is a pharmaceutically active polyamine such as identified herein. For example, any of the polyamines of formulae (I)-(IV), 1426, 1501, 1505, 1569, 2030, DENSpm, DEHSpm, squalamine, deoxyspergualin, F14512, Mozobil, Trientine, Gentamicin, Polymyxin B, MGBG and spermidine may be used in the method. The hydrophobic carboxylic acid is any of the hydrophobic carboxylic acids identified herein. For example, the hydrophobic carboxylic acid may have a water solubility of less than 10 g/L water, may have the formula R—COOH where R has 6-20 carbon atoms, or 8-16 carbon atoms, or 10-14 carbon atoms, or may be a fatty acid selected from octanoic acid, decanoic acid, dodecanoic acid, tetradecanoic acid and hexadecanoic acid. The hydrophobic carboxylic acid may be a mixture of hydrophobic carboxylic acids. In order to prepare a high purity PPA-HCA salt, each of the polyamine and the hydrophobic carboxylic acid may be of high purity, e.g., one or both of the components may be, e.g., at least 90%, or at least 95%, or at least 96%, or at least 97%, or at least 98%, or at least 99%, or at least 99.5% pure on a weight basis. One or both of the polyamine and the hydrophobic carboxylic acid may be pharmaceutical grade, prepared by GMP. In one embodiment, the polyamine is AMXT 1501 and the hydrophobic carboxylic acid is capric acid.

The polyamine and the hydrophobic carboxylic acid may be combined in relative amounts so as to provide the desired salt stoichiometry. For example, if a 1:1 molar stoichiometry PPA:HCA salt is desired, then equal, or approximately equal, molar amounts of polyamine and hydrophobic carboxylic acid are combined with the solvent. Thus, in one embodiment, about 1.0 mole, e.g., 0.9-1.1 moles of hydrophobic carboxylic acid are combined with each 1.0 mole of polyamine. If a 1:2 molar stoichiometry PPA:HCA salt is desired, then exactly or about 2.0 moles, e.g., 1.8-2.2 moles of hydrophobic carboxylic acid are combined with each 1.0 mole of polyamine. If a 1:3 molar stoichiometry of PPA:HCS salt is desired, then exactly or about 3.0 moles, e.g., 2.7-3.3 moles of hydrophobic carboxylic acid are combined with each 1.0 mole of polyamine. If a 1:4 molar stoichiometry PPA:HCA salt is desired, then exactly or about 4.0 moles, e.g., 3.6-4.4 moles of hydrophobic carboxylic acid are combined with each 1.0 mole of polyamine. In one embodiment, 1 mole of the polyamine AMXT 1501 is combined with 2 moles of the hydrophobic carboxylic acid capric acid. To be clear, when reference is made to, e.g., 1.8-2.2 moles of hydrophobic carboxylic acid being combined with each 1.0 mole of polyamine, that excludes combining less than about 1.8 moles or more than about 2.2 moles of hydrophobic carboxylic acid with each 1.0 mole of polyamine.

The solvent should facilitate proton transfer between the hydrophobic carboxylic acid and the polyamine. For example, the solvent may be a pure polar protic solvent or it may be a mixture of solvents comprising a polar protic solvent. A suitable polar protic solvent is water, e.g., a water selected from deionized water and distilled water. Another suitable polar protic solvent is a lower-chain alcohol, e.g., methanol or ethanol. In one embodiment, 1 mole of the polyamine AMXT 1501 is combined with 2 moles of the hydrophobic carboxylic acid capric acid in a solvent selected from water and methanol.

The components may be combined in any order so as to form a solution. For example, the polyamine and the hydrophobic carboxylic acid may be added to the solvent so as to provide the solution. In one embodiment, the polyamine is dissolved in the solvent, and then the hydrophobic carboxylic acid is gradually added to the solution of solvent and polyamine. The process may be performed in a batch or a continuous mode. In a batch mode, a container receives the full charge of solvent, polyamine and hydrophobic carboxylic acid, the salt is formed in the container. The polyamine, the hydrophobic carboxylic acid and the solvent may be combined so as to provide a clear solution, in other words, there is no insoluble material present in the solution. Typically, the polyamine, the hydrophobic carboxylic acid and the solvent are combined at a temperature within the range of 10-30'C, although other temperatures may be used. In a continuous mode, continuous flow techniques could be used for the production and isolation of the PPA:HCA salt forms described. Use of available flow apparatus, wherein solutions of the polyamine free base, in a suitable solvent such as methanol, are mixed with a co-solvent in which the salt is not soluble, such as acetonitrile, in a flow cell apparatus, allowing the continuous production of the insoluble, or soluble form of the PPA:HCA salt.

After the salt is formed, the solvent is separated from the salt to provide a residue that is, or includes, the salt. When the solvent is not too volatile, then it may be removed from the solution by a process such as evaporation or distillation, so as to isolate the residue from the solution. As another option, a co-solvent (an example being acetonitrile) may be added to the solution, whereupon a precipitate comes out of solution, and the resulting solution is referred to as the supernatant. The co-solvent may also be referred to as a non-solvent, since the salt is not soluble in the non-solvent. The precipitate, also referred to as a residue, may be separated from the residue, e.g., by decantation, so as to isolate the residue from the solution. As yet another option, the solution may be chilled to a temperature such that the salt is no longer soluble in the solvent and thus forms the residue in the form of a precipitate. As in the case when a co-solvent is used to form the precipitate, the supernatant may be separated from the residue so as to isolate the residue from the solution.

In one embodiment, the residue comprises at least 50%, or at least 95%, or at least 99% by weight of the salt. In other words, at least 50% of the weight of the residue is the PPA:HCA salt, or at least 95% of the weight of the residue is the PPA:HCA salt, or at least 99% of the weight of the residue is the PPA:HCA salt. For example, in order to obtain this yield, most or all of the solvent is removed from the residue so that it is essentially solvent-free. Also, in one embodiment, the residue only contains PPA:HCA and contains no other materials, or contains only a minor amount (e.g., less than 1, or less than 2, or less than 3 wt %) of other materials such as residual polyamine or residual hydrophobic carboxylic acid. Other materials may, however, be combined with the solvent, e.g., a preservative or antimicrobial agent, so that the residue is not entirely composed of PPA:HCA. In one embodiment, the residue contains little or no (e.g., less than 1, or less than 2, or less than 3 wt %) inorganic species such as chloride or phosphate. In one embodiment the residue consists of, or consists essentially of, polyamine, hydrophobic carboxylic acid, and salt formed therebetween.

Once the residue is formed, it or a portion thereof may be combined with additional components as described herein so as to form a pharmaceutical composition suitable for administration to a subject, e.g., by ingestion. Those additional components may include diluents, e.g. lactose and microcrystalline cellulose, disintegrants, e.g. sodium starch glycolate and croscarmellose sodium, binders, e.g. PVP and HPMC, lubricants, e.g. magnesium stearate, and glidants, e.g. colloidal $SiO_2$. For example, the method may further comprise forming a solid dosage form selected from a pill, a tablet, a capsule, a lozenge, a caplet, and a pastille, from the residue or a portion thereof. The PPA-HCA salt may be in sterile form, so as to be used in the manufacture of a pharmaceutical agent.

As mentioned above, a charged form of the polyamine and/or a charged form of the hydrophobic carboxylic acid may be utilized as a reactant to prepare a PPA:HCA of the present disclosure.

An acid addition salt of a polyamine may be formed by bringing the polyamine into contact with a suitable inorganic or organic acid under conditions known to the skilled person. An acid addition salt may, for example, be formed using an inorganic acid. Suitable inorganic acids may be selected from the group consisting of hydrochloric acid, hydrobromic acid, sulphuric acid and phosphoric acid. An acid addition salt may also be formed using an organic acid. Suitable organic acids may be selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

A base addition salt of a carboxylic acid may be formed by bringing the carboxylic acid into contact with a suitable inorganic or organic base under conditions known to the skilled person. Suitable inorganic bases which form suitable base addition salts include the hydroxide form of any of lithium, sodium, potassium, calcium, magnesium or barium. Suitable organic bases which form suitable base addition salts include aliphatic, alicyclic or aromatic organic amines such as methylamine, trimethylamine and picoline, alkylammonias and ammonia.

In a convenient process for preparing salts of the present disclosure, the polyamine is provided as its free base form, while the carboxylic acid is provided as its protonated acid form, and these components are mixed together. In this case, and depending on the stoichiometry of the components, the combination of polyamine and carboxylic acid may result in four species: polyamine, carboxylic acid, cation and anion. The cation may be selected from, for example, proton, ammonium, sodium, and calcium. The anion may be selected from, for example, hydroxide, carboxylate, and halide such as fluoride, chloride and iodide. Upon mixing, the cation and anion will form a salt, and the polyamine and the carboxylic acid will form a salt of the present disclosure, assuming the mixing is performed under conditions which allow for PPA:HCA salt formation, which typically requires the presence of water.

The combination of polyamine (in charged or uncharged form) and carboxylic acid (in charged or uncharged form) may be characterized in terms of the molar ratio of the two components. In the following discussion, the term polyamine refers to both charged and uncharged polyamine, and the term carboxylic acid refers to both charged and uncharged carboxylic acid. The relative amounts of polyamine and carboxylic acid present in the composition may be varied. In part, the relative amounts may reflect the number of amine groups present in the polyamine. As mentioned previously, in one embodiment the polyamine has two amine groups, while in another embodiment the polyamine has three amine groups, and in yet another embodiment the polyamine has four amine group, while in still another embodiment the polyamine has five amine groups, and in a further embodiment the polyamine has six or more amine groups, where amine groups are selected from primary, secondary and tertiary amines, independently selected at each occurrence. The amine groups are so-called protonatable amine groups, which refers to an amine group which is capable of bonding with a proton so as to form a charged ammonium species. NH groups adjacent to a carbonyl group, i.e., amide groups, are not protonatable amine groups since the protonated form of an amide group is unstable. The skilled organic chemist recognizes and/or may readily determine using known techniques, which amine groups may be protonated in dilute solution with a proton acid. In general, primary, secondary and tertiary amine groups are typically protonatable.

In one embodiment, each mole of polyamine is associated with 1, or with about 1 mole of HCA to form an exemplary salt of the present disclosure. An exemplary salt is conveniently formed by combining 1 mole of PPA with 1 mole of HCA, so that the salt has a 1:1, or about a 1:1 molar ratio of PPA to HCA. However, the present disclosure also provides that more or less than 1 mole of HCA may be combined with each 1 mole of PPA. In such a situation, the resulting 1:1 PPA:HCA salt, optionally designated as PPA:(HCA)$_1$, may be in admixture with unprotonated PPA or diprotonated PPA, depending on how much HCA is combined with the PPA. For example, a composition of the present disclosure may include a salt having a 1:1 molar ratio of PPA to HCA, where this salt is in combination with non-protonated polyamine. In addition, the present disclosure provides a salt having a 1:2 molar ratio of PPA to HCA, optionally denoted as PPA:(HCA)$_2$, where this salt may be in combination with a salt having a 1:1 molar ratio of PPA to HCA. In one embodiment, each mole of polyamine is associated with 2, or with about 2 moles of HCA to form a salt of the present disclosure. Such a salt has a 1:2, or about a 1:2 molar ratio of PPA to HCA. In addition, the present disclosure provides a salt having a 1:3 molar ratio of PPA to HCA, optionally denoted as PPA:(HCA)$_3$, where this salt is in combination with a salt having a 1:2 molar ratio of PPA to HCA, optionally denoted as PPA:(HCA)$_2$, to provide a PPA:(HCA)$_3$/PPA:(HCA)$_2$ mixture.

The relative amounts of polyamine and carboxylic acid may be described in terms of equivalents, where 1 mole of polyamine with 5 amine groups has 5 equivalents of amine and 1 mole of carboxylic acid with 1 carboxylic acid group has 1 equivalent of carboxylic acid. For example, when the polyamine is AMXT 1501, there are four amine groups present in the molecule. In one embodiment of the invention, two moles of AMXT 1501 are combined with 1 mole of carboxylic acid, such that the polyamine and carboxylic acid are combined in an 8:1 equivalent ratio (8 equivalents of amine groups and 1 equivalent of carboxyl groups). In another embodiment of the invention, 1 mole of AMXT 1501 is combined with 4 moles of carboxylic acid, such that the polyamine and carboxylic acid are combined in a 1:1 equivalent ratio. As a further example, 1 mole of AMXT 1501 is combined with 8 moles of carboxylic acid, such that the polyamine and carboxylic acid are combined in a 1:2 equivalent ratio (there being 4 amine groups for every 8 carboxyl groups, providing for a 1:2 equivalent ratio). Thus, as an illustration, a AMXT 1501:(capric acid)$_2$ salt, i.e., the dicaprate salt of AMXT 1501, may be in admixture with, e.g., some AMXT 1501:(capric acid)$_1$ salt, i.e., the monocaprate salt of AMXT 1501, and/or some AMXT 1501 (capric acid)$_3$ salt, i.e., the tricaprate salt of AMXT 1501. Likewise, a AMXT 1501:(capric acid)$_1$ salt may be in admixture with, e.g., some AMXT 1501 and/or some AMXT 1501(capric acid)$_2$ salt. In this illustration, AMXT 1501 is used as an exemplary polyamine, however, other polyamines as disclosed herein may be substituted for AMXT 1501 in this illustration.

In one embodiment, the present disclosure provides a method for preparing a salt of the present disclosure, where the method comprises combining a polyamine pharmaceutical agent, a hydrophobic carboxylic acid and a solvent so as to provide a solution; and isolating a solid residue from the solution, wherein the solid residue comprises a salt of present disclosure. Optionally, the method may be described by one or more of the following features: the solvent comprises water, methanol or a combination thereof; 1.8-2.2 moles of hydrophobic carboxylic acid are combined with each 1.0 mole of polyamine pharmaceutical agent; the solid residue is formed by precipitation from the solution; the method further comprises formulating the solid residue or portion thereof into a solid dosage form pharmaceutical.

The following are additional exemplary embodiments of PPA:HCA salts of the present disclosure. In one embodiment the present disclosure provides a composition of AMXT 1501 dicaprate which is a salt form of the components having the molecular formulae and structures shown below:

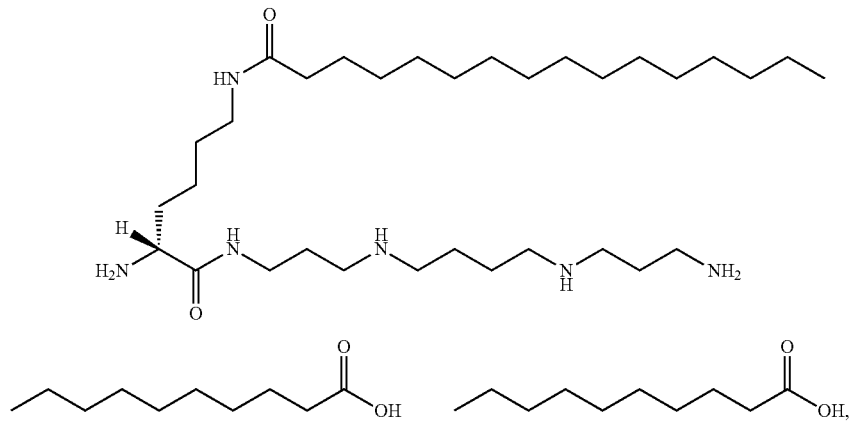

where the components form a dicaprate salt of the polyamine and capric acid. AMXT 1501 dicaprate might also be denoted by the term (AMXT 1501 2H$^+$) (R—COO$^-$)$_2$, where R is C$_9$, e.g., n-nonyl. In general, R—COOH is not very water soluble and may be described as water insoluble, where exemplary R groups have about 9 carbons (e.g., capric acid) up to about 23 carbons (e.g., cholic acid). The dicaprate salt may include any two of the primary and secondary amine groups present as shown in the polyamine in a protonated form. For example, both primary amine groups may be protonated, or both secondary amine groups may be protonated, or one primary and one secondary amine group may be protonated. In general, the more basic amine groups will be protonated first, where tertiary amine groups are generally more basic than secondary amine groups, and secondary amine groups are generally more basic than primary amine groups. One such structure is shown below:

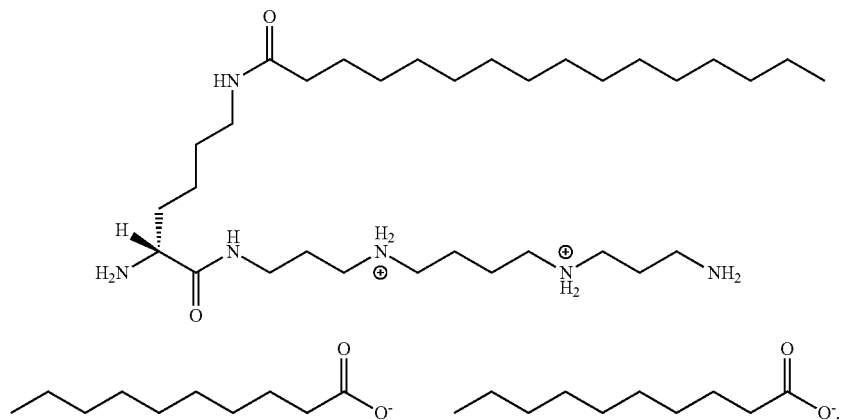

In one embodiment the present disclosure provides a composition of AMXT 1569 dicaprate which is a salt form of the components having the molecular formulae and structures shown below:

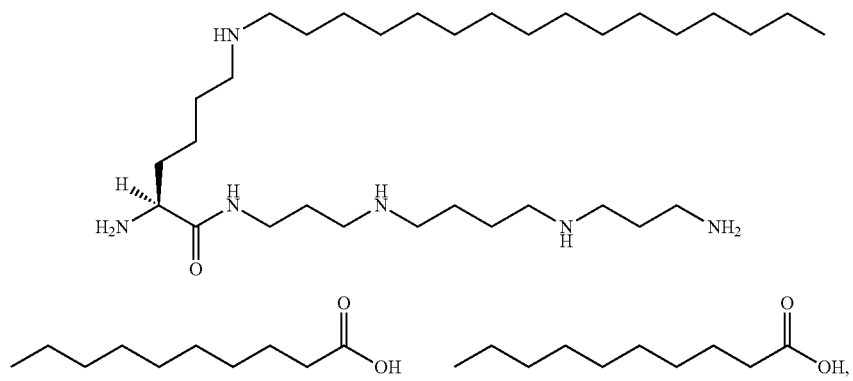

where the components form a dicaprate salt of the polyamine and capric acid. The dicaprate salt may include any two of the primary and secondary amine groups present as shown in the polyamine, in a protonated form. For example, both primary amine groups may be protonated, or both secondary amine groups may be protonated, or one primary and one secondary amine group may be protonated. One such structure is shown below:

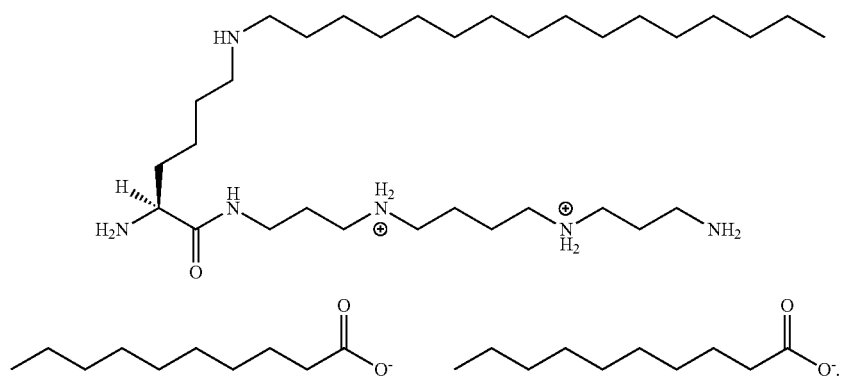

In one embodiment the present disclosure provides a composition of AMXT 2030 dicaprate which is a salt form of the components having the molecular formulae and structures shown below:

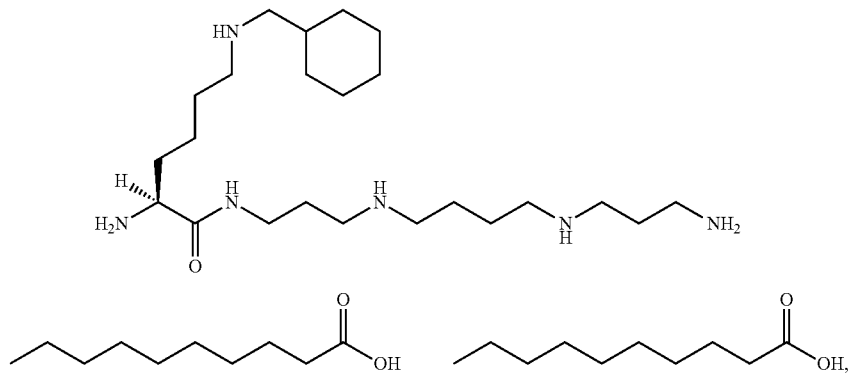 [SMILES: NCCCNCCCCNCCCNC(=O)[C@@H](N)CCCCNCC1CCCCC1 ; CCCCCCCCCC(=O)O ; CCCCCCCCCC(=O)O]

-continued

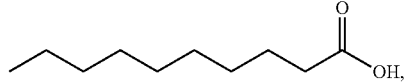

where the components form a dicaprate salt of the polyamine and capric acid. The dicaprate salt may include any two of the primary and secondary amine groups present as shown in the polyamine, in a protonated form. For example, both primary amine groups may be protonated, or both secondary amine groups may be protonated, or one primary and one secondary amine group may be protonated. One such structure is shown below:

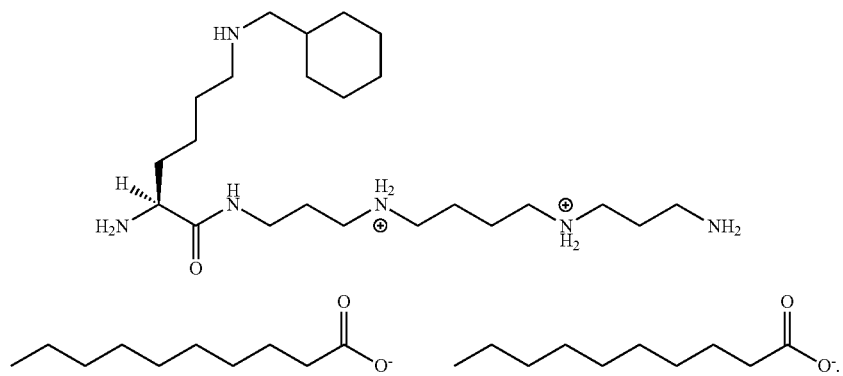

In one embodiment the present disclosure provides a composition of AMXT 1426 dicaprate which is a salt form of the components having the molecular formulae and structures shown below:

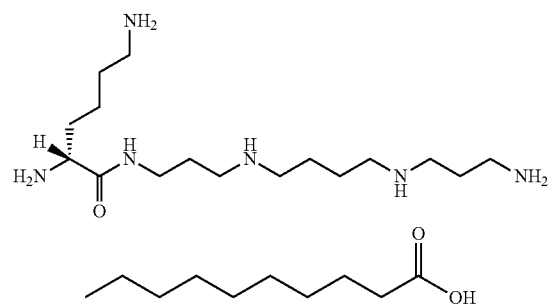

any two of the primary and secondary amine groups present as shown in the polyamine, in a protonated form. For example, both primary amine groups may be protonated, or both secondary amine groups may be protonated, or one primary and one secondary amine group may be protonated. One such structure is shown below:

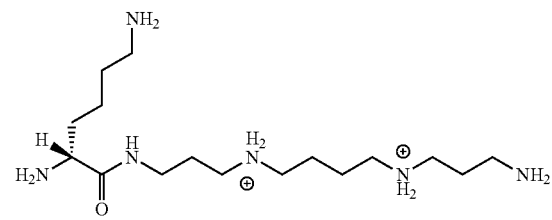

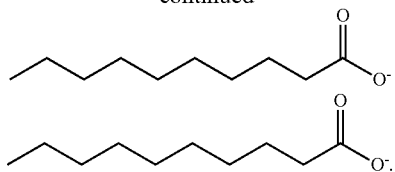

In one embodiment the present disclosure provides a composition of AMXT 1505 dicaprate which is a salt form of AMXT 1505 polyamine and two capric acids, where such as a salt is shown below:

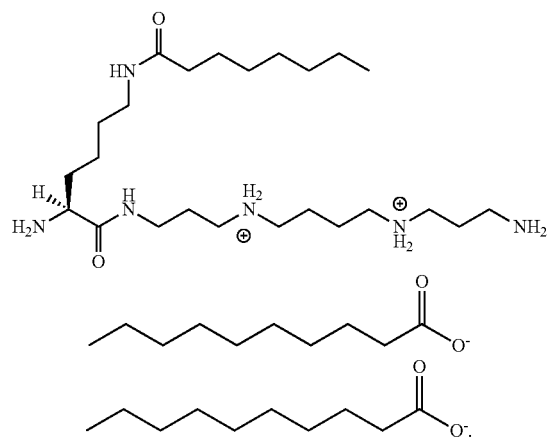

In one embodiment, the PPA is a protonated form of the polyamine known as DENSpm, where any one or more of the NH groups of DENSpm may be protonated and associated with a HCA so as to provide a protonated form of the polyamine. In one embodiment, one of the four NH groups present in DENSpm is protonated and associated with an HCA so as to form a salt of the present disclosure. In one embodiment, two of the NH groups of DENSpm are protonated and associated with HCAs so as to form a salt of the present disclosure. In one embodiment, three of the NH groups in DENSpm are protonated and associated with HCAs to form a salt of the present disclosure. In yet another embodiment, all four of the NH groups present in DENSpm are protonated and associated with HCAs so as to form a salt of the present disclosure. While such a salt of the present disclosure will necessarily comprise DENSpm in protonated form associated with at least one HCA, the salt may also be associated with other species as mentioned herein, e.g., solvent molecules and/or non-HCA anionic species.

In one embodiment, the PPA is a protonated form of the polyamine known as squalamine, where any one or more of the NH and NH$_2$ groups of squalamine may be protonated and associated with a HCA so as to provide a protonated form of the polyamine. In one embodiment, one of the two NH groups present in squalamine is protonated and associated with an HCA so as to form a salt of the present disclosure. In one embodiment, two of the NH groups of squalamine are protonated and associated with HCAs so as to form a salt of the present disclosure. In one embodiment, the NH$_2$ group present in squalamine is protonated and associated with an HCA so as to form a salt of the present disclosure. In yet another embodiment, one of the NH groups and the NH$_2$ group present in squalamine are protonated and associated with HCAs so as to form a salt of the present disclosure. In still another embodiment, both of the NH groups and the NH$_2$ group present in squalamine are protonated and associated with HCAs so as to form a salt of the present disclosure. While such a salt of the present disclosure will necessarily comprise squalamine in protonated form associated with at least one HCA, the salt may also be associated with other species as mentioned herein, e.g., solvent molecules and/or non-HCA anionic species.

In one embodiment, the PPA is a protonated form of the polyamine known as deoxyspergualin, where any one or more of the NH and NH$_2$ groups of deoxyspergualin may be protonated and associated with a HCA so as to provide a protonated form of the polyamine. In one embodiment, one NH group present in deoxyspergualin is protonated and associated with an HCA so as to form a salt of the present disclosure. In one embodiment, one NH$_2$ group of deoxyspergualin is protonated and associated with HCAs so as to form a salt of the present disclosure. In yet another embodiment, one NH group and one NH$_2$ group present in deoxyspergualin are protonated and associated with HCAs so as to form a salt of the present disclosure. While such a salt of the present disclosure will necessarily comprise deoxyspergualin in protonated form associated with at least one HCA, the salt may also be associated with other species as mentioned herein, e.g., solvent molecules and/or non-HCA anionic species.

In one embodiment, the PPA is a protonated form of the polyamine known as F14512, where any one or more of the NH and NH$_2$ groups of F14512 may be protonated and associated with a HCA so as to provide a protonated form of the polyamine. In one embodiment, one of the two NH groups present in F14512 is protonated and associated with an HCA so as to form a salt of the present disclosure. In one embodiment, two of the NH groups of F14512 are protonated and associated with HCAs so as to form a salt of the present disclosure. In one embodiment, three NH groups of F14512 are protonated as associated with an HCA so as to form a salt of the present disclosure. In one embodiment, the NH$_2$ group present in F14512 is protonated and associated with an HCA so as to form a salt of the present disclosure. In yet another embodiment, one of the NH groups and the NH$_2$ group present in F14512 are protonated and associated with HCAs so as to form a salt of the present disclosure. In still another embodiment, two of the NH groups and the NH$_2$ group present in F14512 are protonated and associated with HCAs so as to form a salt of the present disclosure. While such a salt of the present disclosure will necessarily comprise F14512 in protonated form associated with at least one HCA, the salt may also be associated with other species as mentioned herein, e.g., solvent molecules and/or non-HCA anionic species.

In one embodiment, the PPA is a protonated form of the polyamine known as Mozobil, where any one or more of the NH groups of Mozobil may be protonated and associated with a HCA so as to provide a protonated form of the polyamine. In one embodiment, one of the NH groups present in Mozobil is protonated and associated with an HCA so as to form a salt of the present disclosure. In one embodiment, two of the NH groups of Mozobil are protonated and associated with HCAs so as to form a salt of the present disclosure. In one embodiment, three NH groups of Mozobil are protonated as associated with an HCA so as to form a salt of the present disclosure. In one embodiment, four NH groups present in Mozobil are protonated and associated with an HCA so as to form a salt of the present disclosure. While such a salt of the present disclosure will necessarily comprise Mozobil in protonated form associated with at least one HCA, the salt may also be associated with other species as mentioned herein, e.g., solvent molecules and/or non-HCA anionic species.

In one embodiment, the PPA is a protonated form of the polyamine known as Trientine, where any one or more of the NH and NH$_2$ groups of Trientine may be protonated and associated with a HCA so as to provide a protonated form of the polyamine. In one embodiment, one of the two NH groups present in Trientine is protonated and associated with an HCA so as to form a salt of the present disclosure. In one embodiment, two of the NH groups of Trientine are protonated and associated with HCAs so as to form a salt of the present disclosure. In one embodiment, one NH$_2$ group present in Trientine is protonated and associated with an HCA so as to form a salt of the present disclosure. In one embodiment, both NH$_2$ groups present in Trientine are protonated and associated with an HCA so as to form a salt of the present disclosure. In yet another embodiment, one of the NH groups and one of the NH$_2$ group present in Trientine are protonated and associated with HCAs so as to form a salt of the present disclosure. In still another embodiment, two of the NH groups and one NH$_2$ group present in Trientine are protonated and associated with HCAs so as to form a salt of the present disclosure. In still another embodiment, one of the NH groups and two NH$_2$ groups present in Trientine are protonated and associated with HCAs so as to form a salt of the present disclosure. While such a salt of the present disclosure will necessarily comprise Trientine in protonated form associated with at least one HCA, the salt may also be associated with other species as mentioned herein, e.g., solvent molecules and/or non-HCA anionic species. Trientine is also known as triethylenetetramine, abbreviated TETA, or as trien.

In one embodiment, the PPA is a protonated form of the polyamine known as Gentamicin, where any one or more of the NH and NH$_2$ groups of Gentamicin may be protonated and associated with a HCA so as to provide a protonated form of the polyamine. In one embodiment, one of the NH groups present in Gentamicin is protonated and associated with an HCA so as to form a salt of the present disclosure. In one embodiment, two of the NH groups of Gentamicin are protonated and associated with HCAs so as to form a salt of the present disclosure. In one embodiment, one NH$_2$ group present in Gentamicin is protonated and associated with an HCA so as to form a salt of the present disclosure. In one embodiment, two NH$_2$ groups present in Gentamicin are protonated and associated with an HCA so as to form a salt of the present disclosure. In yet another embodiment, one of the NH groups and one of the NH$_2$ group present in Gentamicin are protonated and associated with HCAs so as to form a salt of the present disclosure. In still another embodiment, two of the NH groups and one NH$_2$ group present in Gentamicin are protonated and associated with HCAs so as to form a salt of the present disclosure. In still another embodiment, one of the NH groups and two NH$_2$ groups present in Gentamicin are protonated and associated with HCAs so as to form a salt of the present disclosure. While such a salt of the present disclosure will necessarily comprise Gentamicin in protonated form associated with at least one HCA, the salt may also be associated with other species as mentioned herein, e.g., solvent molecules and/or non-HCA anionic species.

In one embodiment, the PPA is a protonated form of the polyamine known as Polymyxin B, where any one or more of the NH$_2$ groups of Polymyxin B may be protonated and associated with a HCA so as to provide a protonated form of the polyamine. In one embodiment, one of the NH$_2$ groups present in Polymyxin B is protonated and associated with an HCA so as to form a salt of the present disclosure. In one embodiment, two of the NH$_2$ groups of Polymyxin B are protonated and associated with HCAs so as to form a salt of the present disclosure. In one embodiment, three of the NH$_2$ groups present in Polymyxin B is protonated and associated with an HCA so as to form a salt of the present disclosure. In one embodiment, four NH$_2$ groups present in Polymyxin B are protonated and associated with an HCA so as to form a salt of the present disclosure. While such a salt of the present disclosure will necessarily comprise Polymyxin B in protonated form associated with at least one HCA, the salt may also be associated with other species as mentioned herein, e.g., solvent molecules and/or non-HCA anionic species.

In one embodiment, the PPA is a protonated form of the polyamine or polyguanidine known as MGBG, where any one or more of the NH$_2$ groups of MGBG may be protonated and associated with a HCA so as to provide a protonated form of the polyamine. In one embodiment, one of the NH$_2$ groups present in MGBG is protonated and associated with an HCA so as to form a salt of the present disclosure. In one embodiment, two of the NH$_2$ groups of MGBG are protonated and associated with HCAs so as to form a salt of the present disclosure. In one embodiment, three of the NH$_2$ groups present in MGBG is protonated and associated with an HCA so as to form a salt of the present disclosure. In one embodiment, four NH$_2$ groups present in MGBG are protonated and associated with an HCA so as to form a salt of the present disclosure. While such a salt of the present disclosure will necessarily comprise MGBG in protonated form associated with at least one HCA, the salt may also be associated with other species as mentioned herein, e.g., solvent molecules and/or non-HCA anionic species.

In one embodiment, the present disclosure provides a composition of spermidine dicaprate. In one embodiment, the PPA is a protonated form of the polyamine known as spermidine, where any one or more of the NH$_2$ groups of spermidine may be protonated and associated with a HCA so as to provide a protonated form of the polyamine. In one embodiment, one of the NH$_2$ groups present in spermidine is protonated and associated with an HCA so as to form a salt of the present disclosure. In one embodiment, two of the NH$_2$ groups of spermidine are protonated and associated with HCAs so as to form a salt of the present disclosure. In one embodiment, two NH$_2$ groups and one NH group present in spermidine are protonated and associated with an HCA so as to form a salt of the present disclosure. While such a salt of the present disclosure will necessarily comprise spermidine in protonated form associated with at least one HCA, the salt may also be associated with other species as mentioned herein, e.g., solvent molecules and/or non-HCA anionic species. In one embodiment, the PPA is a protonated form of spermidine, which has the formula shown below, where any one or more of the NH or NH$_2$ groups may be protonated so as to provide a protonated form of spermidine. For example, in one embodiment the present disclosure provides spermidine dicaprate, which is a salt form of the components having the molecular formulae and structures shown below:

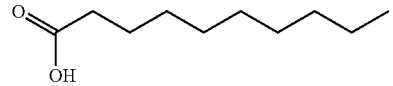

-continued

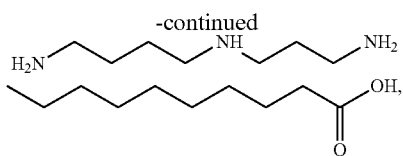

for example, a salt form of the formula

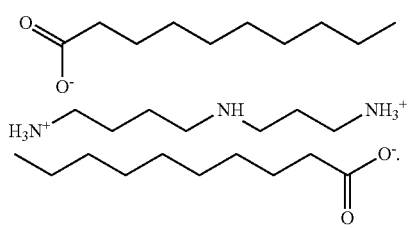

The foregoing are exemplary PPA:HCA salts of the present disclosure, which may be prepared by methods as described herein. In general, the PPA:HCA salts may be conveniently prepared by neutralization of an acid (the HCA component) by the base (the PPA component) in a suitable solvent such as water. In one embodiment, the present invention provides a composition comprising PPA, HCA and a suitable solvent to allow salt formation between PPA and HCA, e.g., water, methanol and mixtures thereof, as well as a composition consisting of, and a composition consisting essentially of, PPA, HCA and the suitable solvent. Such a composition will provide a salt of the present invention in solution, from which a salt of the present disclosure may be isolated.

Pharmaceutical Formulations

The salts of the present disclosure may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration. The salts may be formulated, alone or together, into suitable dosage unit formulations, also known as dosage forms, containing conventional non-toxic pharmaceutically acceptable inert (i.e., not biologically active) components such as carriers, adjuvants and vehicles appropriate for each route of administration. In addition to the treatment of warm-blooded animals such as mice, rats, horses, cattle, sheep, dogs, cats, monkeys, etc., the salts of the disclosure are effective for use in humans.

The pharmaceutical compositions for the administration of the salts of this disclosure may conveniently be presented in dosage unit form and may be prepared by any of the methods well known in the art of pharmacy. The scientific field of pharmaceutics is focused on delivery of pharmaceutical agents in a form that maximizes the benefit to the patient being treated. Without being bound by theory, formulation of polyamine drugs as their carboxylic acid salts may increase the lipophilicity of the resulting salt composition, facilitating uptake by cellular components of the gastrointestinal tract of treated animals. In fact, the mammalian gastrointestinal utilizes bile acid secretion to facilitate the dietary uptake of more lipophilic components of the diet.

All methods include the step of bringing the active ingredient, i.e., the salt of the present disclosure, into association or combination with the inert components which constitute one or more accessory ingredients. In general, the pharmaceutical compositions are prepared by uniformly and intimately bringing the salt of the present disclosure into association with a liquid carrier or a finely divided solid carrier or both, and then, if necessary, shaping the product into the desired formulation. In the pharmaceutical composition, the active salt of the present disclosure is included in an amount sufficient to produce the desired effect upon the process or condition of diseases. As used herein, the term "composition" is intended to encompass a product comprising the specified ingredients optionally in specified amounts, as well as any product which results, directly or indirectly, from a combination of the specified ingredients in the specified amounts.

In one embodiment, the pharmaceutical composition is a solid dosage form intended for oral use. For many reasons, an oral composition, and particularly a solid oral dosage form, is advantageous and convenient for both the patient and the medical practitioner responsible for developing the therapeutic regime. An oral composition avoids the complications, cost and inconvenience of administration via IV injection or infusion which must be done by a medical professional in a hospital or out-patient setting which exposes him or her to hospital-based infections and illnesses. In particular, patients undergoing treatment for cancer may be immunocompromised individuals and particularly susceptible to hospital-based infections and illnesses. An oral formulation, such as a pill or tablet, may be taken outside of a hospital setting, increasing the potential for subject ease of use and compliance. This permits a subject to avoid infection risks concomitant with IV administration and hospital visits. In addition, oral delivery may avoid the high concentration peak and rapid clearance associated with an IV bolus dose.

Examples of oral solid dosage forms include pills, tablets, capsules, granules, and microspheres, any of which may include an enteric-coating to protect the pharmaceutical composition from acid-degradation by stomach environment, or to maximize delivery to intestinal sections where absorption is enhanced. The solid dosage form may be chewable or swallowable, or have any suitable ingestible form. In one embodiment, the solid dosage form contains little or no water, e.g., less than 0.1 wt % water, or less than 0.2 wt % water, or less than 0.3 wt % water, or less than 0.4 wt % water, or less than 0.5 wt % water, or less than 1 wt % water, or less than 1.5 wt % water, or less than 2 wt % water.

Solid dosage forms may be prepared according to any method known to the art for the manufacture of pharmaceutical compositions. Such compositions may contain one or more inert components, where exemplary inert components may be selected from the group of sweetening agents, flavoring agents, coloring agents and preserving agents in order to provide pharmaceutically elegant and palatable preparations. Solid dosage forms of the present disclosure contain the salt of the present disclosure in optional admixture with inert and non-toxic pharmaceutically acceptable excipients which are suitable for the manufacture of the solid dosage form.

Excipients for solid dosage forms are well known in the art, and are selected to provide various benefits including ease of administration to the subject, improved dosing compliance, consistency and control of drug bioavailability, assistance with enhanced bioavailability, improved API stability including protection from degradation, and to contribute to the ease of production of a robust and reproducible physical product. Excipients are commonly subdivided into various functional classifications, depending on the role that they are intended to play in the formulation. For solid dosage forms, common excipient roles and exemplary materials that fulfill that role are diluents, e.g. lactose and microcrystalline cellulose, disintegrants, e.g. sodium starch glycolate and croscarmellose sodium, binders, e.g. PVP and HPMC, lubricants, e.g. magnesium stearate, and glidants, e.g. colloidal $SiO_2$. Tablets and capsules often contain a diluent, filler or bulking agent, e.g., lactose. Excipients used to formulate polyamine drug agents should avoid those containing reducing sugar components in order to prevent formation of Schiff-base addition products as degradants.

Excipients may be, for example, inert diluents, such as calcium carbonate, sodium carbonate, and lactose; granulating and disintegrating agents, such as corn starch, and alginic acid; binding agents, such as starch, gelatin or acacia; and lubricating agents, such as magnesium stearate, stearic acid and talc. The tablets of the present disclosure, containing a PPA:HCA salt as disclosed herein, may be uncoated or they may be coated, e.g., with an enteric coating, by known techniques, in order to delay disintegration and absorption in the gastrointestinal tract and thereby provide a sustained action over a longer period. Compositions for oral use may also be formed as hard gelatin capsules wherein the biologically active salt of the present disclosure is mixed with an inert solid diluent, for example, calcium carbonate, kaolin, or as soft gelatin capsules wherein the salt is mixed with water or an oil medium, for example peanut oil, liquid paraffin, or olive oil.

In one embodiment, aqueous suspensions for pharmaceutical application contain the biologically active salt of the present disclosure in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the biologically active salt of the present disclosure in admixture with a dispersing or wetting agent, suspending agent and one or more preservatives.

Pharmaceutical compositions of the salts of the present disclosure may be in the form of a sterile injectable aqueous or oleagenous suspension. The salts of the present disclosure may be administered by subcutaneous injection. The salts of the present disclosure may also be administered in the form of suppositories for rectal administration. For topical use, creams, ointments, jellies, solutions or suspensions, etc., containing the salts of the present disclosure may be employed. The salts of the present disclosure may also be formulated for administered by inhalation. The salts of the present disclosure may also be administered by a transdermal patch by methods known in the art.

The pharmaceutical compositions and methods of the present disclosure may further comprise additional therapeutically active compounds which are beneficially applied in the treatment of a pathological condition experienced or potentially experienced by the subject receiving the pharmaceutically active salt of the present disclosure.

In the treatment, prevention, control, amelioration, or reduction of risk of cancer, the salts of the present disclosure will be administered at an appropriate dosage level that will generally be about 0.01 to 500 mg per kg patient body weight per day, which can be administered in single or multiple doses. Human dose levels, especially those used for cancer chemotherapy, are alternatively expressed in units of $mg/m^2/day$. The dose may be higher or lower at the discretion of the attending health care professional, based on that person's experience and knowledge in dealing with the specific medical condition being treated and the condition of the patient. Optionally, the dosage level will be about 0.1 to about 250 mg/kg per day; or about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be, for example, about 0.05 to 0.5, 0.5 to 5, or 1 to 50, or 5 to 50 mg/kg per day.

For oral administration, the compositions are preferably provided in a solid form, such as the form of pills, capsules, tablets and the like, containing 1.0 to 1000 milligrams of the salt of the present disclosure, particularly about 1, 5.0, 10.0, 15.0, 20.0, 25.0, 50.0, 75.0, 100.0, 150.0, 200.0, 250.0, 300.0, 400.0, 500.0, 600.0, 750.0, 800.0, 900, and 1000.0 milligrams of the salt of the present disclosure for the symptomatic adjustment of the dosage to the patient to be treated. The salts may be administered on a regimen of 1 to 4 times per day, preferably once or twice per day, at the discretion of the attending health care professional.

In one embodiment, the solid dosage form contains 10 mg, or 20 mg, or 30 mg, or 40 mg, or 50 mg, or 60 mg, or 70 mg, or 80 mg, or 90 mg, or 100 mg, or 110 mg, or 120 mg, or 130 mg, or 140 mg, or 150 mg of the protonated form of the polyamine (PPA), where that PPA will, however, be present in the solid dosage from as a salt with HCA. The amount of the PPA present in the solid dosage form may also be characterized in terms of a range of possible amounts, where the lower and upper limits of that range are selected from the amounts just described, i.e., from 10 to 150 mg, or numbers in between, e.g., 50 to 100 mg. A tablet or pill will typically have a total weight of at least 50 mg.

In one embodiment, the solid dosage form provides a therapeutically effective systemic plasma level of a polyamine pharmaceutical agent for a period of at least 4, 5, 6, 7, 8, 9, 10, 11, 12, 13, 14, 15, 16, 17, 18, 19, 20, 21, 22, 23, 24, 30, 36, or 48 hours. In further embodiments, the solid dosage form provides a therapeutically effective systemic plasma level of a polyamine pharmaceutical agent for at least an 8 hour period. In further embodiments, the solid dosage form provides a therapeutically effective systemic plasma level of a polyamine pharmaceutical agent for at least a 14 hour period. In further embodiments, the solid dosage form provides a therapeutically effective systemic plasma level of a polyamine pharmaceutical agent for at least an 18-hour period. In further embodiments, the solid dosage form provides a therapeutically effective systemic plasma level of a polyamine pharmaceutical agent for at least a 24-hour period.

In one embodiment, the solid dosage form provides a plasma level of a polyamine pharmaceutical agent of at least 25, 50, 55, 60, 65, 75, 80, 85, 90, or 95 percent of the peak plasma concentration for at least 4 hours. In certain embodiments, the solid dosage form provides a plasma level of a polyamine pharmaceutical agent of at least 75% of the peak plasma concentration for at least 4, 6, 8, 10, 12, 14, 16, 18, 20, 22, or 24 hours. In certain embodiments, the solid dosage form provides a plasma level of a polyamine pharmaceutical agent of at least 75% of the peak plasma concentration for at least 4 hours. In certain embodiments, the solid dosage form provides a plasma level of a polyamine pharmaceutical agent of at least 75% of the peak plasma concentration for at least 6 hours. In certain embodiments, the solid dosage form provides a plasma level of a polyamine pharmaceutical agent of at least 75% of the peak plasma concentration for at least 10 hours. In certain embodiments, the solid dosage form provides a plasma level of a polyamine pharmaceutical agent of at least 50% of the peak plasma concentration for at least 6 hours. In certain embodiments, the solid dosage form provides a plasma level of a polyamine pharmaceutical agent of at least 50% of the peak plasma concentration for at least 12 hours. In certain embodiments, the solid dosage form provides a plasma level of a polyamine pharmaceutical agent of at least 50% of the peak plasma concentration for at least 18 hours. In certain embodiments, the solid dosage form provides a plasma level of a polyamine pharmaceutical agent of at least 25% of the peak plasma concentration for at least 18 hours. In further embodiments, the peak plasma concentration is a therapeutically effective concentration. In yet further embodiments, the percentage of peak plasma concentration is therapeutically effective over the given time period.

When treating, preventing, controlling, ameliorating, or reducing the risk of cell proliferative diseases such as cancer for which salts of the present disclosure are indicated, generally satisfactory results are obtained when the salts of the present disclosure are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. This dosage regimen may be adjusted to provide the optimal therapeutic response.

It will be understood, however, that the specific dose level and frequency of dosage for any particular patient may be varied and will depend upon a variety of factors including the activity of the specific salt employed, the metabolic stability and length of action of that salt, the age, body weight, general health, sex, diet, mode and time of administration, rate of excretion, drug combination, the severity of the particular condition, and the subject undergoing therapy. This invention facilitates oral and other administration routes used clinically and improves patient compliance.

As mentioned above, the pharmaceutical composition may be formulated as a tablet, capsule or the like. For example, the pharmaceutical composition may comprise 0.1-50% of a PPA-HCA; 0.1-99.9% of a filler; 0-10% of a disintegrant; 0-5% of a lubricant; and, 0-5% of a glidant. As another example, the pharmaceutical composition comprises 0.1-50% of PPA-HCA; 0.1-99.9% of a filler; 0-10% of a disintegrant; 0-5% of a lubricant; and, 0-5% of a glidant. Optionally, the pharmaceutical composition comprises 10-300 mg of a polyamine pharmaceutical agent such as AMXT 1501 dicaprate, making up 2-50% of the tablet content or capsule fill content, 0-10% of a disintegrant, 0-5% of a lubricant, 0-5% of a glidant; and 30-98% of a filler. In another embodiment, the pharmaceutical composition comprises a desired amount of PPA:HCA, 0.1-10% of a binder, 0-5% of a surfactant, 0-10% of an intergranular disintegrant, and 0-10% of an extragranular disintegrant. Examples of binders, fillers, surfactants, disintegrants, lubricants, intergranular disintegrant, extragranular disintegrant and glidants are known in the art, and examples are disclosed herein, and include, a binder selected from copolyvidone, hydroxypropyl-cellulose, hydroxypropylmethylcellulose, and povidone, a filler selected from a sugar, a starch, a cellulose, and a poloxamer; a surfactant selected from polyoxyethylene (20) sorbitan monooleate, a poloxamer, and sodium lauryl sulfate, an intergranular disintegrant selected from croscarmellose sodium, sodium starch glyconate, and crospovidone. For instance, a disintegrant selected from povidone and crospovidone; a lubricant which is magnesium stearate; and a glidant which is silicon dioxide.

For example, in one embodiment the present disclosure provides an oral pharmaceutical composition, preferably a solid dosage form, comprising AMXT 1501 dicaprate salt together with at least one oral pharmaceutically acceptable excipient, which yields a therapeutically effective systemic plasma AMXT 1501 level for at least a 12-hour period when orally administered to a subject. Optionally, the composition may be further characterized by one or more of the following: the composition yields a therapeutically effective systemic plasma AMXT 1501 level for at least a 24-hour period when orally administered to a subject; the plasma level of AMXT 1501 is at least 75% of the peak plasma concentration for 4 or more hours; the composition has an oral bioavailability of at least 20%, or at least 30%, or at least 40%; the composition yields a therapeutically effective plasma level of AMXT 1501 for at least a 24 hour period in the subject with once-daily dosing; the composition has a half-life of at least 12 hours or at least 18 hours; the composition does not have substantially dose-limiting side effects, e.g., gastrointestinal side effects such as nausea, vomiting, diarrhea, abdominal pain, oral mucositis, oral ulceration, pharyngitis, stomatitis, and gastrointestinal ulceration; the composition comprises about 25 mg to about 350 mg of AMXT 1501 in salt form; the composition is formulated as a tablet or capsule. In this exemplary embodiment, AMXT 1501 is used as an exemplary polyamine pharmaceutical agent and capric acid used as an exemplary hydrophobic carboxylic acid.

PPA-HCA Salts in Therapy

Of the myriad delivery modes for pharmaceutical agents, the oral route is by far the most optimum by consideration of patient convenience and compliance and is favored for biochemical targets that require sustained, durable engagement. The natural ability of the patients, be this a human or animal, to eliminate drug agents from the blood stream is balanced by continuous uptake via the oral route. Multiple doses can be conveniently administered over the course of a day. Patients can take these drugs in their homes or workplaces. Because of these specific reasons, optimization of the delivery of orally formulated drugs is an ongoing goal of pharmaceutical development process.

Delivery of PPAs in their hydrochloride salt forms is a generally used method for their initial animal and human testing. Examples of these are given in the above specification. Several PPAs have been approved for clinical use, despite challenges associated with their delivery. The present disclosure provides for the identification, preparation and use of polyamine pharmaceutical agents for their intended or desired therapeutic purposes, but in an easily administered and effective oral composition to achieve their intended or desired medicinal purpose.

In one embodiment, the present disclosure provides a method of treating cancer comprising administering to a subject in need thereof a therapeutically effective amount of a salt of the present disclosure. The PPA component of the salt of the present disclosure will be selected in order to be effective in the treatment of the cancer that needs treatment. The cancer may be, for example, breast cancer, prostate cancer, colon cancer or lung cancer. Other cancers that may be treated by appropriate selection of the PPA include neuroblastoma, pancreatic, bladder, melanoma, skin cancer, non-Hodgkin lymphoma, kidney cancer, head and neck cancers including glioblastoma, leukemia and other blood cancers, ovarian and thyroid cancers. The cancer may be a solid tumor. The cancer may be treated by PPAs that are specific for oncogenes, e.g., MYCN and RAS derived tumors. In one embodiment, the cancer is treated by administration of AMXT 1501 dicaprate salt, i.e., a compound of the formula PPA:(HCA)$_2$ where PPA is AMXT 1501 and HCA is capric acid, where administration may be by a solid oral dosage form.

In general, there is a myriad of therapeutic uses provided by polyamine-based therapeutics in addition to anti-cancer treatments. Polyamine-based agents have been described to have antibiotic activities, anti-viral actions, anti-inflammatory actions, anti-sepsis activity, anti-pain abilities, anti-psychotic actions, anti-aging effects, anti-heart damage effects, among many other actions. Oral delivery of these polyamine active agents would greatly benefit their desired pharmacological actions and improve therapeutic benefit for patients undergoing therapy for these aliments.

Exemplary Embodiments

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The following provides exemplary embodiments of the present disclosure.

1) A salt of a cationic protonated polyamine pharmaceutical agent and an anionic hydrophobic carboxylate.
2) The salt of any of embodiments 1 and 3-9 wherein the anionic hydrophobic carboxylate is a carboxylate form of a fatty acid selected from C$_8$-C$_{18}$ fatty acids.
3) The salt of any of embodiments 1-2 and 4-9 wherein the anionic hydrophobic carboxylate is a carboxylate form of a fatty acid selected from octanoic acid, decanoic acid, dodecanoic acid and tetradecanoic acid, or a fatty acid selected from decanoic acid, dodecanoic acid and tetradecanoic acid.
4) The salt of any of embodiments 1-3 and 5-9 wherein the anionic hydrophobic carboxylate is a carboxylate form of an organic carboxylic acid having a water solubility of less than 10 g/L as determined in water at 25° C. and pH 7.
5) The salt of any of embodiments 1-4 and 6-9 wherein the cationic protonated polyamine is a protonated form of a therapeutically effective polyamine that has from 2 to 4 amine groups that are independently protonatable in water, and at least one of those protonatable amine group is protonated to provide the cationic protonated polyamine.
6) The salt of any of embodiments 1-5 and 7-9 wherein the cationic protonated polyamine is a protonated form of a therapeutically effective polyamine that has from 2 to 4 amine groups that are independently protonatable in water, and at least two of those protonatable amine group are protonated to provide the cationic protonated polyamine.
7) The salt of any of embodiments 1-6 and 9 comprising from 1.5 to 2.5 moles of anionic hydrophobic carboxylate for every 1 mole of cationic protonated polyamine.
8) The salt of any of embodiments 1-7 wherein the cationic protonated polyamine is a protonated form of a therapeutically effective polyamine as disclosed herein, for example, a polyamine having the formula (I)

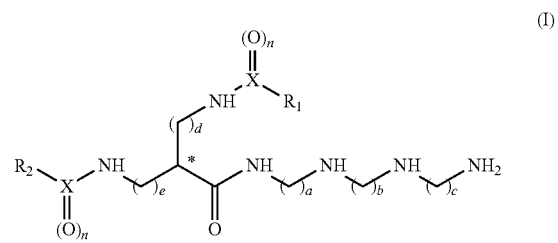

wherein
a, b, and c independently range from 1 to 10;
d and e independently range from 0 to 30;
each X is independently either a carbon (C) or sulfur (S) atom;
R$_1$ and R$_2$ are independently selected from H or from the group of
a straight or branched C$_{1-50}$ saturated or unsaturated aliphatic,
carboxyalkyl, carbalkoxyalkyl, or alkoxy;
a C$_{1-8}$ alicyclic;
a single or multiring aryl substituted or unsubstituted aliphatic;
an aliphatic-substituted or unsubstituted single or multiring aromatic;
a single or multiring heterocyclic;
a single or multiring heterocyclic aliphatic;
a C$_{1-10}$ alkyl;
an aryl sulfonyl;
or cyano; or
R$_2$X(O)$_n$— is replaced by H;
wherein * denotes a chiral carbon position; and
wherein if X is C then n is 1; if X is S then n is 2; and if X is C then the XO group may be CH$_2$ such that n is 0.
9) The salt of any of embodiments 1-7 wherein the cationic protonated polyamine is a protonated form of spermidine, for example, spermidine dicaprate.
10) A process for preparing a salt, the process comprising combining an uncharged polyamine pharmaceutical with an uncharged hydrophobic carboxylic acid in a solvent under proton transfer conditions to form a salt of a charged polyamine pharmaceutical and a charged hydrophobic carboxylate, and separating the salt from the solvent.
11) The process of any of embodiments 10 and 12-15 wherein the solvent comprises methanol.
12) The process of any of embodiments 10-11 and 13-15 wherein about 2 moles of the uncharged carboxylic acid are combined with every 1 mole of uncharged polyamine pharmaceutical.
13) The process of any of embodiments 10-12 and 14-15 wherein the uncharged carboxylic acid is added to a solution comprising the solvent and the uncharged polyamine pharmaceutical.
14) The process of any of embodiments 10-13 and 15 wherein the uncharged carboxylic acid is added to a solution comprising the solvent and the uncharged polyamine pharmaceutical, and a salt is thereby formed as a precipitate.
15) The process of any of embodiments 10-14 which is conducted at a temperature of about 25° C.
16) A pharmaceutical composition for oral administration to a subject, the composition comprising a salt of a cationic protonated polyamine pharmaceutical agent and an anionic hydrophobic carboxylate, the composition being suitable for oral administration.
17) The composition of any of embodiments 16 and 18-21 in a solid form.
18) The composition of any of embodiments 16-17 and 19-21 in a solid form selected from a capsule, a tablet, and a pill.
19) The composition of any of embodiments 16-18 and 20-21 in a solid form having an enteric coating.
20) The composition of any of embodiments 16-19 and 21 further comprising one or more of a glidant, disintegrant and filler (also known as a diluent), where starch may optionally serve in one or more of these capacities.
21) The composition of any of embodiments 16-20 further comprising cellulose, where for example, the cellulose may function as a filler and/or a disintegrant in the composition.
22) An oral dosage form comprising a pharmaceutically effective amount of a salt of a cationic protonated polyamine pharmaceutical agent and an anionic hydrophobic carboxylate.
23) The dosage form of any of embodiments 22 and 24-26 comprising from 1.0 to 500 milligrams of the salt.
24) The dosage form of any of embodiments 22-23 and 25-26 in a solid form.
25) The dosage form of any of embodiments 22-24 and 26 further comprising a solid excipient.
26) The dosage form of any of embodiments 22-25 having a weight of 50 mg to 1,000 mg.
27) A method of preparing a pharmaceutical formulation for oral administration, where the formulation comprises a plurality of inert ingredients, the method comprising combining a salt of a cationic protonated polyamine pharmaceutical and an anionic hydrophobic carboxylate with at least one of the plurality of inert ingredients to form a precursor composition.
28) The method of any of embodiments 27 and 29-30 further comprising isolating an amount of from 1.0 to 1,000 mg of the precursor composition so as to provide a suitable amount for formation of an oral dosage form.
29) The method of any of embodiments 27-28 and 30 further comprising isolating a suitable amount from the precursor composition, and compacting the suitable amount to form a compressed solid dosage form.
30) The method of any of embodiments 27-29 further comprising isolating a suitable amount from the precursor composition, compacting the suitable amount to form a compressed solid dosage form, and placing an enteric coating on the compressed solid dosage form.
31) A method of treatment comprising administering to a subject in need thereof, a therapeutically effective amount of pharmaceutical composition comprising a salt of a cationic protonated polyamine pharmaceutical and an anionic hydrophobic carboxylate.
32) The method of any of embodiments 31 and 33-34 wherein the pharmaceutical composition is administered in a solid dosage form to the subject.
33) The method of any of embodiments 31-32 and 34 wherein the subject is being treated for cancer.
34) The method of any of embodiments 31-33 wherein the salt is administered in conjunction with the administration of difluoromethylornithine (DFMO) to the patient.
35) AMXT 1501 dicaprate, e.g., being a salt formed from components having molecular formulae and structures shown below:

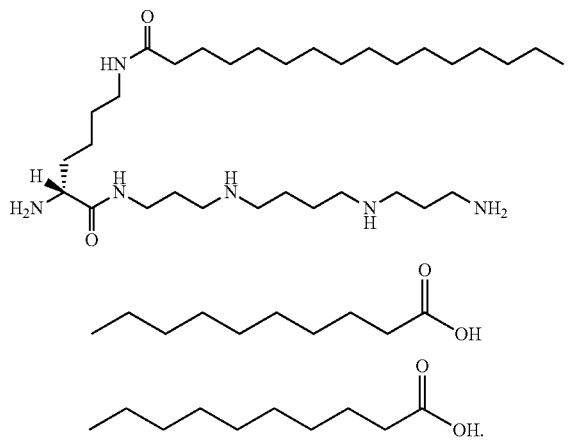

36) AMXT 1569 dicaprate, e.g., being a salt formed from components having molecular formulae and structures shown below:

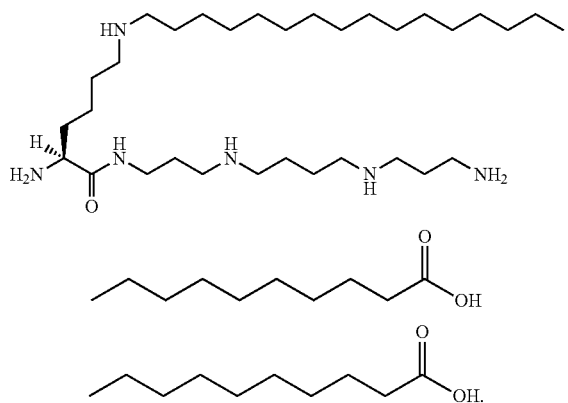

37) AMXT 2030 dicaprate, e.g., being a salt formed from components having molecular formulae and structures shown below:

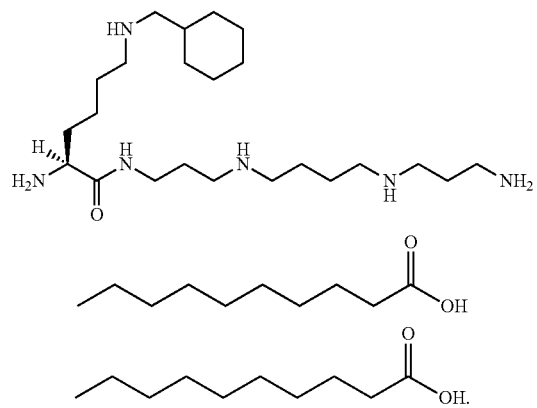

38) AMXT 1426 dicaprate, e.g., being a salt formed from components having molecular formulae and structures shown below:

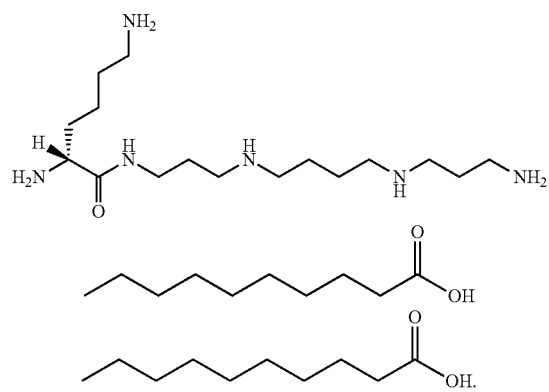

39) Spermidine dicaprate, e.g., being a salt formed from components having the molecular formulae and structures shown below:

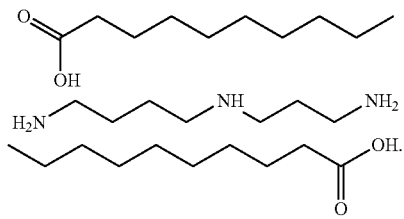

40) A process for preparing a salt, the process comprising combining an uncharged polyamine pharmaceutical with an uncharged hydrophobic carboxylic acid in a solvent such as methanol under proton transfer conditions to form a solution of a salt of a charged polyamine pharmaceutical and a charged hydrophobic carboxylate, where the process further comprises adding a non-solvent such as acetonitrile to the solution and forming a precipitate comprising the salt.

As some specific embodiments, the present disclosure provides a salt of a cationic protonated polyamine pharmaceutical agent and an anionic form of a hydrophobic carboxylic acid, wherein the anionic hydrophobic carboxylic acid is a carboxylate form of a fatty acid selected from octanoic acid, decanoic acid, dodecanoic acid and tetradecanoic acid; the cationic protonated polyamine pharmaceutical agent is a protonated form of a therapeutically effective polyamine excluding peptides and proteins; and the cationic protonated polyamine pharmaceutical agent has from 2 to 4 amine groups and at least one of those protonatable amine groups is protonated to provide the cationic protonated polyamine pharmaceutical agent. Optionally, the salt has two moles of anionic hydrophobic carboxylate for each one mole of cationic protonated polyamine pharmaceutical agent, e.g., the cationic protonated polyamine pharmaceutical agent is a protonated form of a polyamine of formula (I) and the anionic hydrophobic carboxylate is a carboxylate form of a fatty acid selected from decanoic acid and dodecanoic acid. Optionally, the cationic protonated polyamine pharmaceutical agent is a di-protonated form of a polyamine of formula AMXT 1501 and the anionic hydrophobic carboxylate is deprotonated capric acid, and the salt has two moles of deprotonated capric acid for each one mole of protonated AMXT 1501. For instance, the salt has the structure

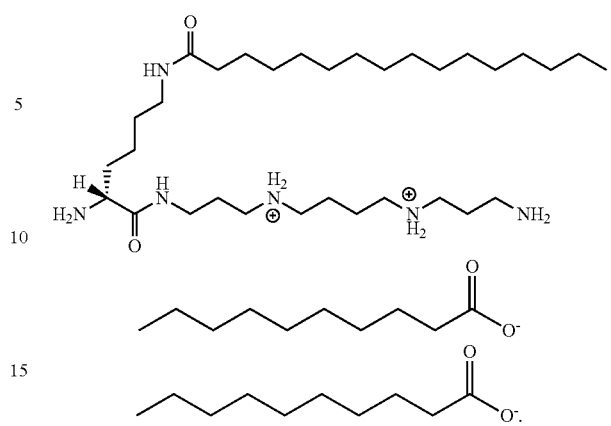

Also optionally, the salt is not in admixture with more than 5 wt % of any other solid or liquid chemical. In addition, the present disclosure provides a pharmaceutical composition comprising such a salt, where the composition may be, e.g., a solid oral dosage form. The present disclosure also provides a method of making such a salt, the method comprising: combining a polyamine pharmaceutical agent, a hydrophobic carboxylic acid and a solvent so as to provide a solution; and isolating a solid residue from the solution, wherein the solid residue comprises the salt of interest. Suitable solvents include water, methanol or a combination thereof. Optionally, about 1.8-2.2 moles of hydrophobic carboxylic acid are combined with each 1.0 mole of polyamine pharmaceutical agent to provide the salt of interest. The solid residue may be formed by precipitation from the solution. The method may also include formulating the solid residue or a portion thereof into a solid dosage form pharmaceutical. In addition, the present disclosure provides a method of treating a medical condition, e.g., cancer, comprising administering to a subject in need thereof a therapeutically effective amount of such a salt, where optionally the therapeutically effective amount of the salt is administered to the subject as a solid dosage form.

As mentioned previously, one or more, e.g., any two, three, four, five, etc. of the polyamines of formulae (I)-(IV), 1426, 1501, 1505, 1569, 2030, DENSpm, Squalamine, Deoxyspergualin, F14512, Mozobil, Trientine, Gentamicin, Polymyxin B, MGBG, and spermidine are exemplary polyamines which in protonated form may be a protonated polyamine pharmaceutical agent of the present disclosure. Thus, the present disclosure provides that any one or more of these polyamines may be a polyamine in the above listed embodiments. Other molecules having a plurality of amine groups and suitable biological activity may also be used to provide a PPA of the present disclosure.

Thus, in separate and exemplary embodiments, the present disclosure provides compounds of formula $(I):(HCA)_1$; compounds of formula $(I):(HCA)_2$; compounds of formula $(I):(HCA)_3$; compounds of formula $(II):(HCA)_1$; compounds of formula $(II):(HCA)_2$; compounds of formula $(II):(HCA)_3$; compounds of formula $(III):(HCA)_1$; compounds of formula $(III):(HCA)_2$; compounds of formula $(III):(HCA)_3$; compounds of formula $(IV):(HCA)_1$; compounds of formula $(IV):(HCA)_2$; compounds of formula $(IV):(HCA)_3$; AMXT 1426:$(HCA)_1$; AMXT 1426:$(HCA)_2$; AMXT 1426:$(HCA)_3$; AMXT 1501:$(HCA)_1$; AMXT 1501:$(HCA)_2$; AMXT 1501:$(HCA)_3$; AMXT 1505:$(HCA)_1$; AMXT 1505:$(HCA)_2$; AMXT 1505:$(HCA)_3$; AMXT 1569:$(HCA)_1$; AMXT 1569:

(HCA)$_2$; AMXT 1569:(HCA)$_3$; AMXT 2030:(HCA)$_1$; AMXT 2030:(HCA)$_2$; AMXT 2030:(HCA)$_3$; DENSpm:(HCA)$_1$; DENSpm:(HCA)$_2$; DENSpm:(HCA)$_3$; Squalamine:(HCA)$_1$; Squalamine:(HCA)$_2$; Squalamine:(HCA)$_3$; Deoxyspergualin:(HCA)$_1$; Deoxyspergualin:(HCA)$_2$; Deoxyspergualin:(HCA)$_3$; F14512:(HCA)$_1$; F14512:(HCA)$_2$; F14512:(HCA)$_3$; Mozobil:(HCA)$_1$; Mozobil:(HCA)$_2$; Mozobil:(HCA)$_3$; Trientine:(HCA)$_1$; Trientine:(HCA)$_2$; Trientine:(HCA)$_3$; Gentamicin:(HCA)$_1$; Gentamicin:(HCA)$_2$; Gentamicin:(HCA)$_3$; Polymyxin B:(HCA)$_1$; Polymyxin B:(HCA)$_2$; Polymyxin B:(HCA)$_3$; spermine:(HCA)$_1$; spermine:(HCA)$_2$; spermine:(HCA)$_3$; spermidine:(HCA)$_1$; spermidine:(HCA)$_2$; spermidine:(HCA)$_3$; MGBG:(HCA)$_1$; MGBG:(HCA)$_2$; and MGBG:(HCA)$_3$. In each of these embodiments, HCA may be a hydrophobic carboxylic acid as described herein, e.g., a $C_{10-14}$ fatty acid such as capric acid.

It is to be understood that the terminology used herein is for the purpose of describing specific embodiments only and is not intended to be limiting. It is further to be understood that unless specifically defined herein, the terminology used herein is to be given its traditional meaning as known in the relevant art.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

As described herein, for simplicity, a patient, clinician, or another human may in some cases be described in the context of the male gender. It is understood that a medical practitioner can be of any gender, and the terms "he," "his," "himself," and the like as used herein are to be interpreted broadly inclusive of all known gender definitions.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

In the foregoing description, certain specific details are set forth to provide a thorough understanding of various disclosed embodiments. However, one skilled in the relevant art will recognize that embodiments may be practiced without one or more of these specific details, or with other methods, components, materials, etc.

The Examples and preparations provided below further illustrate and exemplify the subject matters of the present invention and methods of preparing such subject matter. It is to be understood that the scope of the present invention is not limited in any way by the scope of the following Examples and preparations. In the following Examples, molecules with a single chiral center, unless otherwise noted, exist as a racemic mixture. Those molecules with two or more chiral centers, unless otherwise noted, can exist as a racemic mixture of diastereomers. Single enantiomers/diastereomers may be obtained by methods known to those skilled in the art. The starting materials and various reactants utilized or referenced in the examples may be obtained from commercial sources, or are readily prepared from commercially available organic compounds, using methods well-known to one skilled in the art.

EXAMPLES

Example 1

Preparation of Free Base Form of AMXT 1501

A 2 L round-bottomed flask was charged with 724.2 g of Amberlyst™ A25 hydroxide anion-exchange resin (Dow Chemical, Midland, Mich., USA) and 1 liter of methanol. The mixture was stirred with a magnetic stir bar at ambient temperature for about 10 minutes, and then the resin was filtered using a Büchner funnel. The cleaned resin was transferred into a beaker until it was ready for use. A clean 2 L round-bottomed flask was charged with 57.9 g (81.0 mmole) of the hydrochloride salt of AMXT 1501 (Aminex Therapeutics, Inc., Kirkland, Wash., USA) and 2 liters of methanol. The mixture was stirred with a magnetic stir bar at ambient temperature for about 1 hour to yield a turbid solution. The turbid solution was transferred to a 5 L vessel and the washed Amberlyst™ A25 resin was added. The mixture was stirred for 10 minutes at ambient temperature, during which time the solution became milky white and then became clear. After an additional 10-20 minutes of stirring, the mixture is filtered to collect the resin. The resin was washed several times with a total of about 1 liter of methanol. The filtrate and washings were combined to provide about 3.1 liter of solution. The solution was placed on a roto-evaporator under reduced pressure and the solvent was removed at about 30° C. to leave behind a white solid. Additional drying under full dynamic vacuum provided 42.18 g (91.5% yield) of dry white solid as the free base form of AMXT 1501, which was scraped from the vessel.

Example 2

Preparation of AMXT 1501 Dicaprate Salt

A 250 ml flask was charged with 10 g (17.6 mmole) of AMXT 1501 free base as prepared in Example 1, 6.0 g (34.8 mmole, 2.0 eq.) of capric acid (Aldrich Chemicals) and 100 ml of methanol. The mixture was stirred with a magnetic spin bar at ambient temperature for about 5 minutes until a homogeneous solution formed. The solution was stirred for an additional 30 minutes, then the stirring was stopped and the solvent was evaporated under reduced pressure at 30° C. to provide an off-white solid residue. This residue was dried under full dynamic vacuum for 12-15 hours at ambient temperature and then scrapped out of the reaction flask to provide the titled salt in about 97% yield.

The titled salt was characterized by elemental analysis, and matched the theoretical with the inclusion of ½ mole of water (H$_2$O). Elemental analysis calculated for C$_{52}$H$_{110}$N$_6$O$_7$+½H$_2$O=C, 67.49; H, 11.91; N, 9.08; 0, 11.52. Found C, 67.65; H, 11.85; N, 8.75; 0, 11.58. Karl Fischer water titration showed 1.3% H$_2$O associated with the titled salt. The molecular weight ratio of ½H$_2$O to AMXT 1501 dicaprate=9.2/913.47=0.986%. Thermogravimetric analysis (TGA) showed the loss of 1.073% weight at 100 to 135'C.

Figure 2:
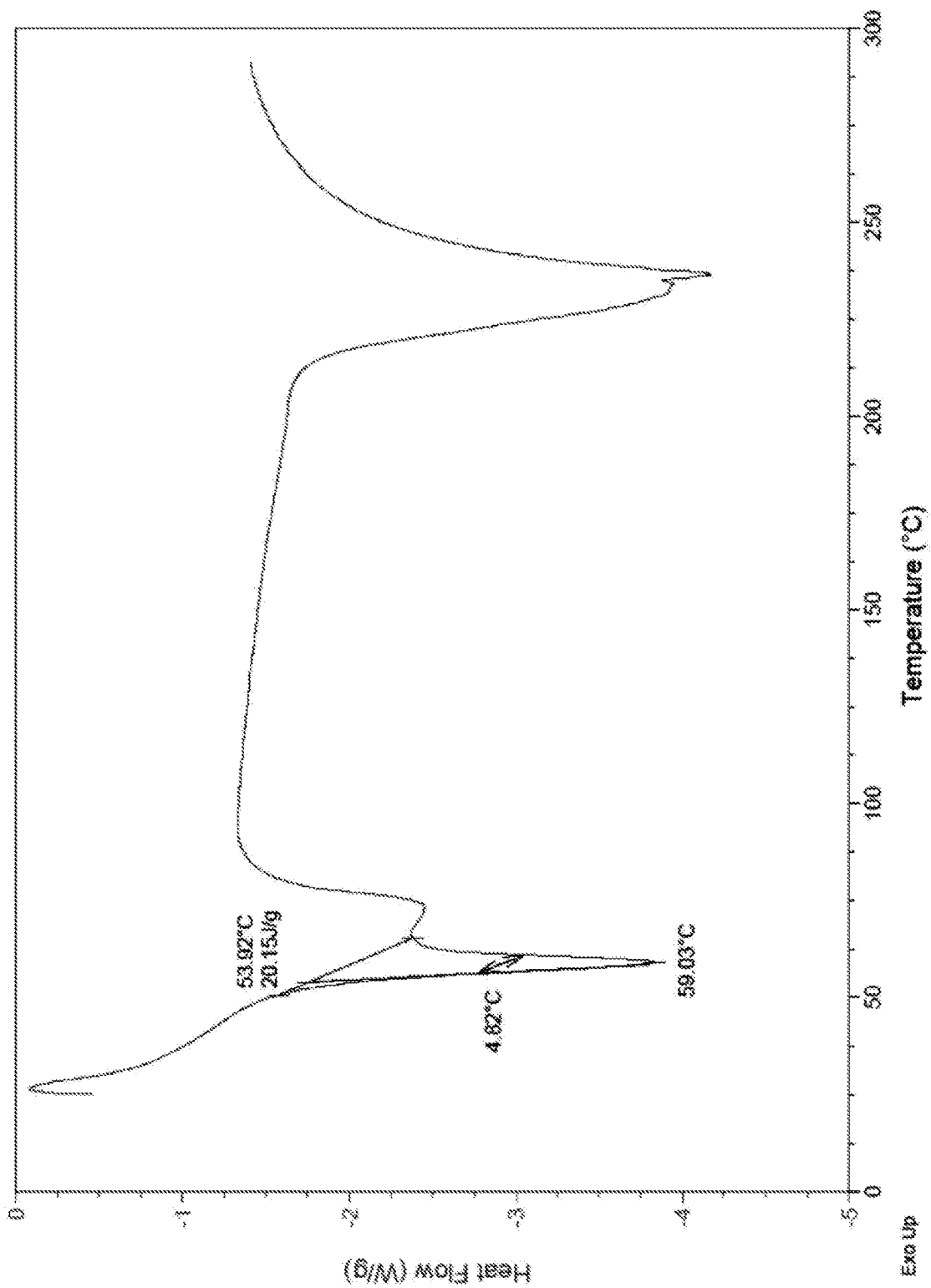
FIG. 2 shows a DSC scan for AMXT 1501 dicaprate, a salt of the present disclosure.
Figure 3:
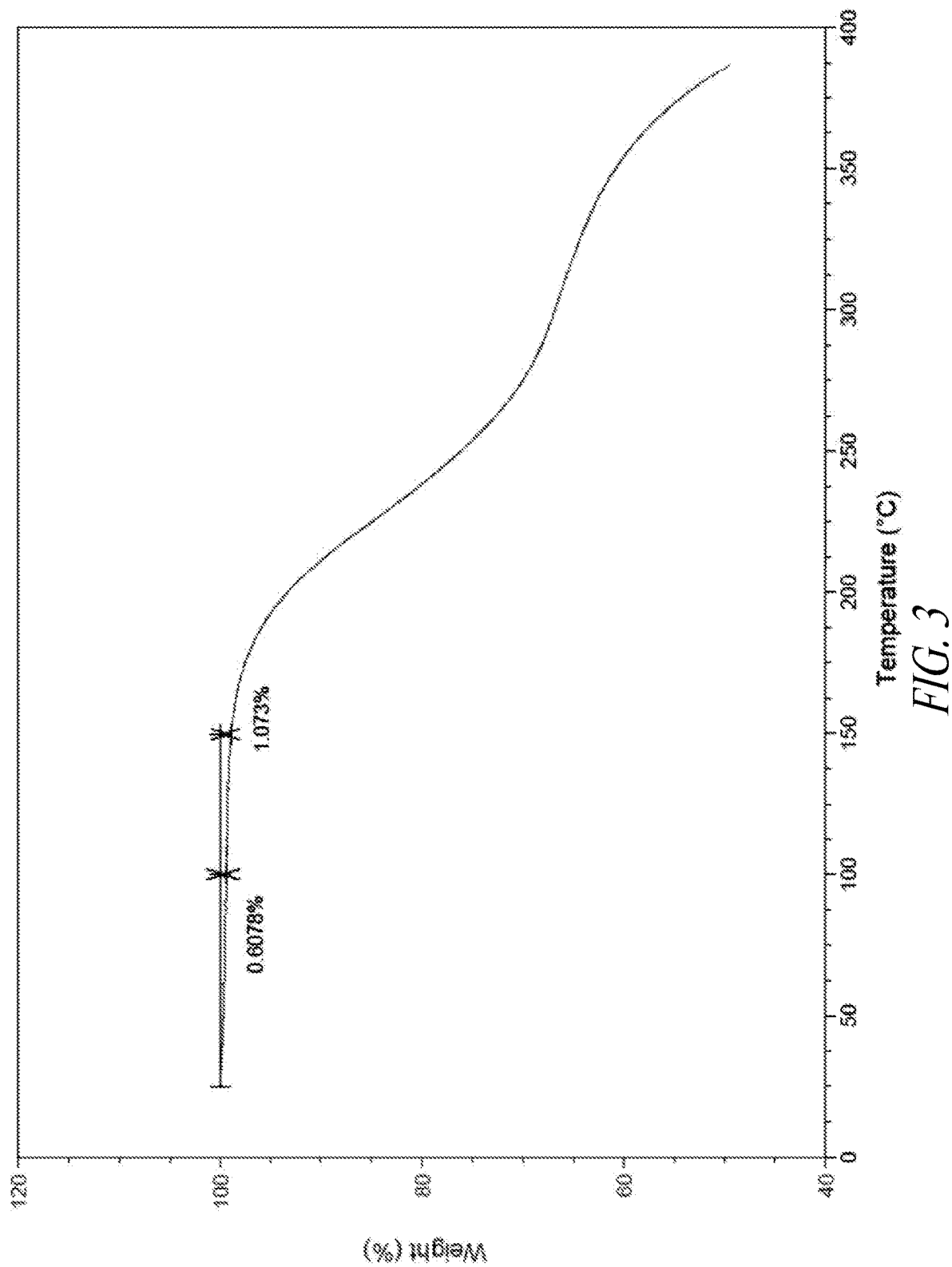
FIG. 3 shows a TGA scan for AMXT 1501 dicaprate, a salt of the present disclosure.

Differential Scanning Calorimetry (DSC) was performed on the titled salt, resulting in the DSC scan shown in FIG. 2 and the Thermogravimetric Analysis (TGA) scan shown in FIG. 3.

As another option, a non-solvent can be added to a solution formed upon mixing the free base form of a polyamine (e.g., the free base form of AMXT 1501) and a hydrophobic carboxylic acid (e.g., two molar equivalents of capric acid) in a solvent which dissolves the resulting salt. The addition of the non-solvent will cause a precipitation of the resulting salt, where the precipitate may be separated from the non-solvent by, e.g., decantation or filtration. This method is exemplified by the following method. To a clear solution formed by dissolving 283.2 g of AMXT 1501 free base in 455 mL methanol is added 171.5 g of capric acid (2 equivalents), resulting in an approximate 1 g/mL solution of salt composition. This solution is cooled in an ice bath and 3.7 L of acetonitrile is added slowly to the solution over a 1 to 2 hour period. When about 30% of the total acetonitrile charge has been added, the solution becomes cloudy, followed by the precipitation of a white solid product. The resulting thick slurry is filtered and the resulting white powder is washed with acetonitrile and dried overnight to give 403.9 g (79%) of AMXT 1501 dicaprate as a white powder.

Example 3

Tablet of AMXT 1501 Dicaprate Salt

A 200 ml round-bottomed flask was charged with 38.4 g of the dicapric salt of AMXT 1501 from Example 2, 28.5 g of Starcap™ 1500 starch (Colorcon, Harleysville, Pa., USA), 8.4 g of sodium cross carmellose (FMC, Philadelphia, Pa., USA), 42.3 g Avicel™ PH-102 microcrystalline cellulose (FMC, Philadelphia, Pa., USA) and 1.2 g Aerosil™ R202 fumed silica (Evonik Corp., Piscataway, N.J., USA). This mixture was briskly shaken for a few seconds, then it was placed on a roller assembly where the blend was rolled at high speed for 30 minutes. After this rolling was completed, 1.2 g of magnesium stearate (Spectrum Chemicals, Tucson, Ariz., USA) was added and the mixture shaken briskly for a few seconds followed by rolling for one minute. The rolled mixture was then loaded into the feeder of a tablet press and pressed into the form of a tablet by applying a pressure of about 1.5 tons. The tablet size was 10 mm hexagon shape and the average weight per tablet was 0.4 g. The tablets had a hardness of 18-20 kp, a disintegration time of less than 15 minutes.

Example 4

Enterically Coated Tablet of Capric Salt of AMXT 1501

A tared 500 ml beaker was equipped with an overhead stirrer and was charged with 340 g of distilled water. The water was stirred until a vortex appeared. To the rapidly stirring water was added 40 g of Opadry™ hydroxyl propylmethyl cellulose (HPMC, Colorcon) over a period of about 2 minutes. Stirring was continued for about 1 hour, during which time a homogeneous semi-viscous opaque solution formed. Water (60 g) was then added with stirring, followed by an additional 60 minutes of stirring. No particles or agglomerated solids were visible. The stirring was stopped and the beaker and contents were refrigerated at 5° C. overnight to provide the clear coat coating solution.

A tared 2 L beaker equipped with an overhead stirrer was charged with 600 g of distilled water. The water was stirred until a vortex formed. To this rapidly stirring water was added 200 g of Acryl-EZE™ enteric coating (Colorcon) over a period of about 2 minutes, followed by 60 minutes of additional stirring to provide a homogenous white suspension. To the white suspension was added 200 g of water followed by 5 minutes of additional stirring. The suspension was then left overnight at 5° C. Prior to use, the suspension was removed from the refrigerator and allowed to warm up to room temperature so as to provide the Acryl-EZE enteric coating solution.

A Freund Hi-Coater Model HCT-30 with a Freund spray nozzle was used to prepare the enterically coated tables. 500 g of placebo tablets were placed on the pan of the Freund coater, and the heater and fan of the coater were turned on. The coater was set at an intake temperature of 88° C., a bed temperature of 37.5° C., and a pan rotation speed of 14 rpm. After these conditions were met, which took 20-30 minutes, 94.7 g of tablets (about 234 tablets of different shape than the placebo tablets above) of the dicapric salt of AMXT 1501 as prepared in Example 3 were added to the pan. Onto the rotating and cascading tablets in the pan, the clear coat solution (HPMC) was sprayed at a pressure of 1.2 kg/cm$^3$ and a rate of 2.0 g/min for a first 20 minutes. After this first 20 minutes, the spray rate was increased to 2.6 g/min. Spraying was continued until an average tablet weight gain of 2% solids, at which point the spraying was discontinued and rolling and heating were maintained for about 2 minutes. About 111 g of clear coat solution was used. The resulting tablet mixture were white with a slight shine.

These white, slightly shiny tablets were then exposed to the enteric coating solution (Acryl-EZE enteric coating). The coater was primed with the enteric coating solution, then set to achieve an intake temperature of 88° C. and a bed temperature of 38° C. When these conditions were met, the pan was made to rotate at 14 rpm. To the rotating tablets was sprayed the enteric coating solution at a pressure of 1.2 kg/cm$^3$ and a rate of 2.6 g/min. Spraying was continued until an average weight gain of 8-10% solids was achieved. About 665 g of enteric coating solution was used to provide 234 enterically coated tablets of the capric salt of AMXT 1501 following separation from the placebo tablets.

Example 5

Solubility Analysis of AMXT 1501 Dicaprate Salt

Twenty-three 2 ml centrifuge tubes with caps were each charged with at least 10 mg of the dicapric salt of AMXT 1501 as prepared in Example 2. Each vial was labeled with a test solvent as identified in the Table. After labeling, to each vial was added 2.0 ml of the indicated solvent, with the exception of the lanolin alcohol labeled vial, which received 1.8 g of solid lanolin alcohol.

After addition of the solvents was completed, the vials were sonicated in a sonication bath set at 45° C. for about 60 minutes. The vial containing lanolin alcohol was placed in a hot water bath set at 85° C. and heated in this bath for about 30 minutes prior to being placed in the sonicator. After heating for about 60 minutes, all samples were removed from the heat sources and permitted to cool to ambient temperature over a period of one hour.

After cooling, the samples were prepared for analysis by first centrifuging the samples in the vials. After centrifugation, the samples were diluted 1 to 10 in an HPLC vial with 0.1% trifluoroacetic acid (TFA) in acetonitrile. In some cases, an additional 1 to 10 dilution was needed if the HPLC response was off scale. The results of the solubility analysis are shown in Table 1.

TABLE 1

| Test Solvent | Solubility |
| --- | --- |
| Distilled water | ≥10 mg/ml* |
| Aq. HCl, pH 3 | ≥10 mg/ml* |
| Ethanol | ≥10 mg/ml* |
| Methanol | ≥10 mg/ml* |
| Isopropyl alcohol | ≥10 mg/ml* |
| Glycerol | ≥10 mg/ml* |
| Propylene glycol | ≥10 mg/ml* |
| TWEEN 20 | ≥10 mg/ml* |
| TWEEN 80 | ≥10 mg/ml* |
| PEG 400 | ≥10 mg/ml* |
| Dimethyl formamide | ≥10 mg/ml* |
| Dimethyl sulfoxide | ≥10 mg/ml* |
| Tetrahydrofuran | ≥10 mg/ml* |
| Diethyl glycol MME | ≥10 mg/ml* |
| Hexane | Not soluble |
| Methylene chloride | ≥10 mg/ml* |
| Ethyl acetate | 0.68 mg/ml |
| Toluene | 2.6 mg/ml |
| Vitamin E oil | ≥10 mg/ml* |
| Lanolin alcohol | ≥10 mg/ml* |
| Lecithin | ≥10 mg/ml* |
| Isopropyl myristate | Reacted with API |

Longer-term solubility was determined by evaluating the samples 24 hours after preparation. The results from the longer-term study are provided in Table 2.

TABLE 2

| Test Solvent | Solubility |
| --- | --- |
| Distilled water | ≥10 mg/ml* |
| Aq. HCl, pH 3 | ≥10 mg/ml* |
| Ethanol | ≥10 mg/ml* |
| Methanol | ≥10 mg/ml* |
| Isopropyl alcohol | ≥10 mg/ml* |
| Glycerol | ≥10 mg/ml* |
| Propylene glycol | ≥10 mg/ml* |
| TWEEN 20 | ≥10 mg/ml* |
| TWEEN 80 | ≥10 mg/ml* |
| PEG 400 | ≥10 mg/ml* |
| Dimethyl formamide | ≥10 mg/ml* |
| Dimethyl sulfoxide | ≥10 mg/ml* |
| Tetrahydrofuran | ≥10 mg/ml* |
| Diethyl glycol MME | ≥10 mg/ml* |
| Hexane | Not soluble |
| Methylene chloride | ≥10 mg/ml* |
| Ethyl acetate | 0.62 mg/ml |
| Toluene | 2.7 mg/ml |
| Vitamin E oil | ≥10 mg/ml* |
| Lanolin alcohol | ≥10 mg/ml* |
| Lecithin | ≥10 mg/ml* |
| Isopropyl myristate | Reacted with API |

The capric acid salt prepared in Example 2 had a solubility of greater than 10 mg/ml in most of the solvents tested. The lowest solubility was found in hexane where by HPLC analysis no material was detected. The capric acid salt also had low solubility in ethyl acetate and toluene.

Example 6

Preparation and Characterization of the Mono-, Di-, Tri- and Tetra-Caprate Salt Forms of AMXT 1501

A 50 gram sample of AMXT 15014HCl salt was converted in methanol to the free base using Dow Amberlyst™ A26 OH resin as described in Example 1. The solvent was removed on the rotovap to give the free base as a solid in an 88% yield. The free base was analyzed by HPLC to give an assay of 97% using the HCl salt as a reference and correcting for the molecular weight.

To prepare the 1, 2, 3, and 4× salts, 5 grams of the free base above and the appropriate amount of capric acid was combined and dissolved in methanol. The methanol from each salt was removed using the rotory evaporator. The resulting solids were dried in the vacuum oven at room temperature.

Solubility. During the preparation section above, it was observed when the residue in the round bottom from each of the salts was washed out there was a clear progression of the mono- and dicaprate salts being much more water soluble than the tri- and tetra-AMXT 1501 caprate salts. To test the solubility, a known portion of each salt was added to 1 ml of DI water. The solutions were vortexed and sonicated sometimes several times and observed for solubility. In addition to the 4 salts that were prepared in the same manner and at the same time, a sample of the 2× caprate salt with AMXT 1501 that was precipitated from methanol using acetonitrile was also evaluated to determine if there was any observed solubility differences between this 2× salt and the one isolated through a simple removal of the methanol solvent. The results are summarized in Table 3. The mono- and di-caprate salts showed a significantly higher solubility in water than the tri- and tetra-caprate salts.

TABLE 3

Solubility of various ratios of AMXT 1501 Caprate Salts in $H_2O$

| Sample | Salt Ratio | Solubility |
| --- | --- | --- |
| Monocaprate | 1x | >150 mg/ml |
| Dicaprate | 2x | >150 mg/ml |
| Tricaprate | 3x | <10 mg/ml |
| Tetracaprate | 4x | <10 mg/ml |
| Dicaprate (Isolated from MeOH/ACN) | 2x | >150 mg/ml |

TGA Analysis. Five AMXT 1501 capric salt ratio samples were analyzed by TGA and heated at a rate of 20° C. per minutes to a final temperature of 400° C. The TGAs were processed by first showing the percent weight drop from the starting point to 100° C., which could give an indication of the water content, and then the weight drop to the first plateau. Table 4 shows the data for each sample.

TABLE 4

TGA of AMXT 1501 Capric Salts

| Sample | Capric Salt | % loss to 100° C. | % loss to next plateau (temperature of plateau) |
| --- | --- | --- | --- |
| Monocaprate | 1x | 0.3038% | 18.56% (250° C.) |
| Dicaprate | 2x | 0.6179% | 32.40% (288° C.) |

TABLE 4-continued

TGA of AMXT 1501 Capric Salts

| Sample | Capric Salt | % loss to 100° C. | % loss to next plateau (temperature of plateau) |
|---|---|---|---|
| Tricaprate | 3x | 0.2165% | 38.36% (275° C.) |
| Tetracaprate | 4x | 0.1496% | 42.41% (275° C.) |
| Dicaprate (isolated from MeOH/ACN) | 2x | 0.8699% | 30.98% (288° C.) |

DSC Analysis. The salt ratio samples that were analyzed above by TGA were also analyzed by DSC. All of the samples were heated at a rate of 20° C./minute up to a final temperature of 200° C. The DSC analysis looked for the presence of any glass transitions, melting points and the melting point range at half height to determine purity of the sample. Target range of half height is about 5° C. Table 5 shows the melting points of the sample and melting range at half height. There were no observed glass transitions for any of the samples.

TABLE 5

DSC of Capric Salts

| Sample | Capric Salt | Melting Point | Melting range at half height |
|---|---|---|---|
| Monocaprate | 1x | 83.75° C. | 4.92° C. |
| Dicaprate | 2x | 59.19° C. | 3.98° C.* |
| Tricaprate | 3x | 56.99° C. | 5.56° C. |
| Tetracaprate | 4x | 58.87° C. | 3.91° C. |
| Dicaprate (Isolated from MeOH/ACN) | 2x | 61.59° C. | 7.17° C. |

*This sample had at least one more melting point at 72.31° C.

Characterization of the salts by FT-IR. The same samples above were analyzed by FT-IR using a diamond ATR sampling unit. Table 6 lists some of the bands that are present in all of the IR scans. The overall signals appear to become weaker as capric substitution increases.

TABLE 6

FT-IR Analysis Characteristics of AMXT 1501 Caprate Salts

| Cm$^{-1}$ | Description |
|---|---|
| 1550-1650 | Carboxylate ion and amides (capric and AMXT 1501) |
| 3000-2840 | CH bands from normal alkanes (capric and AMXT 1501) |
| 3330-3060 | NH bands and amine salts (AMXT 1501) |

Determination of residual water by KF. The water content of the samples was determined by KF titration. Table 7 shows the average water content and the number of samples used for the average.

TABLE 7

Water Content of AMXT 1501 Caprate Salt Samples

| Sample | Capric Salt | Percent water (Number of runs used for average) |
|---|---|---|
| Monocaprate | 1x | 0.51% (4) |
| Dicaprate | 2x | 0.68% (3) |
| Tricaprate | 3x | 0.47% (2) |
| Tetracaprate | 4x | 0.23% (2) |

TABLE 7-continued

Water Content of AMXT 1501 Caprate Salt Samples

| Sample | Capric Salt | Percent water (Number of runs used for average) |
|---|---|---|
| Dicaprate (Isolated from MeOH/ACN) | 2x | 1.05% (2) |

Elemental Analysis. The four samples prepared were sent for C, H, N and O analysis. The theory percentage of the elements were determined using the following formulas shown in Table 8. The calculated and found values are shown below in Tables 9 to 12. Variability in the results from the calculated and found are likely due to hydrates or a slight variation in the equivalents of the capric acid that was added to the free base to produce each salt substitution. As capric acid to AMXT 1501 free base ratio increases water solubility decreases. The mono- and dicaprate AMXT 1501 salts showed good solubility at a concentration of >150 mg/ml whereas the solubility of the tri- and tetracaprate AMXT 1501 salts were very low at <10 mg/ml.

TABLE 8

Theoretical Formulas for AMXT 1501 Capric Salts

| Sample | Capric Salt | Theory Formula |
|---|---|---|
| Monocaprate | 1x | $C_{42}H_{88}N_6O_4$ |
| Dicaprate | 2x | $C_{52}H_{108}N_6O_6$ |
| Tricaprate | 3x | $C_{62}H_{128}N_6O_8$ |
| Tetracaprate | 4x | $C_{72}H_{148}N_6O_{10}$ |

TABLE 9

Elemental Analysis for AMXT 1501 Monocaprate Salt

| Monocaprate | Calculated | Found (% Difference) |
|---|---|---|
| Carbon | 68.1% | 67.60% (0.5%) |
| Hydrogen | 12.0% | 11.22% (0.78) |
| Nitrogen | 11.3% | 11.33% (0.03%) |
| Oxygen | 8.6% | 8.66% (0.06%) |

TABLE 10

Elemental Analysis for AMXT 1501 Dicaprate Salt

| Dicaprate | Calculated | Found (% Difference) |
|---|---|---|
| Carbon | 68.4% | 67.94% (0.46%) |
| Hydrogen | 11.9% | 12.07% (0.17%) |
| Nitrogen | 9.2% | 9.13% (0.07%) |
| Oxygen | 10.5% | 11.17% (0.67%) |

TABLE 11

Elemental Analysis for AMXT 1501 Tricaprate Salt

| Tricaprate | Calculated | Found (% Difference) |
|---|---|---|
| Carbon | 68.6% | 68.42% (0.18%) |
| Hydrogen | 11.9% | 11.79% (0.11%) |
| Nitrogen | 7.7% | 7.78% (0.08%) |
| Oxygen | 11.8% | 12.38% (0.58%) |

TABLE 12

Elemental Analysis for AMXT 1501 Tetracaprate Salt

| Tetracaprate | Calculated | Found (% Difference) |
|---|---|---|
| Carbon | 68.7% | 69.26% (0.56%) |
| Hydrogen | 11.9% | 12.31% (0.41%) |
| Nitrogen | 6.7% | 6.82% (0.12%) |
| Oxygen | 12.7% | 13.03% (0.33%) |

Using TGA analysis, all salts showed various amounts of weight loss up to 100° C. likely due to different amounts of water of hydrations. The next plateau of weight loss to approximately the same final temperature showed an increase in weight loss as substitution increased which is likely due to loss of the capric salt substitution as the sample is heated. The DSC analysis showed no definitive glass transition points suggesting that the materials are mostly crystalline. The melting point of the mono-caprate AMXT 1501 salt was the highest, and the di-, tri- and tetra-caprate AMXT 1501 salts were lower with approximately the same melting point. All of the samples gave the same characteristic bands for the functional groups by FT-IR, however the bands appear to be weaker as the capric acid to AMXT 1501 ratio increases. Water analysis by Karl Fischer titration showed the highest water content with the mono- and dicaprate AMXT 1501 salts and a lower water content with the tri- and tetra-AMXT 1501 salts. Elemental analysis shows reasonable agreement with theory and follows the theory trends for C, H, N and O analysis.

Example 7

Pharmacokinetic Analysis of Various AMXT 1501 HCA Salts Delivered Orally in Beagle Dogs Following an acclimation of five (5) days, 12 beagle dogs were divided into four groups of three dogs per group, and were dosed with two tablets with the assigned compound or salt. Following dose administration all the animals had serial blood collections. The experimental design for the study is provided in Table 13.

TABLE 13

Experimental Study Design

| Group | Animals per Group | Dose Route | AMXT 1501 Salt Form | 1501 Dose Level mg/kg | 1501 Dose Conc. mg/tablet | Dose Volume No. of Tablets |
|---|---|---|---|---|---|---|
| 1 | 3 (1M/2F) | PO | Free base | 16.0 | 80 | 2 |
| 2 | 3 (2M/1F) | PO | Dicholate | 16.0 | 80 | 2 |
| 3 | 3 (1M/2F) | PO | Phosphate | 16.0 | 80 | 2 |
| 4 | 3 (2M/1F) | PO | Dicaprate | 16.0 | 80 | 2 |

Tablet formulation information is provided in Tables 14, 15, 16 and 17.

TABLE 14

Formulation for AMXT 1501 Free Base

| Excipient Name | Weight % | Weight (mg) |
|---|---|---|
| AMXT 1501 Free Base | 20.00 | 80.0 |
| Starch 1500 | 28.50 | 114.0 |
| Cross Carmelose | 7.00 | 28.0 |
| Microcrystalline cellulose (Avicel PH 102) | 42.50 | 170.0 |
| Fumed Silica | 1.00 | 4.0 |
| Magnesium Stearate | 1.00 | 4.0 |
| Total | 100.00 | 400.0 |

TABLE 15

Formulation for AMXT 1501 Dicholate Salt

| Excipient Name | Weight % | Weight (mg) |
|---|---|---|
| AMXT 1501 Cholate Salt (58.2% active) | 34.38 | 137.5 |
| Phospholipon 90H | 2.50 | 10.0 |
| Starch 1500 | 21.63 | 86.5 |
| Cross Carmelose | 7.00 | 28.0 |
| Microcrystalline cellulose (Avicel PH 102) | 32.50 | 130.0 |
| Fumed Silica | 1.00 | 4.0 |
| Magnesium Stearate | 1.00 | 4.0 |
| Total | 100.00 | 400.0 |

TABLE 16

Formulation for AMXT 1501 Phosphate Salt

| Excipient Name | Weight % | Weight (mg) |
|---|---|---|
| AMXT 1501 Phosphate Salt (74.7% Active) | 26.78 | 107.1 |
| Starch 1500 | 25.48 | 101.9 |
| Cross Carmelose | 7.00 | 28.0 |
| Microcrystalline cellulose (Avicel PH 102) | 38.75 | 155.0 |
| Fumed Silica | 1.00 | 4.0 |
| Magnesium Stearate | 1.00 | 4.0 |
| Total | 100.00 | 400.0 |

TABLE 17

Formulation for AMXT Dicaprate Salt

| Excipient Name | Weight % | Weight (mg) |
|---|---|---|
| AMXT 1501 2x Capric Salt (62.5% Active) | 32.00 | 128.0 |
| Starch 1500 | 23.75 | 95.0 |
| Cross Carmelose | 7.00 | 28.0 |
| Microcrystalline cellulose (Avicel PH 102) | 35.25 | 141.0 |
| Fumed Silica | 1.00 | 4.0 |
| Magnesium Stearate | 1.00 | 4.0 |
| Total | 100.00 | 400.0 |

Table 18 provides pharmacokinetic data obtained using the various salt forms of AMXT 1501 following single PO dosing to dogs. In Table 18, Group 1 received the free base form of AMXT 1501, Group 2 received the dicholate salt of AMXT 1501, Group 3 received the phosphate salt form of AMXT 1501, and Group 4 received the dicaprate salt form of AMXT 1501. Also in Table 18, $T_{max}$ is reported in units of hour, where $T_{max}$ is defined as the time after dosing at which the maximum plasma concentration of AMXT 1501 is reached, $C_{max}$ is reported in units of ng/mL, where $C_{max}$ is defined as the maximum concentration of AMXT 1501 observed in the plasma, $AUC_{0-t}$ is reported in units of hour*ng/mL, and is defined as the area under the curve in a graph of plasma concentration as a function of time to the time of 24 hours (i.e., t=24 hours), and $t_{1/2}$ is reported in units of hour, where $t_{1/2}$ is defined as the time after dosing at which the plasma concentration of AMXT 1501 reaches half of its maximum concentration. In Table 18, SD refers to standard deviation and CV % refers to coefficient of variability.

TABLE 18

Pharmacokinetic Data

| Group ID | Parameter | N | Mean | SD | Min | Median | Max | CV % |
|---|---|---|---|---|---|---|---|---|
| Group 1 | $T_{max}$ | 3 | 8.00 | 3.46 | 6.00 | 6.00 | 12.0 | 43.3 |
|  | $C_{max}$ | 3 | 250 | 218 | 31.3 | 250 | 468 | 87.4 |
|  | $AUC_{0-t}$ | 3 | 4710 | 4080 | 363 | 5330 | 8450 | 86.5 |
|  | $t_{1/2}$ | 1 | 9.76 | N.D. (n = 1) | 9.76 | 9.76 | 9.76 | N.D. (n = 1) |
| Group 2 | $T_{max}$ | 3 | 6.00 | 0.00 | 6.00 | 6.00 | 6.00 | 0.0 |
|  | $C_{max}$ | 3 | 297 | 154 | 182 | 237 | 472 | 51.9 |
|  | $AUC_{0-t}$ | 3 | 6650 | 3160 | 4780 | 4870 | 10300 | 47.5 |
|  | $t_{1/2}$ | 3 | 13.2 | 0.822 | 12.2 | 13.6 | 13.7 | 6.2 |
| Group 3 | $T_{max}$ | 3 | 6.00 | 0.00 | 6.00 | 6.00 | 6.00 | 0.0 |
|  | $C_{max}$ | 3 | 115 | 115 | 19.5 | 82.8 | 242 | 99.9 |
|  | $AUC_{0-t}$ | 3 | 3280 | 4320 | 256 | 1350 | 8230 | 131.8 |
|  | $t_{1/2}$ | 2 | 15.5 | 12.6 | 6.57 | 15.5 | 24.4 | 81.3 |
| Group 4 | $T_{max}$ | 3 | 6.00 | 0.00 | 6.00 | 6.00 | 6.00 | 0.0 |
|  | $C_{max}$ | 3 | 276 | 74.0 | 201 | 278 | 349 | 26.8 |
|  | $AUC_{0-t}$ | 3 | 6580 | 1980 | 4710 | 6370 | 8640 | 30.0 |
|  | $t_{1/2}$ | 3 | 14.0 | 1.98 | 12.4 | 13.4 | 16.2 | 14.2 |

Figure 4A:
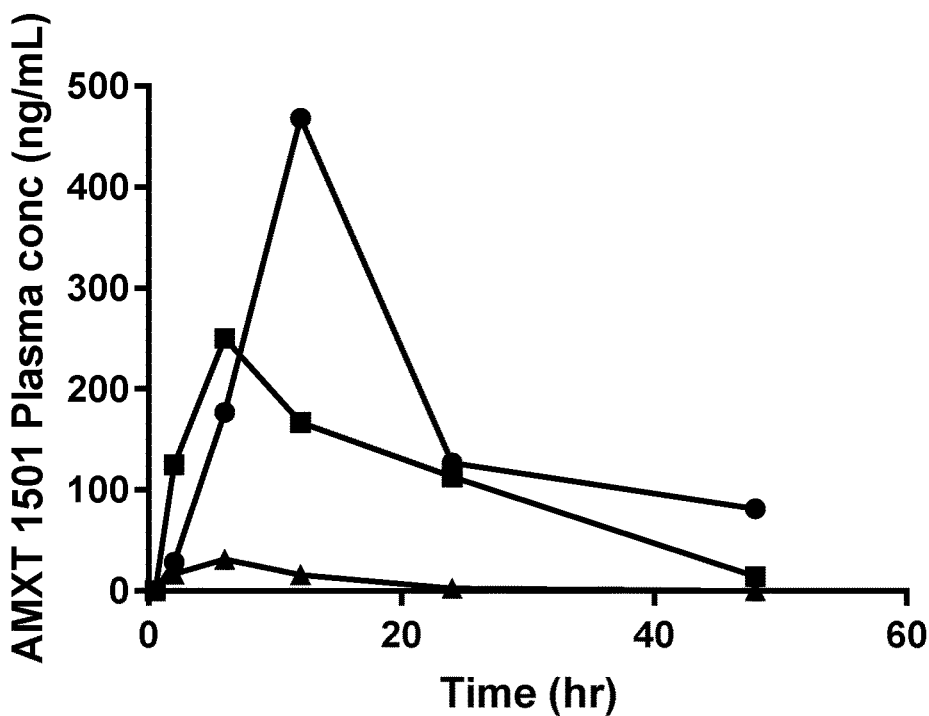
FIGS. 4A, 4B, 4C and 4D show individual animal plasma levels of AMXT 1501 following single oral dosing of AMXT 1501 free base (FIG. 4A) and various salt forms of AMXT 1501 (FIGS. 4B (Dicholate), 4C (Phosphate) and 4D (Dicaprate)) to dogs.
Figure 4B:
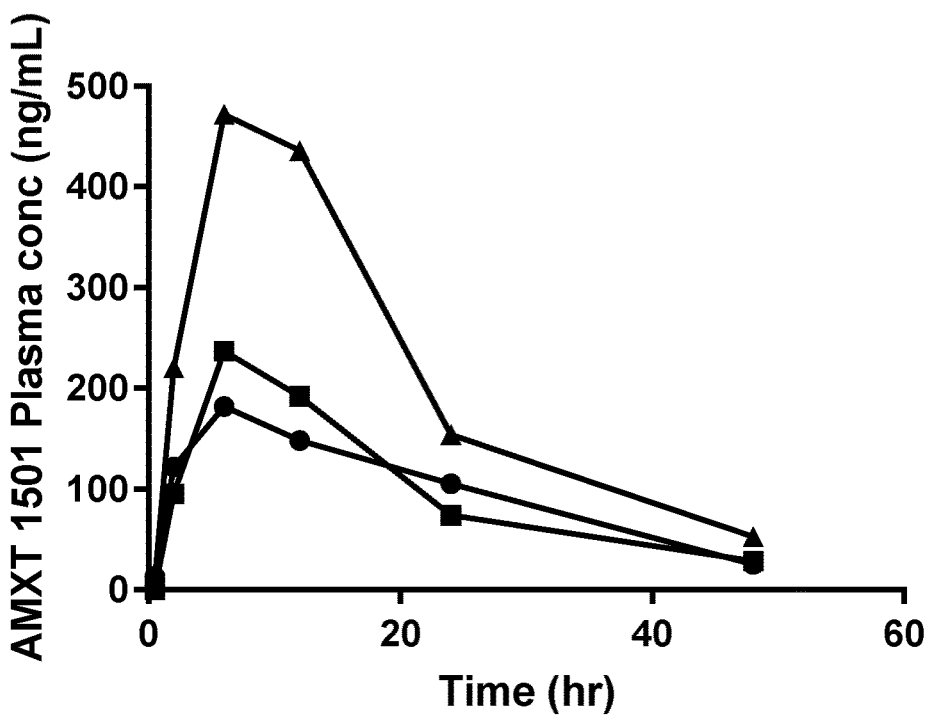
Figure 4C:
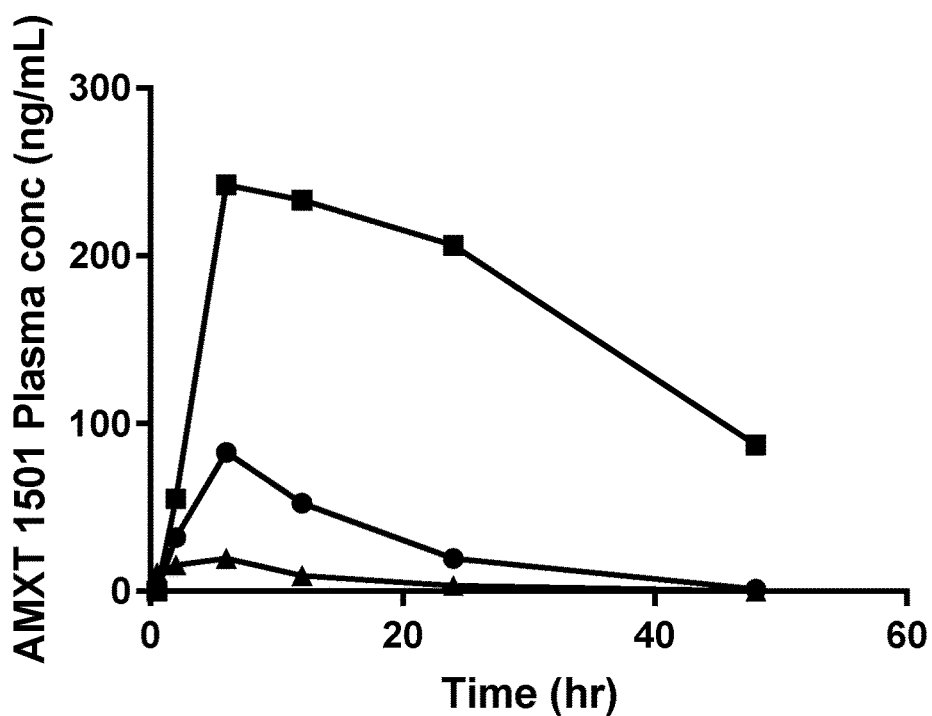
Figure 4D:
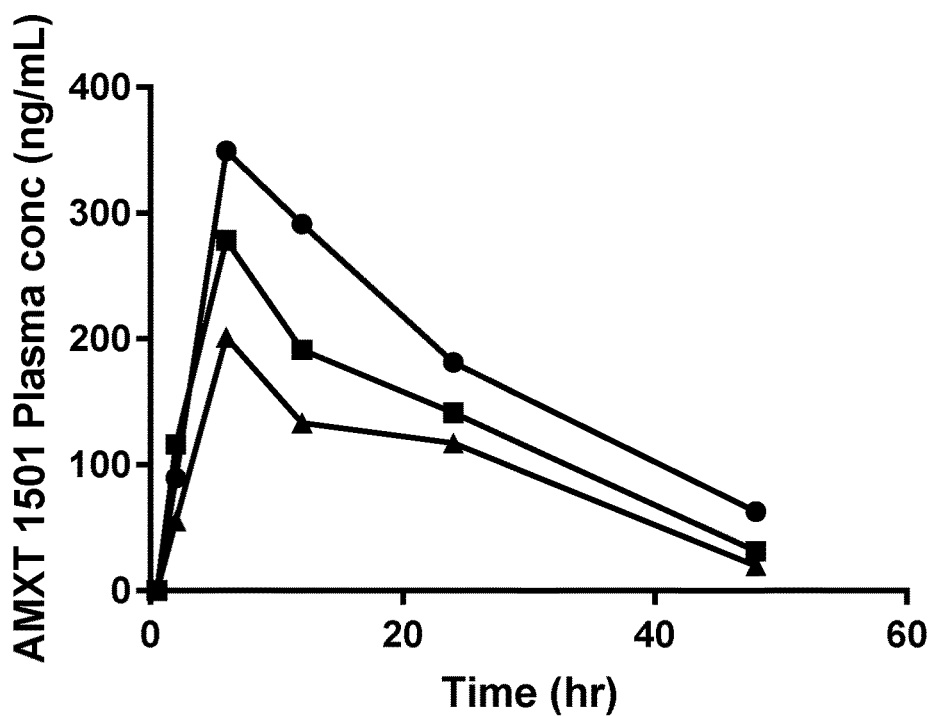
Figure 5A:
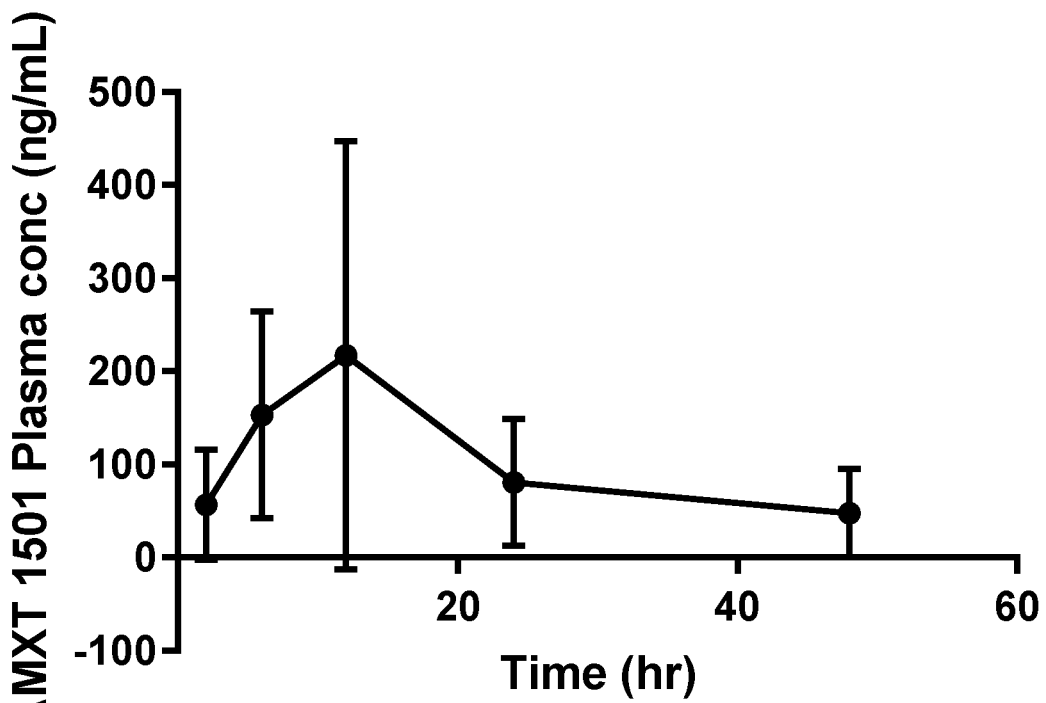
FIGS. 5A, 5B, 5C and 5D shows average plasma levels of AMXT 1501 following single oral dosing of groupings of dogs where either AMXT 1501 free base or various salt forms of AMXT 1501 (FIGS. 5B (Dicholate), 5C (Phosphate) and 5D (Dicaprate)) were dosed once by oral delivery.
Figure 5B:
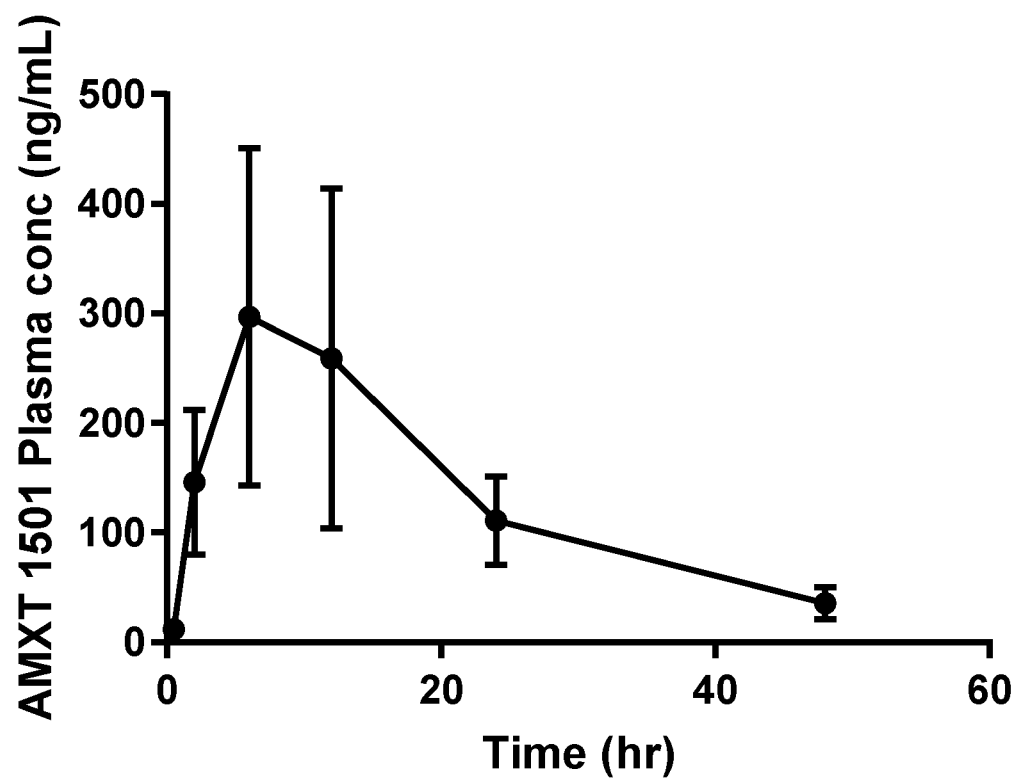
Figure 5C:
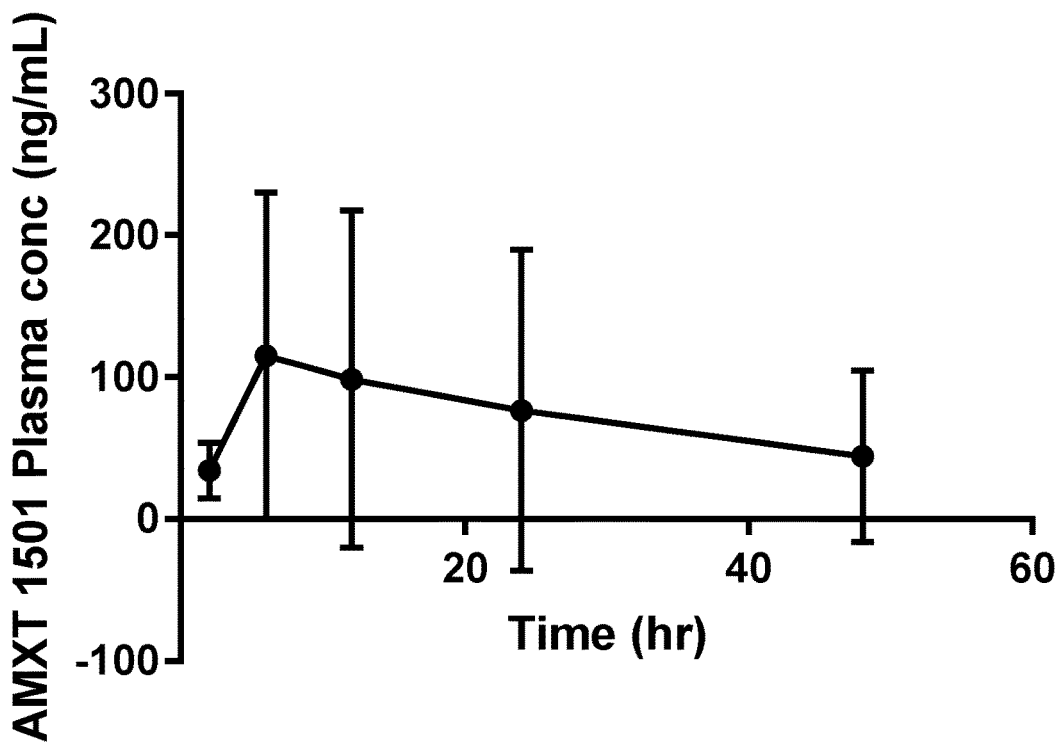
Figure 5D:
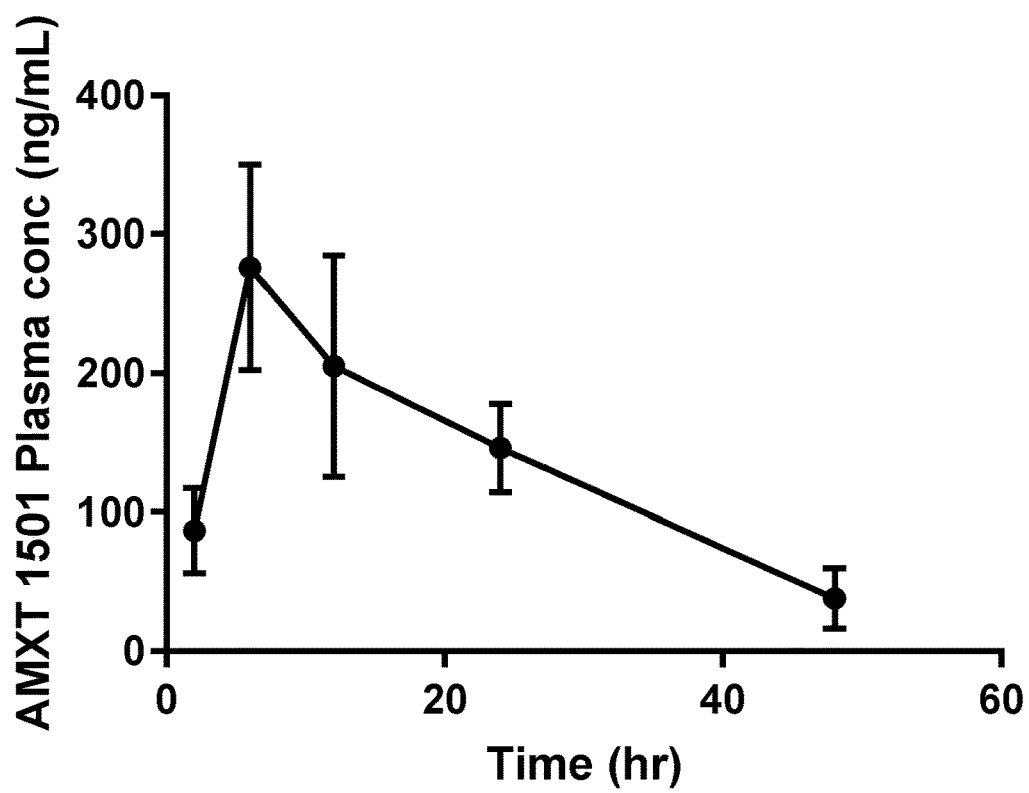

Results from this study are shown in the Figures, where FIGS. 4A, 4B, 4C and 4D show plasma levels obtained following single oral dosing of either AMXT 1501 free base or various salt forms of AMXT 1501 formulated in enterically coated tablets delivered to dogs. The data from Group 1 is shown in FIG. 4A, which shows plasma levels obtained following dosing of the free base form of AMXT 1501 and resulted in highly variable amounts of plasma AMXT 1501 obtained. Circle and square data points are from female dogs and the triangle data points are from a male dog. Higher plasma levels were obtained using the dicholate salt of AMXT 1501 following single oral dosing shown in FIG. 4B, which shows the data from Group 2 where the circle data points are from a female dog and the square and triangle data points are from male dogs. These results were consistent with the levels obtained using the dicaprate salt form of AMXT 1501 as determined from Group 4 animals and plotted in FIG. 4D, where circle data points are from a female dog and the square and rectangle data points are from male dogs. Plasma levels observed following oral dosing of the phosphate salt of AMXT 1501, i.e., the Group 3 animals, are plotted in FIG. 4C where circle and square data points are from female dogs and triangle data points are from a male dog, and again were highly variable and comparable to results obtained using the free base of AMXT 1501 (FIG. 4A). These results highlight the importance of the salt counterion and support use of lipophilic acids as the counterion in order to achieve, e.g., consistent sustained plasma levels of polyamine pharmaceuticals followed oral dosing.

FIGS. 5A, 5B, 5C and 5D shows average plasma AMXT 1501 levels obtained using the various compounds described in Table 13 following single oral delivery to Groups 1, 2, 3 and 4 of dogs. Average levels of AMXT 1501 are graphed in FIGS. 5A, 5B, 5C and 5D showing the standard deviation in the data, and highlight the variable drug levels observed using the free base and phosphate salt forms of AMXT 1501 (Group 1, FIG. 5A and Group 3, FIG. 5C, respectively) and the much more consistent inter-animal blood levels of AMXT 1501 obtained using the dicholate and dicaprate forms of AMXT 1501 (Group 2, FIG. 5B and Group 4, FIG. 5D, respectively). The dicholate and dicaprate salts, which are formed from representative hydrophobic carboxylic acids cholic acid and capric acid as disclosed herein, thus provide improved bioavailability compared to the free base or phosphate salt, in that the cholate and caprate salts do not show as much subject-to-subject variability when administered to test animals.

Example 8

5 Day Dog Repeat Oral Dosing with AMXT 1501 Dicaprate

The objectives of this portion of the study were to assess the pharmacokinetics (PK) of the dicaprate salt form of AMXT 1501 when administered via oral (PO) enterically-coated tablet administration to male and female beagle dogs across a range of dose levels and to compare AMXT 1501 dicaprate salt PK when administered with difluoromethylornithine (DFMO) compared to AMXT 1501 dicaprate salt alone, and to compare exposure after single and repeat AMXT 1501 dicaprate dosing. Male and female beagle dogs (N=1 or 2 males and 1 or 2 females, for a total of N=3 per group) were administered five daily oral (PO) tablet doses of the dicaprate salt form of AMXT 1501. AMXT 1501 dicaprate salt was administered as monotherapy at 8, 16, or 32 mg/kg, or at 16 mg/kg in combination with 200 mg/kg PO difluoromethylornithine (DFMO). The pharmacokinetic (PK) profiles after dosing on Days 1 and 5 were evaluated using standard noncompartmental methods.

Following single or repeat once daily PO dosing of 8, 16, or 32 mg/kg of the dicaprate salt form of AMXT 1501 to male and female beagle dogs, concentrations were measured out to 24 hr. postdose (the last measurable time point). The AMXT 1501 $T_{max}$ was observed at 4 to 12 hr. postdose, and exposure based on $C_{max}$ and $AUC_{0-t}$ increased in a dose-dependent manner. In the animals where it could be estimated, the mean Day 1 $t_{1/2}$ values ranged from 7.99 to 23.2 hr. and the mean Day 5 $t_{1/2}$ values ranged from 8.69 to 20.8 hr.

The following experimental design was used. Beagle dogs, 1 or 2 males and 1 or 2 females for a total of 3 dogs per group, were randomly assigned to the four treatment groups as outlined in Table 19.

TABLE 19

Study Design

| Group No. | AMXT 1501 Dose (mg/kg/day)[a] | Treatment | Nominal PK Sampling Time Points |
|---|---|---|---|
| 1 | 8 | AMXT 1501 dicaprate | 0.5, 1, 2, 4, 8, 12, and 24 hr. |
| 2 | 16 | AMXT 1501 dicaprate | |
| 3 | 32 | AMXT 1501 dicaprate | |
| 4 | 16 | AMXT 1501 dicaprate + DFMO[b] | |

[a]The AMXT 1501 dicaprate doses were administered as 80 mg (free base amounts) tablets (1, 2, 4, and 2 tablets per day in Groups 1, 2, 3, and 4, respectively).
[b]DFMO was administered following the AMXT 1501 dicaprate dose as a 40 mg/mL PO gavage with 200 mg/kg delivered.

AMXT 1501 dicaprate salt was administered in tablet form once daily for five days. After dosing on Days 1 and 5, serial blood samples were collected from each animal (3 per group) and processed to plasma for AMXT 1501 concentration analyses. Plasma samples were analyzed for AMXT 1501 concentration via a liquid chromatography/mass spectrometry (LC/MS-MS) procedure and the resulting concentration versus time data were used to estimate individual animal PK parameters using noncompartmental analysis (NCA).

Table 20 provides summarized AMXT 1501 plasma pharmacokinetics parameters following single (Day 1) or repeat once daily (Day 5) PO dosing of AMXT 1501 dicaprate salt to male and female beagle dogs.

TABLE 20

AMXT 1501 Plasma Pharmacokinetics Parameters Following Single (Day 1) or Repeat Once Daily (Day 5) PO Dosing to Male and Female Beagle Dogs

| Group | Treatment | Dose Level | Study Day | Animal ID | $T_{max}$ hr. | $C_{max}$ ng/mL | $AUC_{0-t}$ hr.* ng/mL | $t_{1/2}$ hr. |
|---|---|---|---|---|---|---|---|---|
| 1 | AMXT 1501 dicaprate | 8 mg/kg | 1 | 1F1 | 8.00 | 139 | 2010 | NC[a] |
| | | | | 1F2 | 4.00 | 168 | 2050 | 9.30 |
| | | | | 1M1 | NC[b] | NC[b] | NC[b] | NC[b] |
| | | | | Mean | 6.00 | 154 | 2030 | 9.30 |
| | | | | SD | 2.83 | 20.5 | 28.3 | N/A |
| 1 | AMXT 1501 dicaprate | 8 mg/kg | 5 | 1F1 | 4.00 | 405 | 5530 | 9.55 |
| | | | | 1F2 | 8.00 | 360 | 5620 | NC[a] |
| | | | | 1M1 | 4.00 | 254 | 3100 | 7.82 |
| | | | | Mean | 5.33 | 340 | 4750 | 8.69 |
| | | | | SD | 2.31 | 77.5 | 1430 | 1.22 |
| 2 | AMXT 1501 dicaprate | 16 mg/kg | 1 | 2F1 | 4.00 | 202 | 3870 | 36.2 |
| | | | | 2M1 | 4.00 | 262 | 3190 | 10.3 |
| | | | | 2M2 | 8.00 | 249 | 3300 | NC[a] |
| | | | | Mean | 5.33 | 238 | 3450 | 23.2 |
| | | | | SD | 2.31 | 31.6 | 364 | N/A |
| 2 | AMXT 1501 dicaprate | 16 mg/kg | 5 | 2F1 | 12.0 | 523 | 9410 | NC[a] |
| | | | | 2M1 | 4.00 | 454 | 6250 | 11.7 |
| | | | | 2M2 | 8.00 | 714 | 11000 | NC[a] |
| | | | | Mean | 8.00 | 564 | 8890 | 11.7 |
| | | | | SD | 4.00 | 135 | 2420 | N/A |
| 3 | AMXT 1501 dicaprate | 32 mg/kg | 1 | 3F1 | 4.00 | 563 | 6250 | 27.1 |
| | | | | 3F2 | 4.00 | 446 | 5830 | 10.0 |
| | | | | 3M1 | 8.00 | 333 | 4900 | NC[a] |
| | | | | Mean | 5.33 | 447 | 5660 | 18.6 |
| | | | | SD | 2.31 | 115 | 694 | N/A |
| 3 | AMXT 1501 dicaprate | 32 mg/kg | 5 | 3F1 | 4.00 | 1140 | 16800 | 10.7 |
| | | | | 3F2 | 8.00 | 662 | 11000 | NC[a] |
| | | | | 3M1 | 8.00 | 708 | 11100 | NC[a] |
| | | | | Mean | 6.67 | 837 | 13000 | 10.7 |
| | | | | SD | 2.31 | 264 | 3300 | N/A |
| 4 | AMXT 1501 dicaprate + DFMO | 16 mg/kg | 1 | 4F1 | 4.00 | 476 | 5480 | 7.99 |
| | | | | 4M1 | 8.00 | 317 | 5090 | NC[a] |
| | | | | 4M2 | 8.00 | 204 | 2980 | NC[a] |
| | | | | Mean | 6.67 | 332 | 4520 | 7.99 |
| | | | | SD | 2.31 | 137 | 1350 | N/A |
| 4 | AMXT 1501 dicaprate + DFMO | 16 mg/kg | 5 | 4F1 | 12.0 | 493 | 9540 | NC[a] |
| | | | | 4M1 | 4.00 | 418 | 7880 | 20.8 |
| | | | | 4M2 | 8.00 | 262 | 3680 | NC[a] |
| | | | | Mean | 8.00 | 391 | 7030 | 20.8 |
| | | | | SD | 4.00 | 118 | 3020 | N/A |

N/A: not applicable (N ≤ 2)
[a]NC: not calculated (not enough data in the terminal phase of the concentration versus time profile to calculate $t_{1/2}$)
[b]NC: not calculated (only one time point with measurable AMXT 1501 concentrations)

Figure 6A:
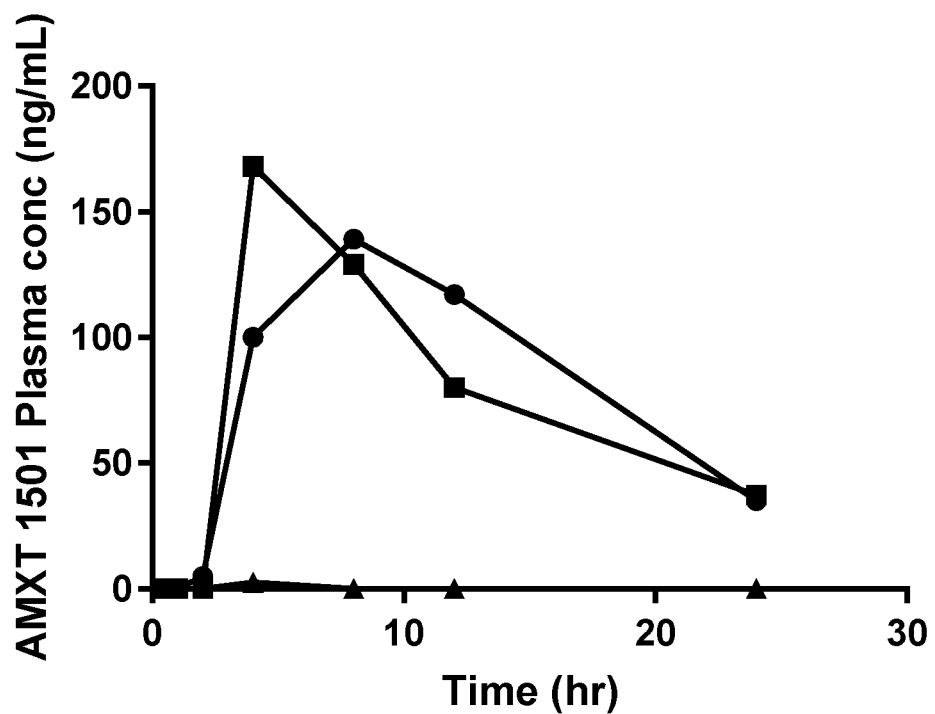
FIGS. 6A, 6B, 6C and 6D show individual animal AMXT 1501 plasma concentrations (ng/mL) following a single PO dose of AMXT 1501 dicaprate (8, 16 and 32 mg/kg/day and 16 mg/kg/day with 200 mg/kg/day DFMO) to male and female beagle dogs at day 1, according to a study as described herein.
Figure 6B:
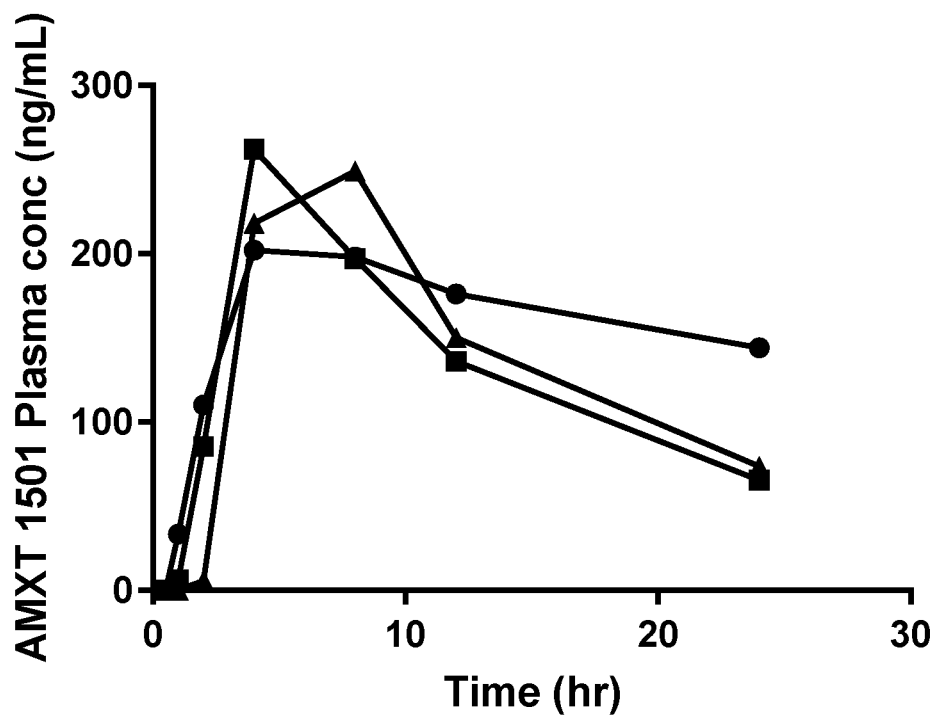
Figure 6C:
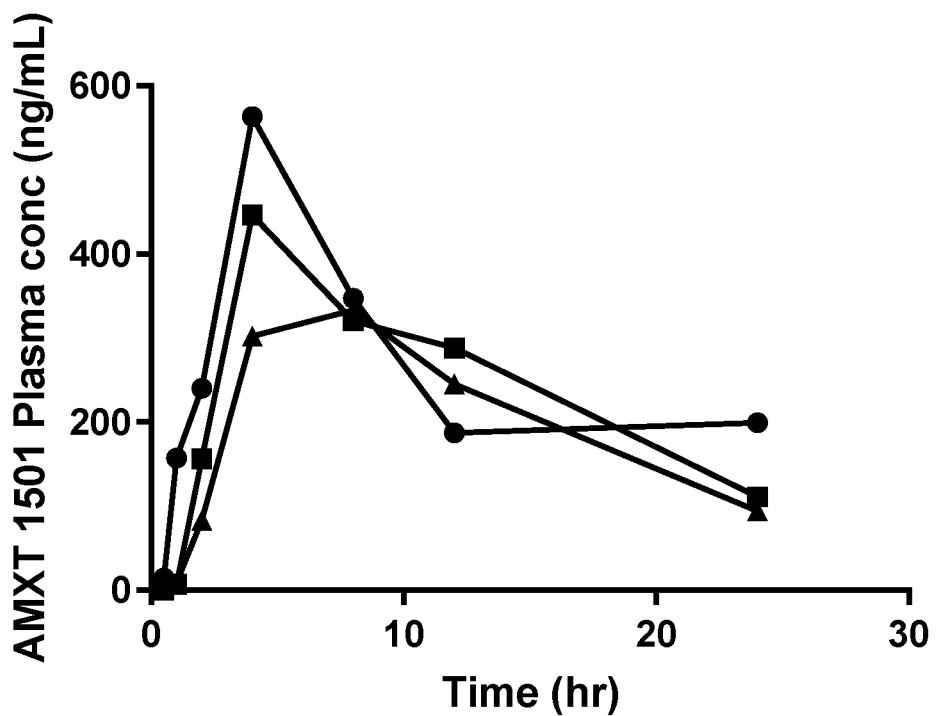
Figure 6D:
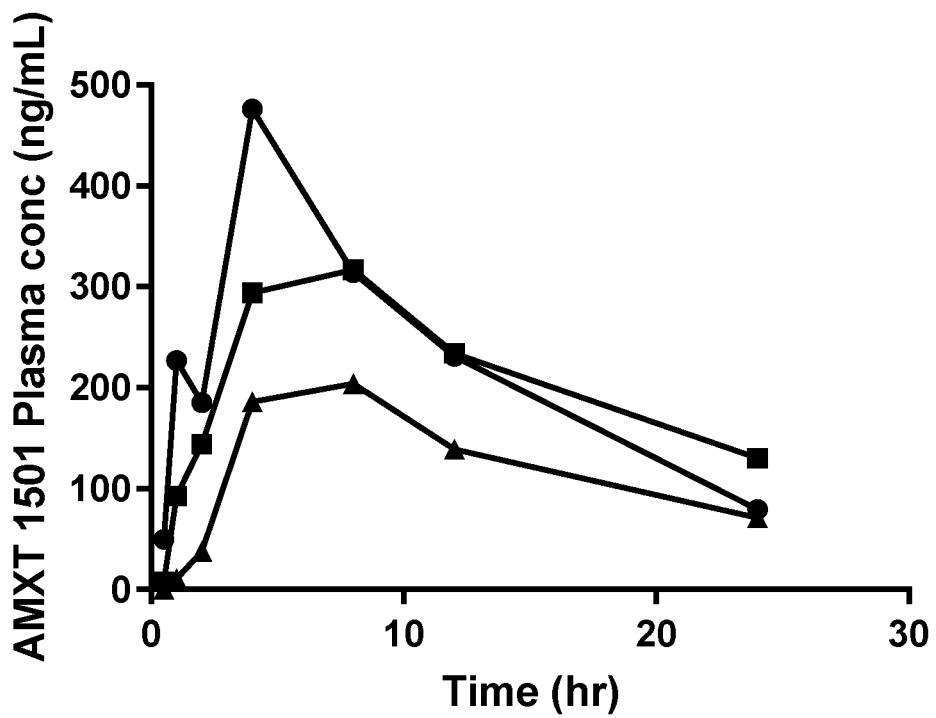

Selected results from this study are show in the figures, where FIGS. 6A, 6B, 6C and 6D show individual animal AMXT 1501 plasma concentrations (ng/mL) following a single PO dose of the enterically coated AMXT 1501 dicaprate tablets to male and female beagle dogs at day 1. FIG. 6A has a dose level of 8 mg/kg/day (Group 1; circle and square data points are from female dogs while triangle data points are from a male dog), FIG. 6B has a dose level of 16 mg/kg/day (Group 2; circle data points are from a female dog while square and triangle data points are from male dogs), FIG. 6C has a dose level of 32 mg/kg/day (Group 3; circle and square data points are from female dogs while the triangle data points are from a male dog), and FIG. 6D has a dose level of 16 mg/kg/day but includes DFMO in the dose (Group 4; circle data points are from a female dog while square and triangle data points are from male dogs).

Figure 7A:
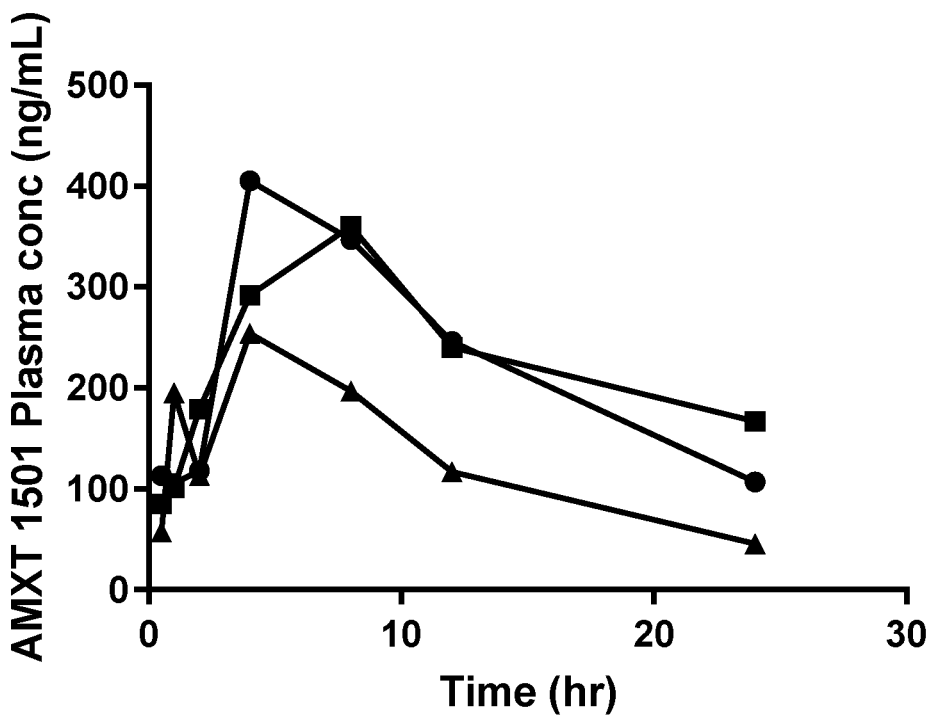
FIGS. 7A, 7B, 7C and 7D show individual animal AMXT 1501 plasma concentration (ng/mL) following repeat once daily PO dosing of AMXT 1501 dicaprate (8, 16 and 32 mg/kg/day and 16 mg/kg/day with 200 mg/kg/day DFMO) to male and female beagle dogs at day 5, according to a study as described herein.
Figure 7B:
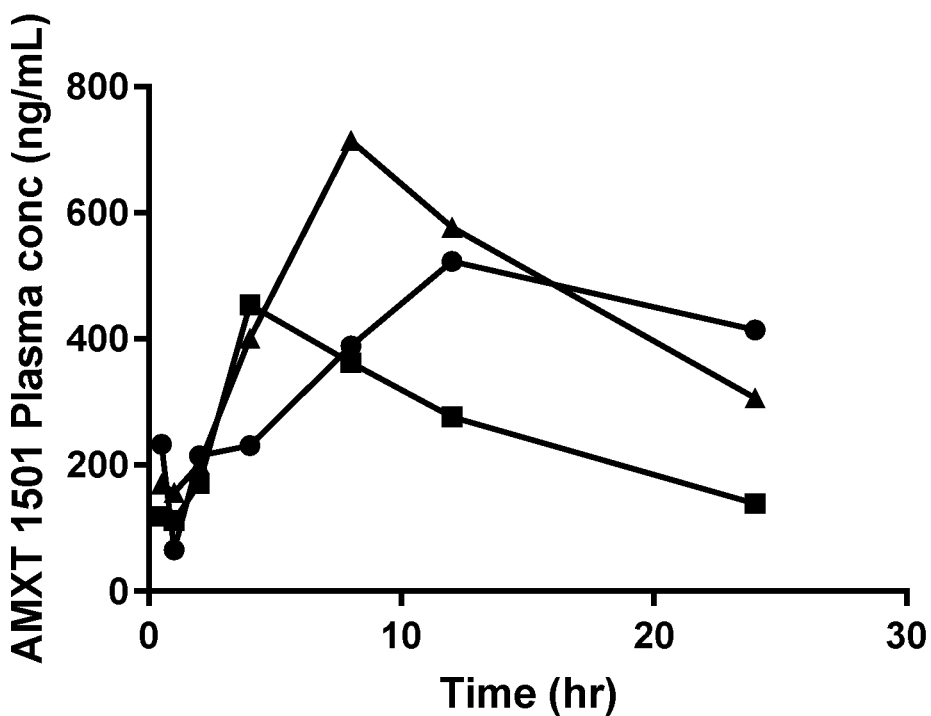
Figure 7C:
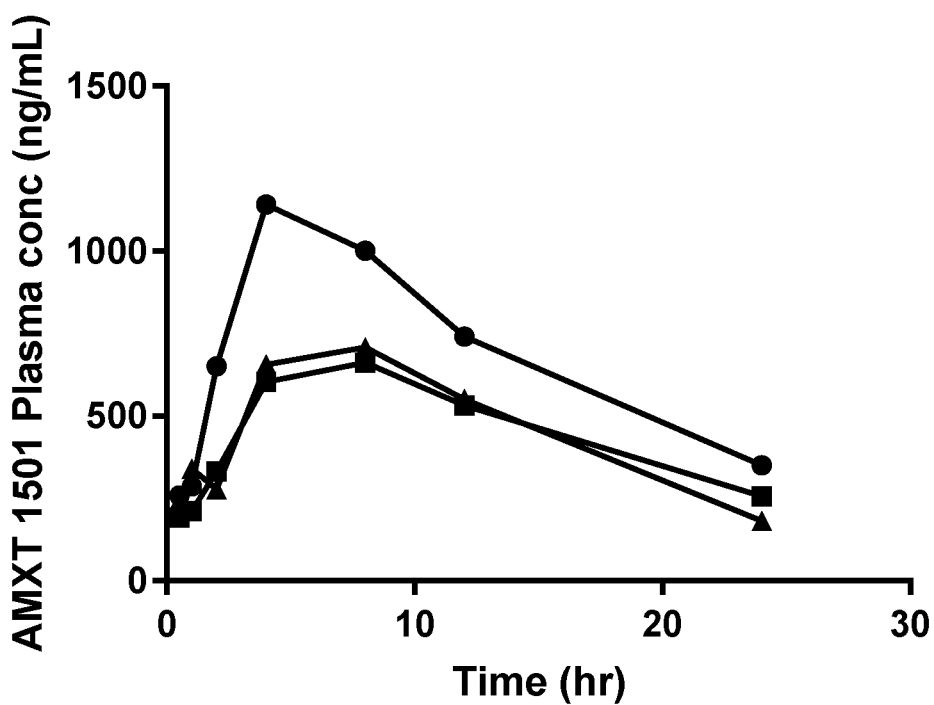
Figure 7D:
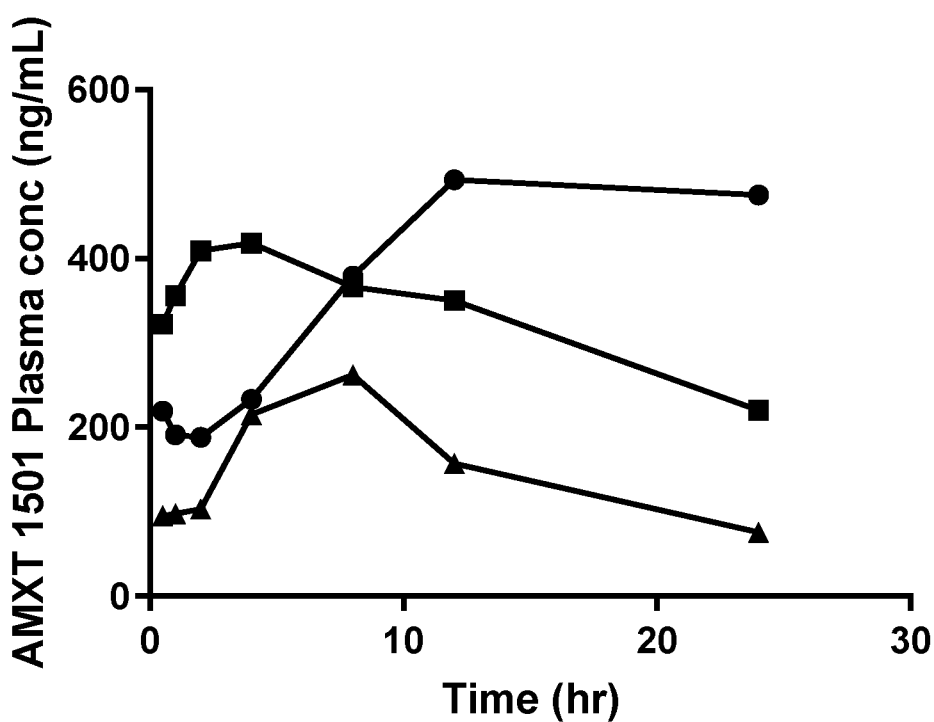

FIGS. 7A, 7B, 7C and 7D show individual animal AMXT 1501 plasma concentration (ng/mL) following repeat once daily PO dosing to male and female beagle dogs at day 5. FIG. 7A has a dose level of 8 mg/kg/day (Group 1), FIG. 7B has a dose level of 16 mg/kg/day (Group 2), FIG. 7C has a dose level of 32 mg/kg/day (Group 3), and FIG. 7D has a dose level of 16 mg/kg/day but includes DFMO in the dose (Group 4).

Figure 8A:
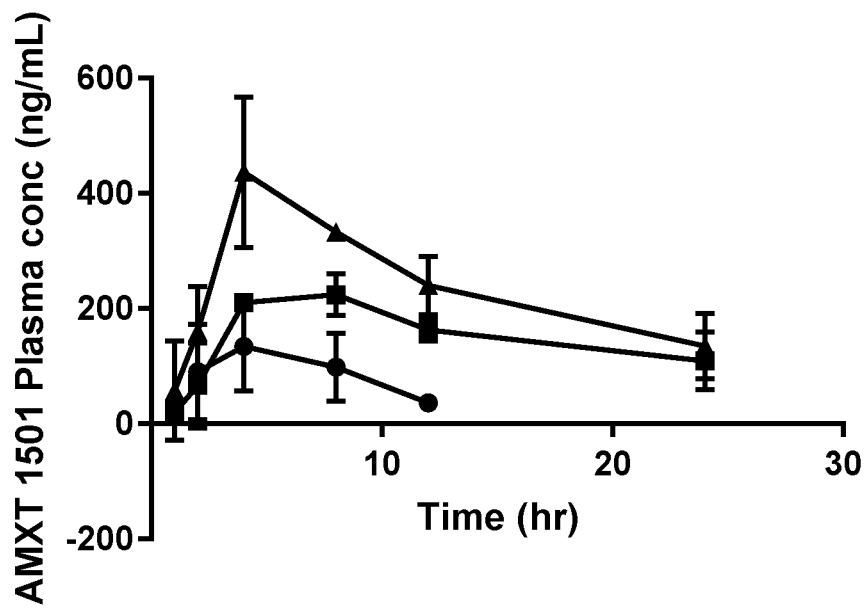
FIGS. 8A and 8B show mean (±SD) AMXT 1501 plasma concentrations (ng/mL) after single (Day 1.
Figure 8B:
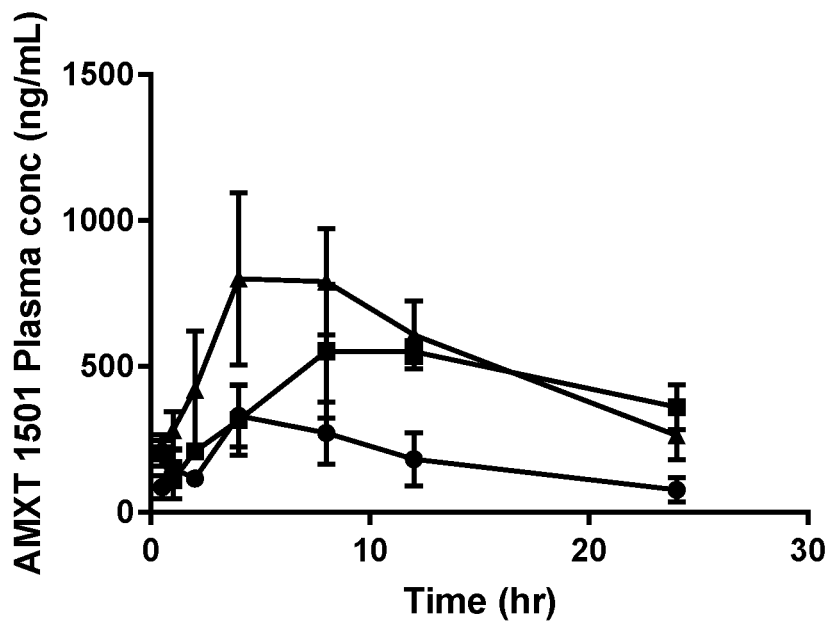

FIGS. 8A and 8B show mean (±SD) AMXT 1501 plasma concentrations (ng/mL) after single (Day 1; FIG. 8A) or repeat once daily (Day 5; FIG. 8B) PO dosing of AMXT 1501 dicaprate monotherapy to male and female beagle dogs. The circle data points are from animals receiving 8 mg/kg/day; the square data points are from animals receiving 16 mg/kg/day; and the triangle data points are from animals receiving 32 mg/kg/day.

Figure 9A:
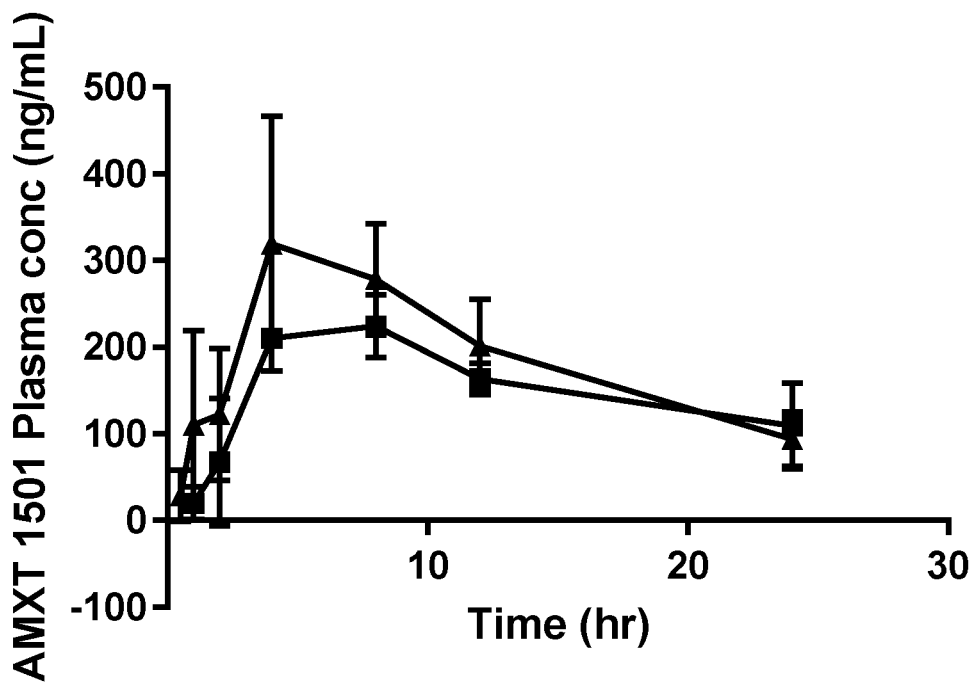
FIGS. 9A and 9B show mean (±SD) AMXT 1501 plasma concentrations (ng/mL) after single (Day 1.
Figure 9B:
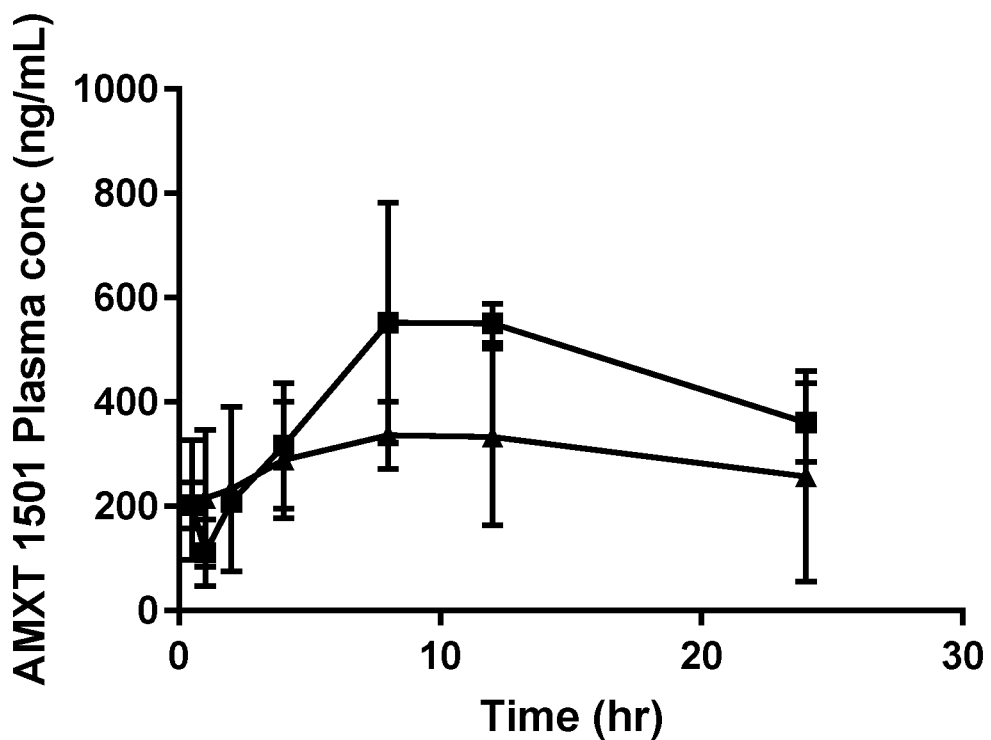

FIGS. 9A and 9B show mean (±SD) AMXT 1501 plasma concentrations (ng/mL) after single (Day 1; FIG. 9A) or repeat once daily (Day 5; FIG. 9B) PO dosing of 16 mg/kg AMXT 1501 dicaprate monotherapy versus 16 mg/kg AMXT 1501 dicaprate in combination with DFMO to male and female beagle dogs. In FIG. 9A, square data points are from Group 2 animals who received 16 mg/kg/day AMXT 1501 without DFMO while triangle data points are from Group 4 animals who received 16 mg/kg/day AMXT 1501 in combination with DFMO. FIG. 9B shows equivalent data from the same set of animals after 5 days of daily dosing.

Figure 10A:
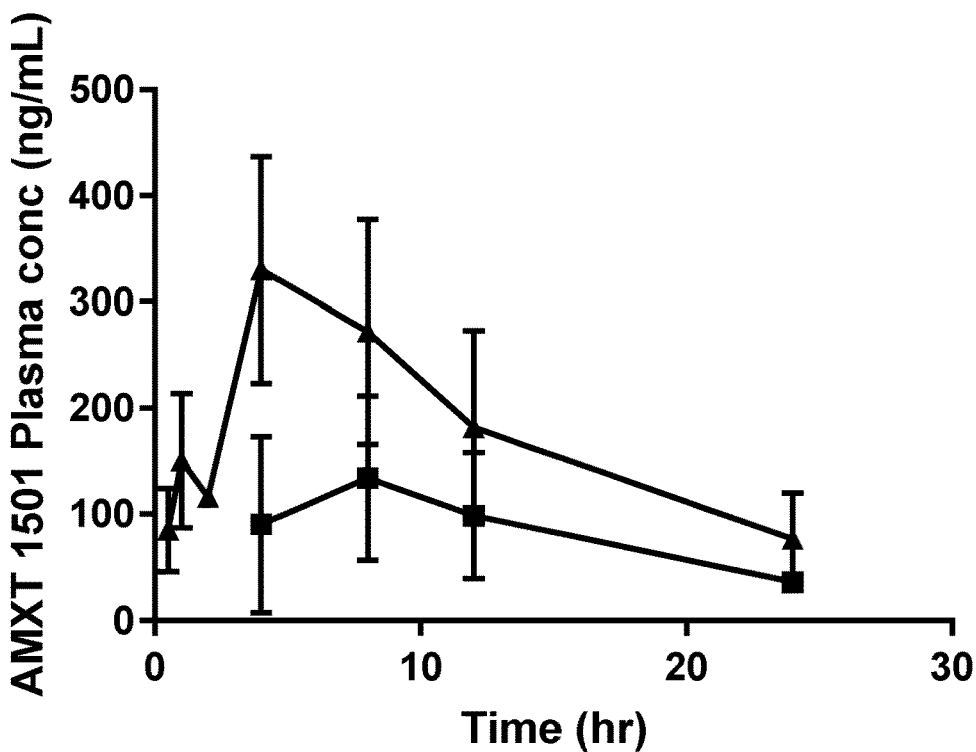
FIGS. 10A, 10B, 10C and 10D show mean (±SD) AMXT 1501 plasma concentrations (ng/mL) after single (Day 1) or Repeat Once Daily (Day 5) PO dosing of AMXT 1501 dicaprate (8, 16 and 32 mg/kg/day and 16 mg/kg/day with 200 mg/kg/day DFMO) to male and female beagle dogs, Day 1 versus Day 5, according to a study as described herein.
Figure 10B:
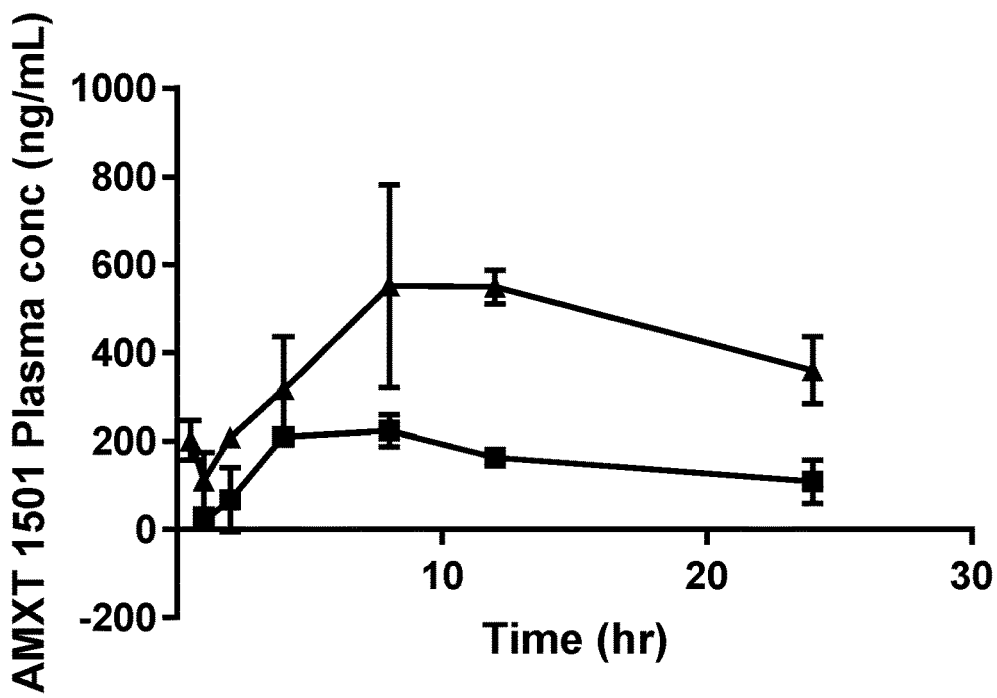
Figure 10C:
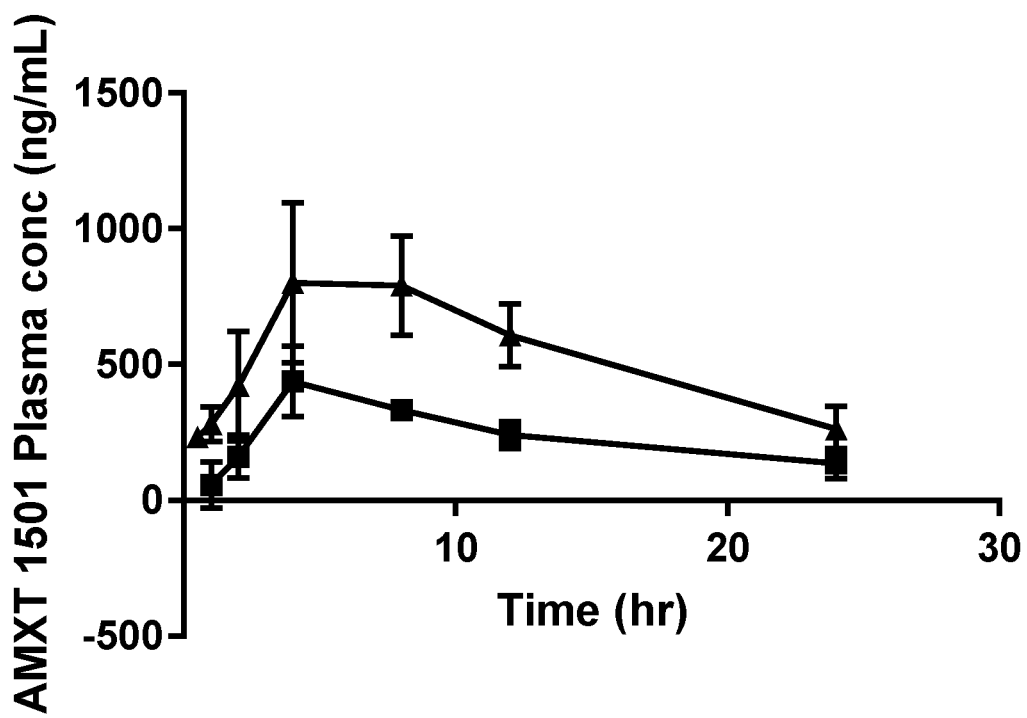
Figure 10D:
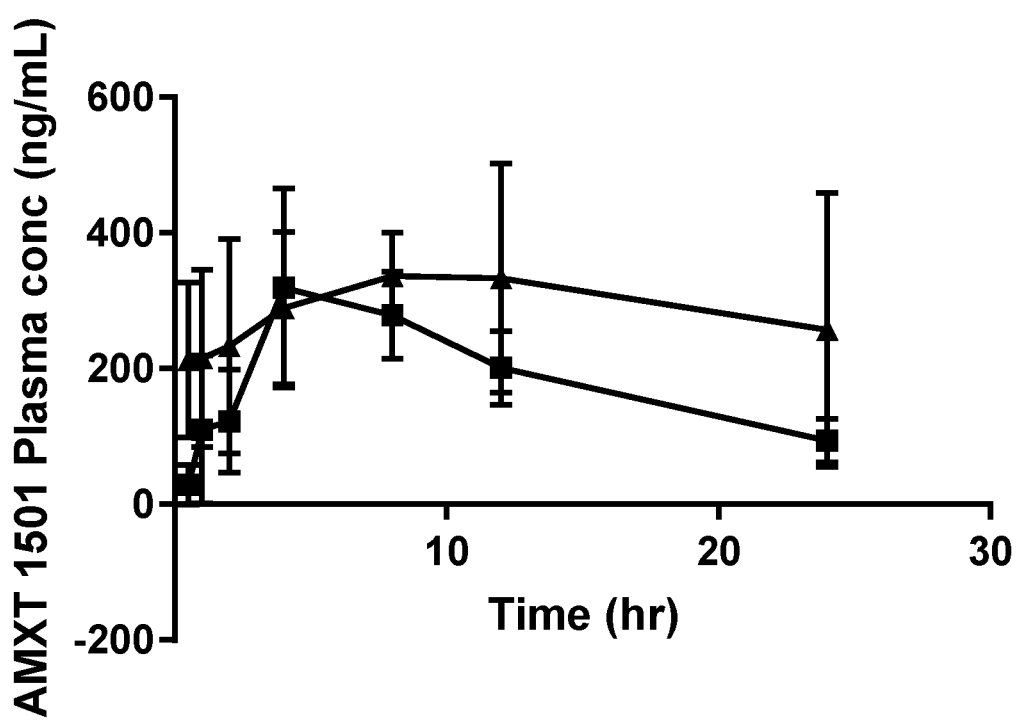

FIGS. 10A, 10B, 10C and 10D show mean (±SD) AMXT 1501 plasma concentrations (ng/mL) after single (Day 1) or Repeat Once Daily (Day 5) PO dosing to male and female beagle dogs, Day 1 versus Day 5. In FIG. 10A, the square data points are from Group 1 animals who received 8 mg/kg/day of AMXT 1501 dicaprate as measured on Day 1, while the triangle data points are from the same animals receiving the same daily dose but as measured on Day 5. In FIG. 10B, the square data points are from Group 2 animals who received 16 mg/kg/day of AMXT 1501 dicaprate as measured on Day1, while the triangle data points are from the same animals receiving the same daily dose but as measured on Day 5. In FIG. 10C, the square data points are from Group 3 animals who received 32 mg/kg/day of AMXT 1501 dicaprate as measured on Day1, while the triangle data points are from the same animals receiving the same daily dose but as measured on Day 5. In FIG. 10D, the square data points are from Group 4 animals who received 16 mg/kg/day of AMXT 1501 dicaprate and DFMO as measured on Day1, while the triangle data points are from the same animals receiving the same daily dose but as measured on Day 5.

These data demonstrate that the tested formulation and delivery methods provide sustained and consistent concentrations of AMXT 1501 in the plasma, after single dosing and after repeat dosing.

Example 9

AMXT 1501 Dicaprate PK Evaluation in Beagle Dogs During a 28-Day Repeat-Dose Toxicity Study Animals received once daily tablet, oral administration of 8, 16, or 32 mg/kg/day dose levels of AMXT 1501 dicaprate tablets without DFMO, or 8 or 16 mg/kg/day AMXT 1501 dicaprate salt with DFMO. AMXT 1501 PK parameters were calculated for all AMXT 1501 dicaprate-dosed animals for the first dose (Day 1) and last dose (Day 28).

AMXT 1501 exposure was maintained over the 24 hour dosing period at all tested dose levels. There was no obvious effect of gender on AMXT 1501 $T_{max}$. With the exception of Day 1 exposure in the 8 mg/kg/day AMXT 1501 without DFMO dose group, where mean $C_{max}$ and $AUC_{0-24\ hr}$ were consistent between genders, exposure was higher in females than in males after single or repeat dosing. After a single (Day 1) dose of AMXT 1501 dicaprate with or without DFMO, exposure based on mean $C_{max}$ and $AUC_{0-24\ hr}$ increased in a slightly less than dose-proportional manner. There was no consistent effect of gender, dose level, or DFMO on AMXT 1501 accumulation. Mean $AR_{Cmax}$ values ranged from 1.62 to 3.63 and mean $AR_{AUC}$ values ranged from 1.68 to 3.80. The Day 28 individual animal AMXT 1501 $t_{1/2}$ values ranged from 8.85 to 69.4 hours and tended to increase with increasing dose. There was no substantial effect of DFMO on single or repeat dose AMXT 1501 levels.

Figure 11A:
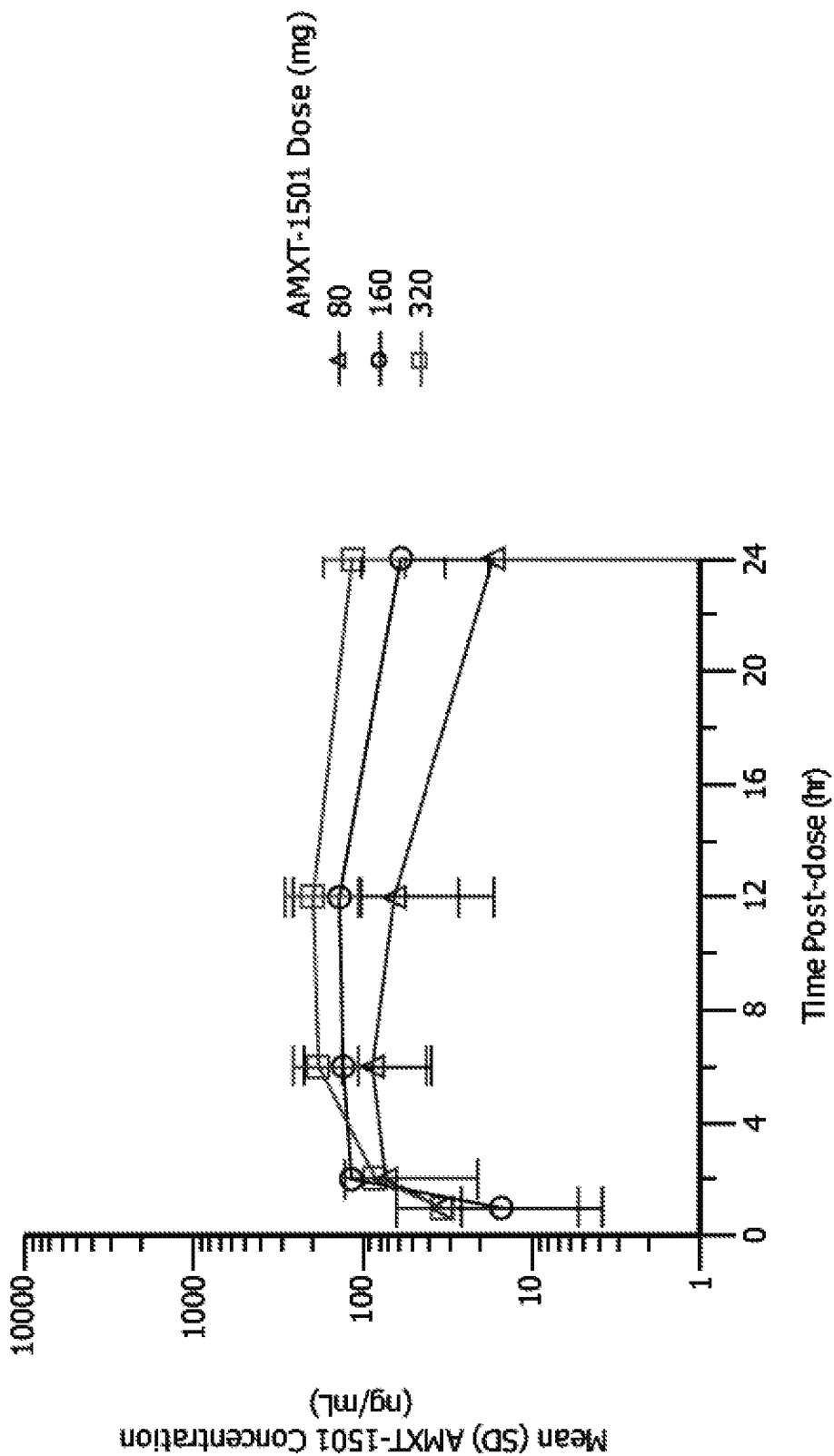
FIGS. 11A and 11B show mean (SD) AMXT 1501 Plasma Concentrations (ng/mL) Following Single (Day 1, FIG. 11A) or Repeat Oral Dosing (Day 28, FIG. 11B) to Male and Female Beagle Dogs; AMXT 1501 Dicaprate Dose Level Comparison (80, 160 or 320 mg of AMXT 1501 dicaprate) without DFMO (Males and Females Combined), according to a study as described herein.
Figure 11B:
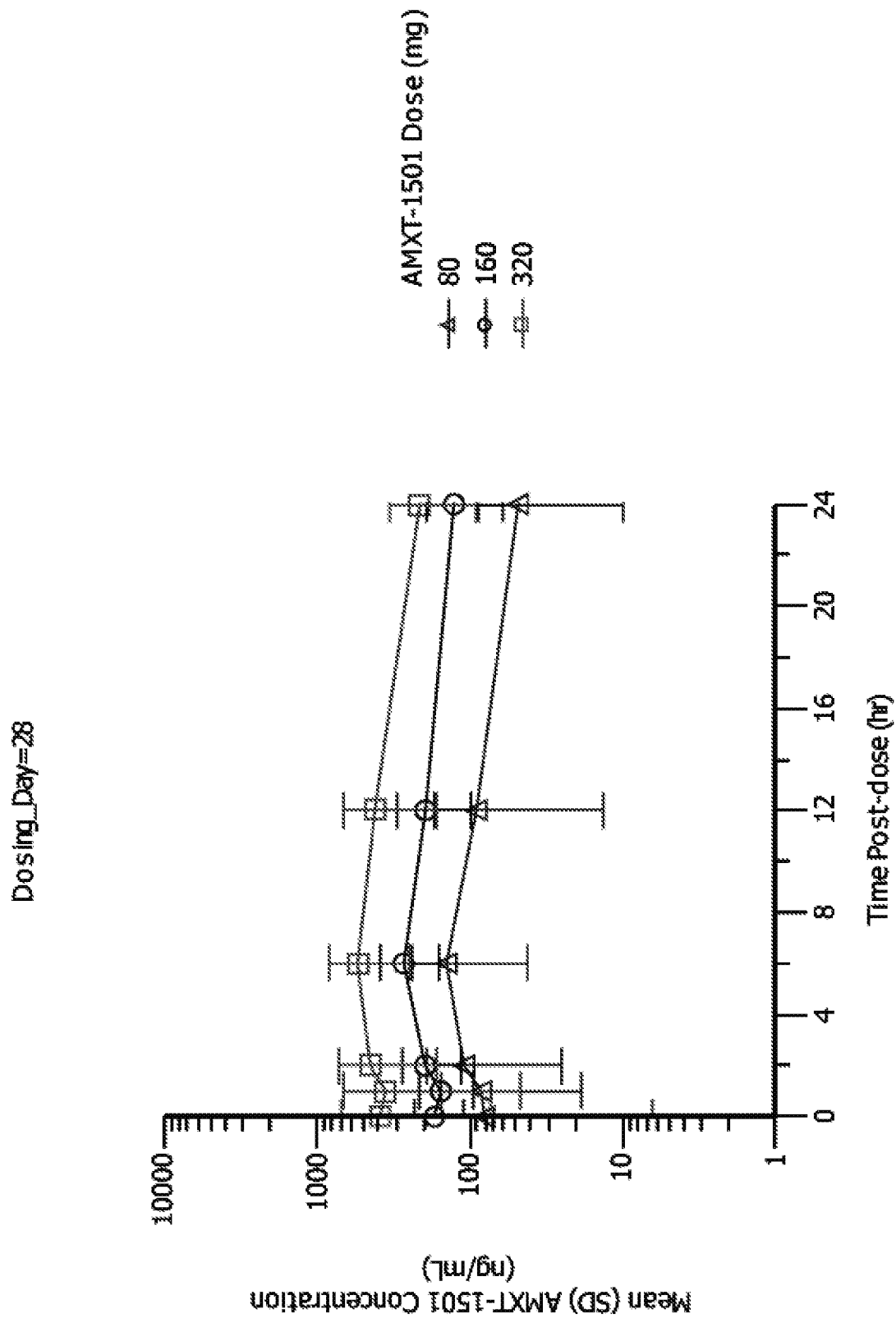
Figure 12A:
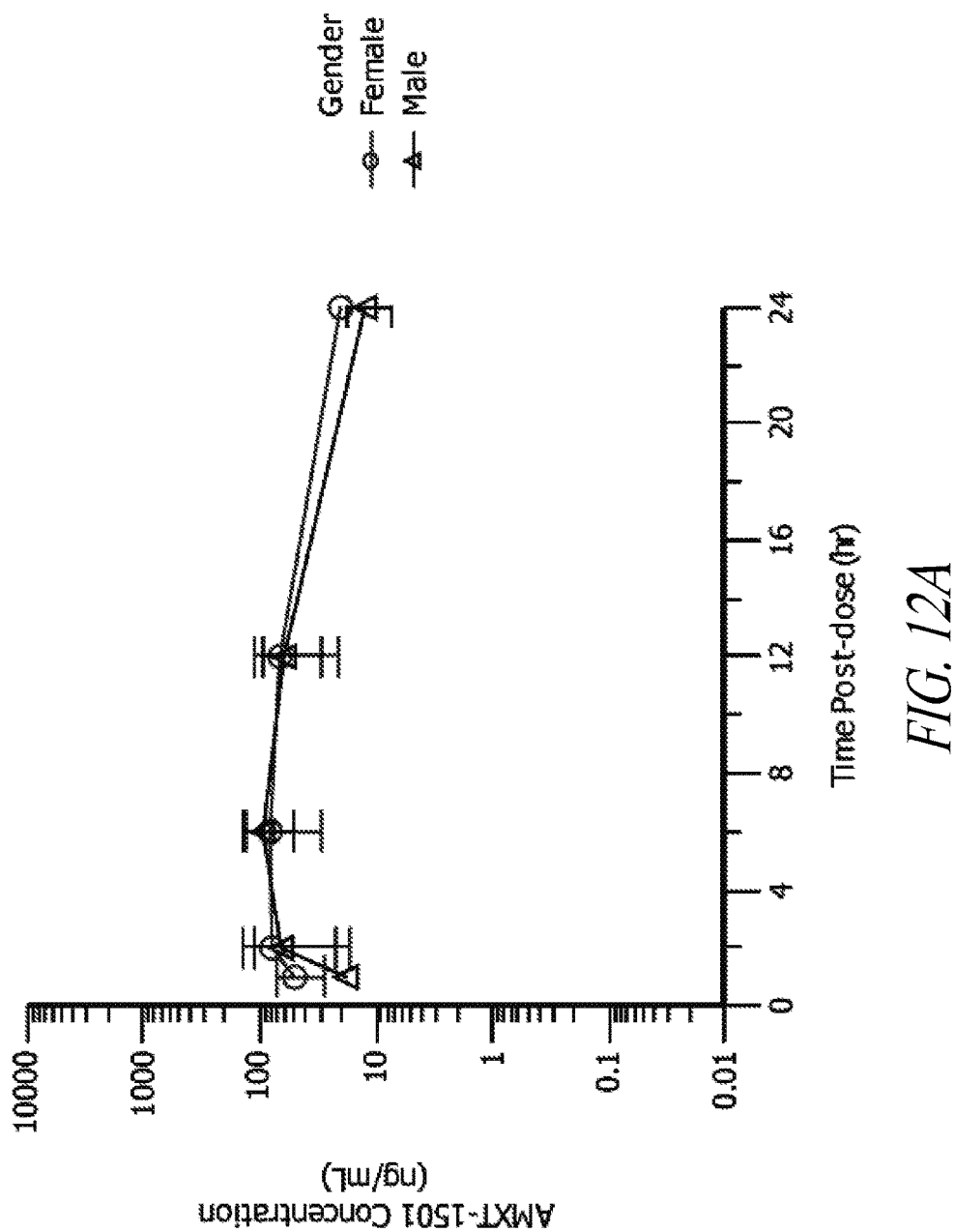
FIGS. 12A, 12B, 12C, 12D, 12E and 12F show mean (SD) AMXT 1501 Plasma Concentrations (ng/mL) Following Single (Day 1) or Repeat Oral Dosing (Day 28) to Male and Female Beagle Dogs; Males versus Females.
Figure 12B:
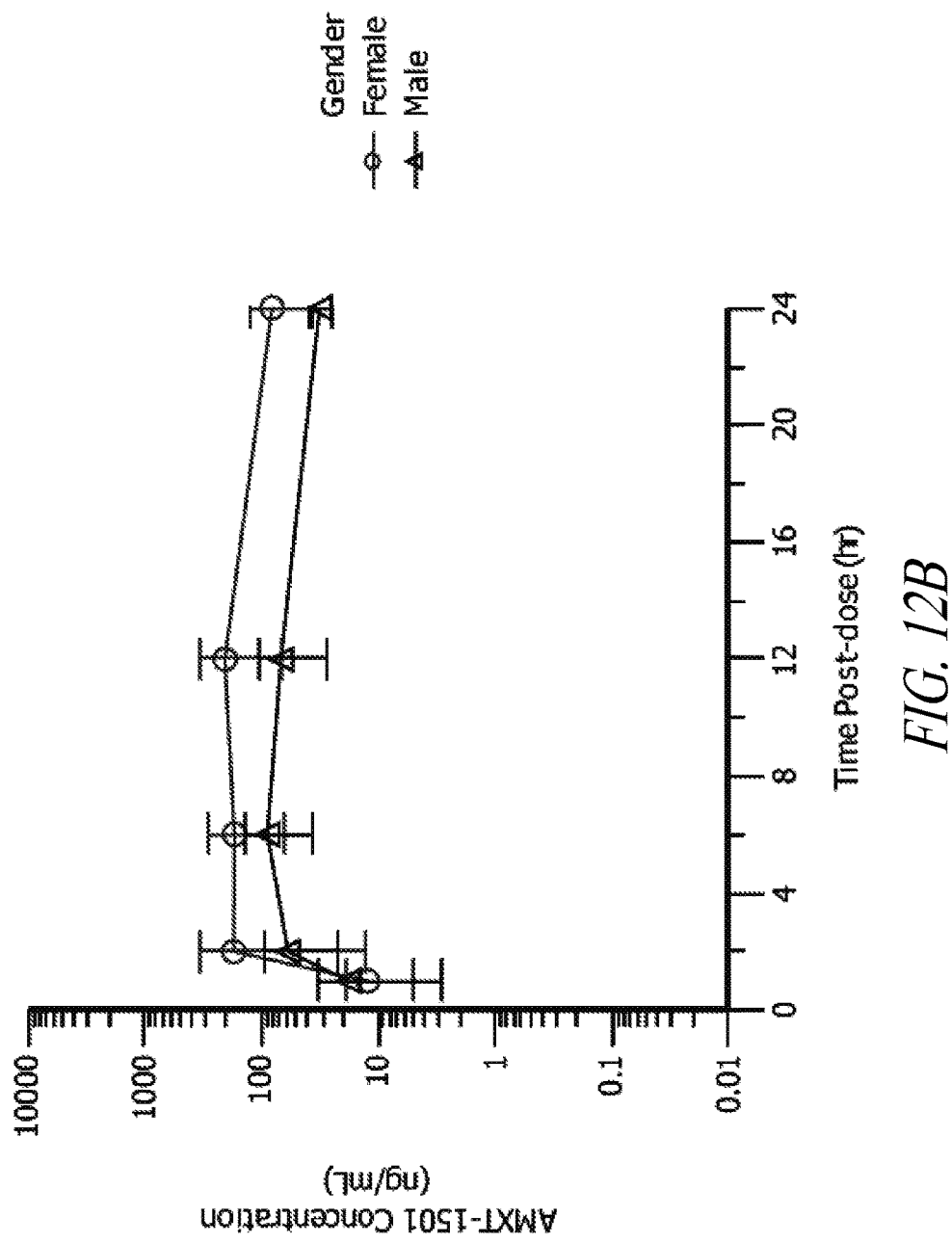
Figure 12C:
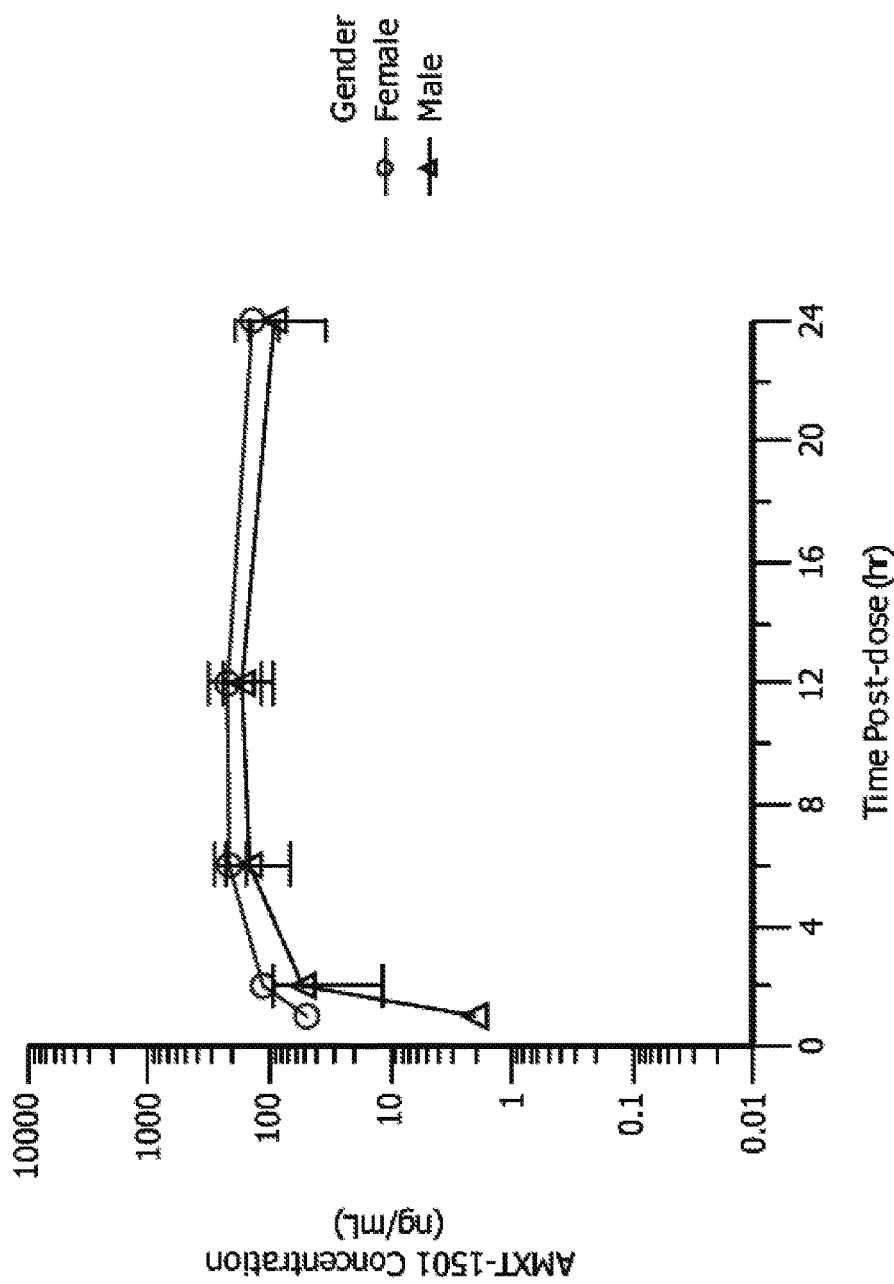
Figure 12D:
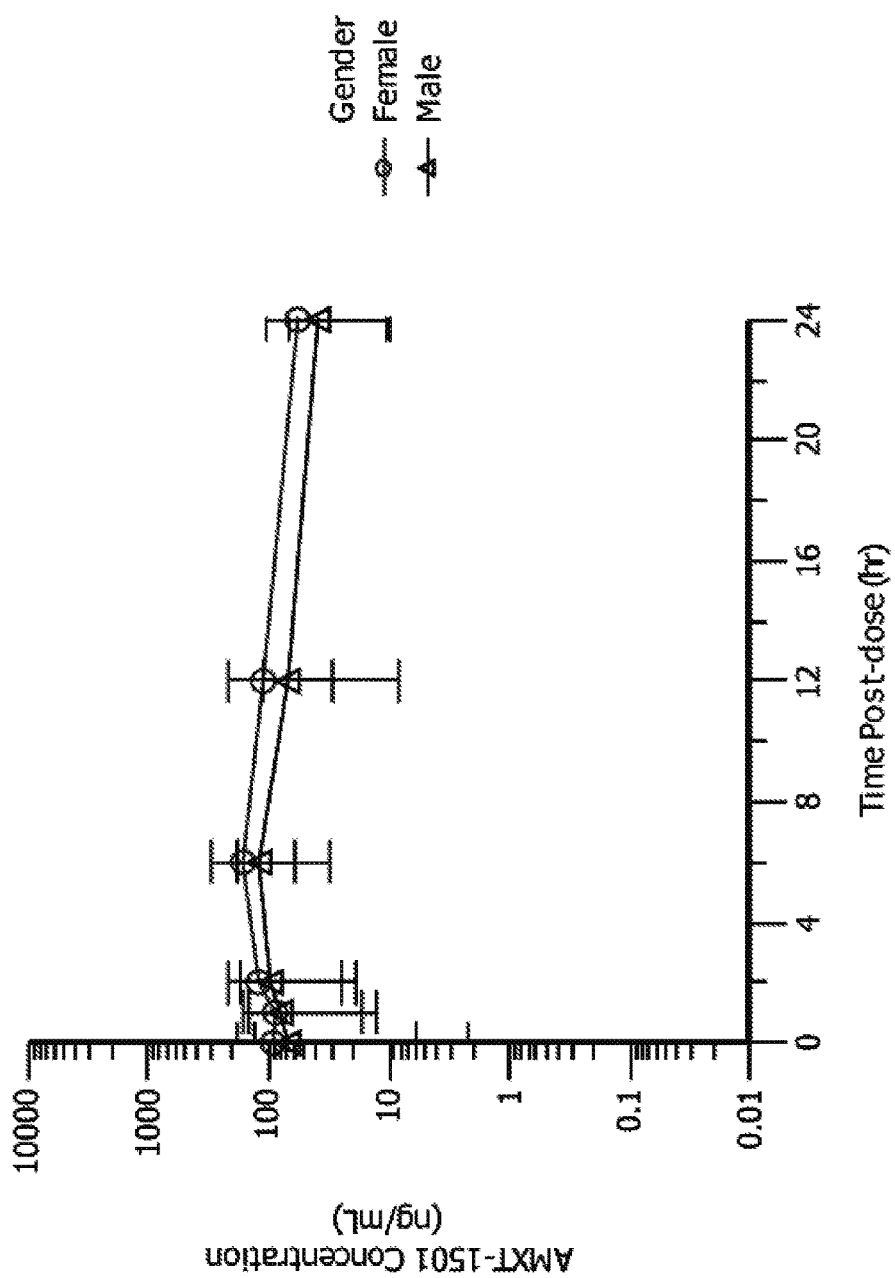
Figure 12E:
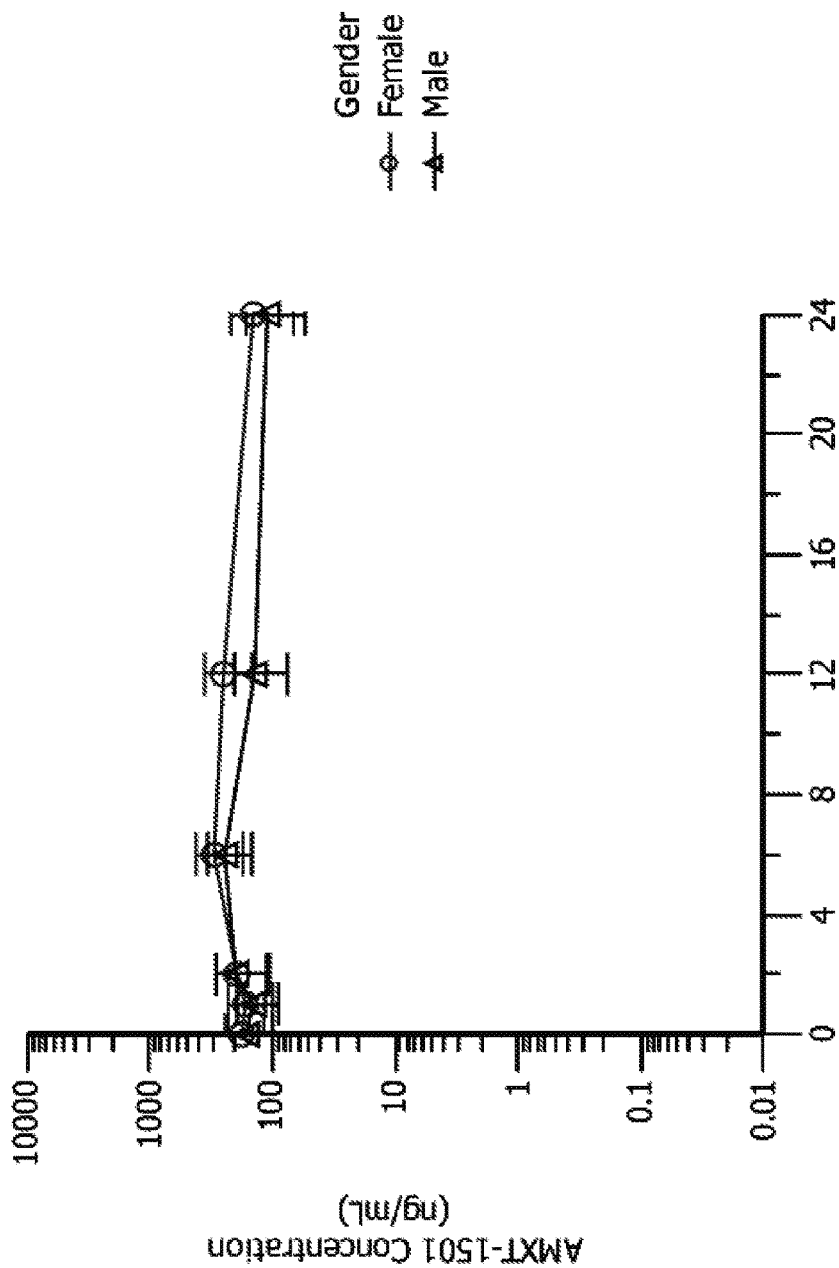
Figure 12F:
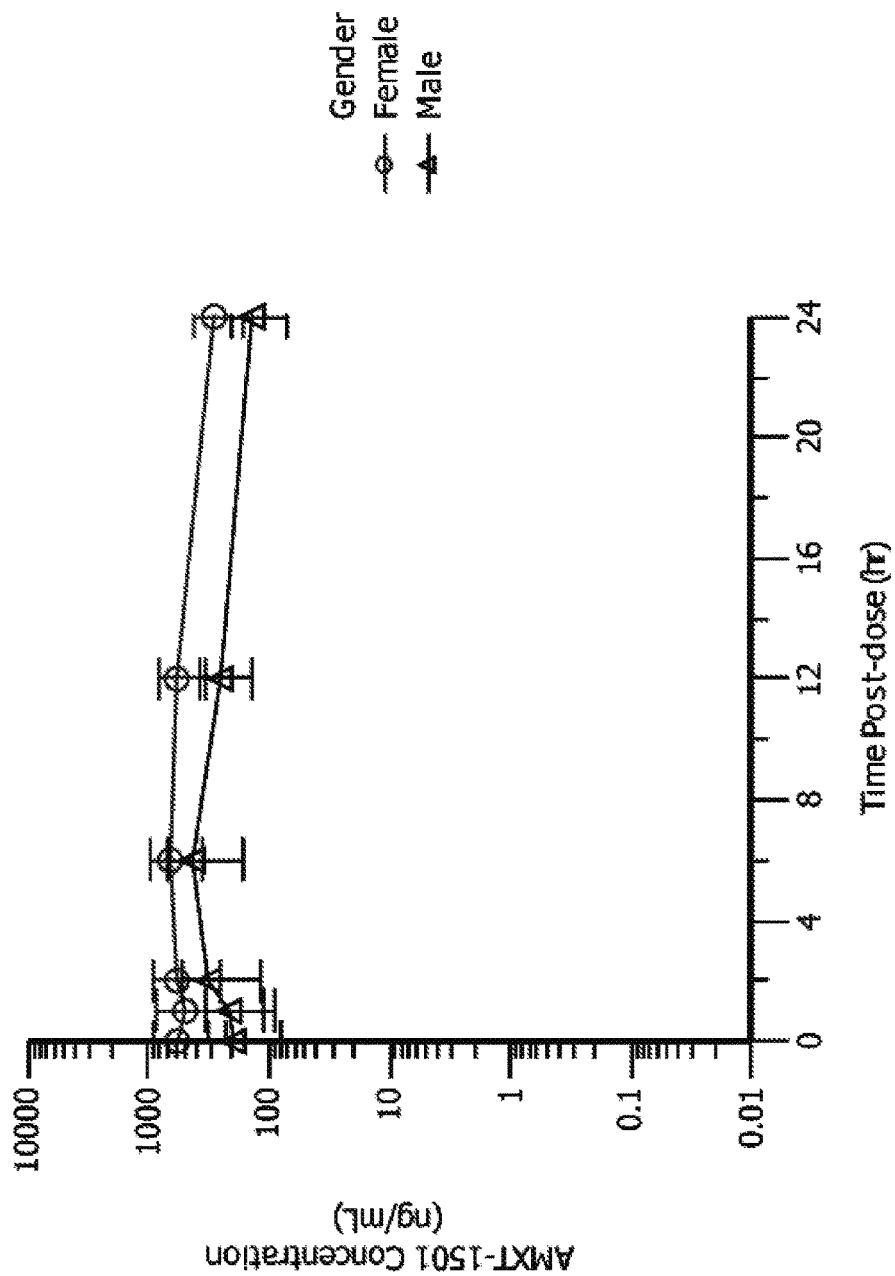
Figure 13A:
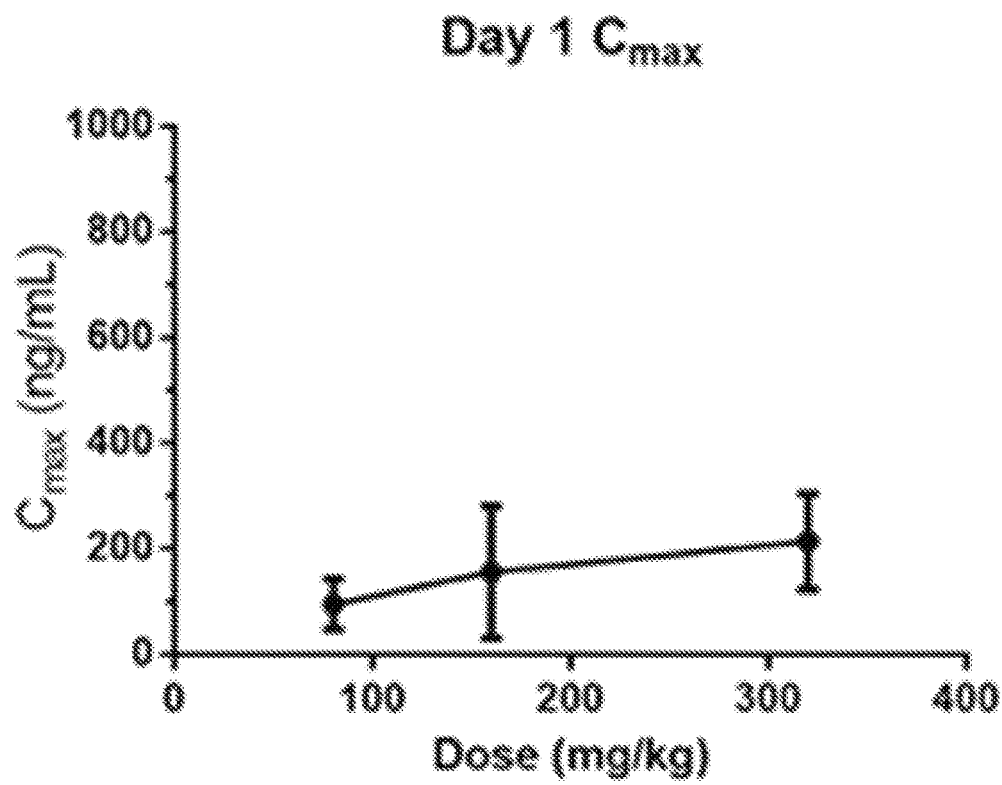
FIGS. 13A, 13B, 13C and 13D show dose-proportionality of oral delivery of AMXT 1501 dicaprate enterically-coated tablets to beagle dogs.
Figure 13B:
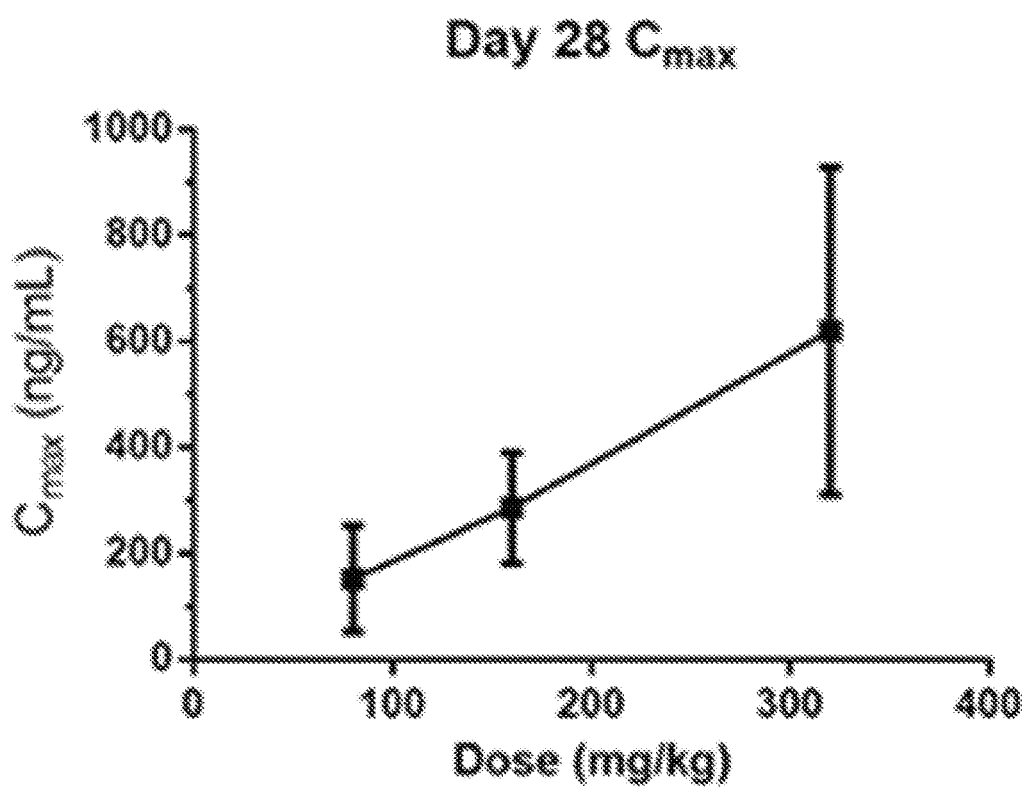
Figure 13C:
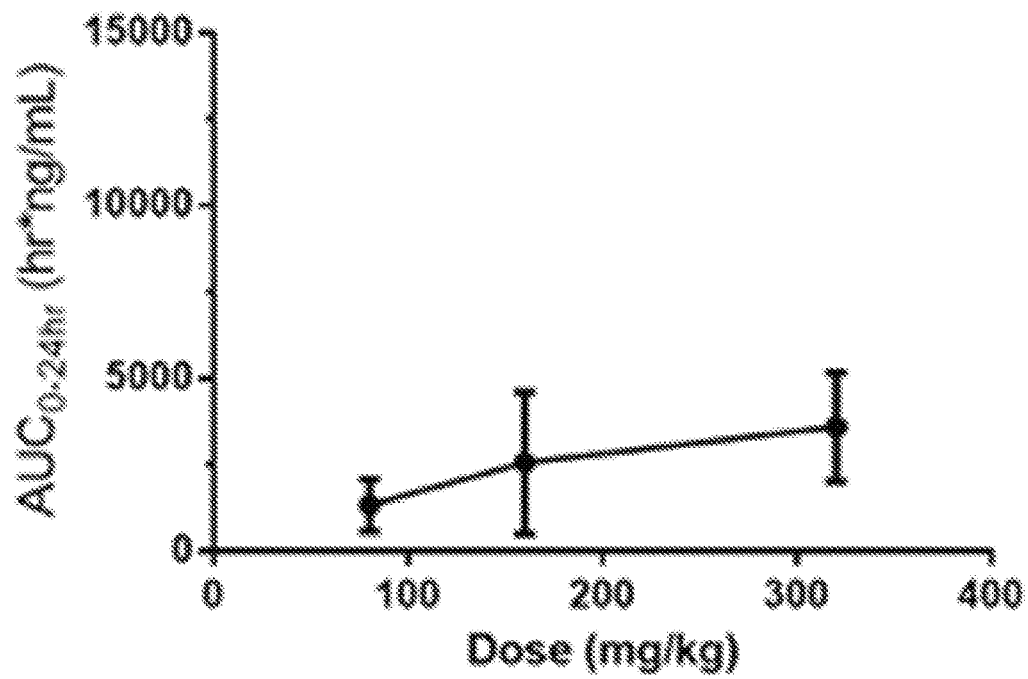
Figure 13D:
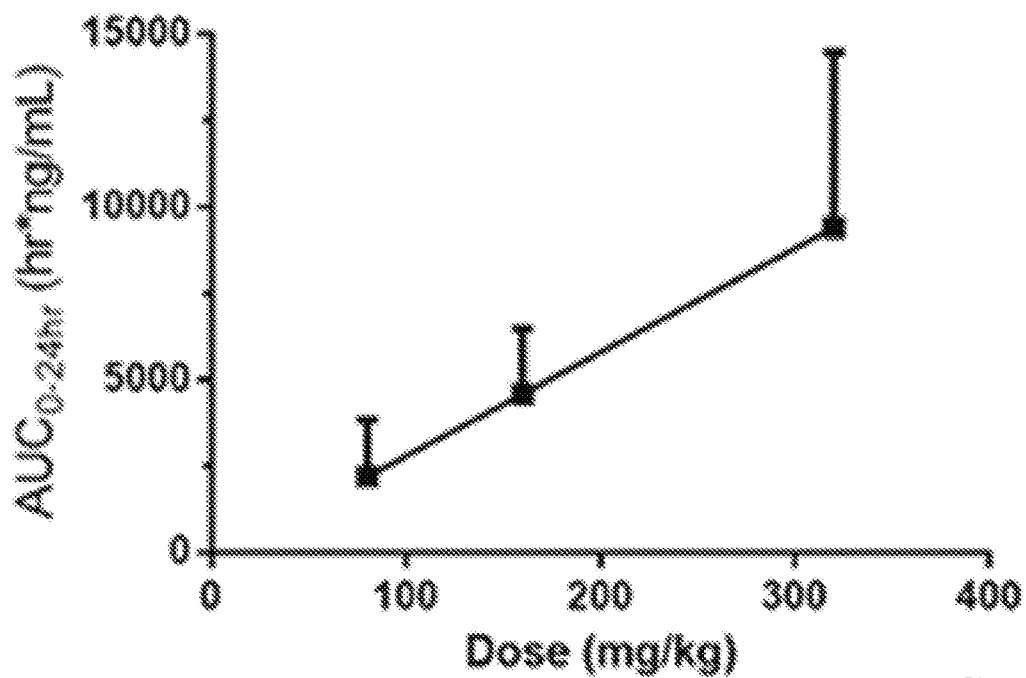

The data from these experiments are provided in FIGS. 11A and 11B which show mean (SD) AMXT 1501 plasma concentrations (ng/mL) following single (Day 1, FIG. 11A) or repeat oral dosing (Day 28, FIG. 11B) to male and female beagle dogs and AMXT 1501 dicaprate dose level comparison to the situation where no DFMO was administered (males and females combined). Data is also provides in FIGS. 12A, 12B, 12C, 12C, 12E and 12F which show mean (SD) AMXT 1501 plasma concentrations (ng/mL) following single (Day 1) or repeat oral dosing (Day 28) to male and female beagle dogs; males versus females. FIG. 12A shows data for Group 2 (low dose, 8 mg/kg/day), Day 1. FIG. 12B shows data for Group 3 (mid dose, 16 mg/kg/day), Day 1. FIG. 12C shows data for Group 4 (high dose, 32 mg/kg/day), Day 1. FIG. 12D shows data for Group 2 (low dose, 8 mg/kg/day), Day 28. FIG. 12E shows data for Group 3 (mid dose, 16 mg/kg/day), Day 28. FIG. 12F shows data for Group 4 (high dose, 32 mg/kg/day), Day 28, according to a study as described herein.

TABLE 21

Toxicokinetic Parameter Summary Following Repeat Once Daily Dosing of AMXT 1501 Dicaprate either Without or With DFMO in Male and Female Beagle Dogs; Males and Females Combined

| Group | AMXT 1501 Dose (mg/kg/day) | DFMO Dose (mg/kg/day) | Dosing Day | Parameter (Units) | N | Mean | SD | Min. | Median | Max. | CV % |
|---|---|---|---|---|---|---|---|---|---|---|---|
| 2 | 8 | 0 | 1 | $T_{max}$ (hr.) | 9 | 5.33 | 3.16 | 2.00 | 6.00 | 12.0 | 59.3 |
|   |   |   |   | $C_{max}$ (ng/mL) | 9 | 95.6 | 47.2 | 30.8 | 115 | 158 | 49.4 |
|   |   |   |   | $AUC_{0-24\ hr}$ (hr.*ng/mL) | 9 | 1330 | 755 | 374 | 1500 | 2810 | 56.5 |
| 2 | 8 | 0 | 28 | $T_{max}$ (hr.) | 10 | 4.60 | 2.32 | 0.00 | 6.00 | 6.00 | 50.4 |
|   |   |   |   | $C_{max}$ (ng/mL) | 10 | 153 | 100 | 17.7 | 127 | 360 | 65.3 |
|   |   |   |   | $AUC_{0-24\ hr}$ (hr.*ng/mL) | 10 | 2210 | 1650 | 249 | 1690 | 5230 | 74.6 |
|   |   |   |   | $AUC_{0-t}$ (hr.*ng/mL) | 4 | 3390 | 4120 | 308 | 1900 | 9470 | 121 |
|   |   |   |   | $AUC_{0-\infty}$ (hr.*ng/mL) | 4 | 3440 | 4170 | 328 | 1930 | 9590 | 121 |
|   |   |   |   | $t_{1/2}$ (hr.) | 4 | 19.7 | 8.18 | 12.6 | 18.7 | 28.8 | 41.5 |
| 3 | 16 | 0 | 1 | $T_{max}$ (hr.) | 10 | 6.00 | 3.65 | 2.00 | 6.00 | 12.0 | 60.9 |
|   |   |   |   | $C_{max}$ (ng/mL) | 10 | 155 | 125 | 10.4 | 113 | 408 | 80.5 |
|   |   |   |   | $AUC_{0-24\ hr}$ (hr.*ng/mL) | 10 | 2500 | 2050 | 104 | 1750 | 6350 | 81.8 |
| 3 | 16 | 0 | 28 | $T_{max}$ (hr.) | 10 | 5.60 | 3.10 | 0.00 | 6.00 | 12.0 | 55.3 |
|   |   |   |   | $C_{max}$ (ng/mL) | 10 | 286 | 104 | 109 | 309 | 408 | 36.3 |
|   |   |   |   | $AUC_{0-24\ hr}$ (hr.*ng/mL) | 10 | 4590 | 1890 | 1320 | 4890 | 7800 | 41.1 |
|   |   |   |   | $AUC_{0-t}$ (hr.*ng/mL) | 4 | 7970 | 2780 | 4870 | 8120 | 10800 | 34.8 |
|   |   |   |   | $AUC_{0-\infty}$ (hr.*ng/mL) | 4 | 8070 | 2820 | 4910 | 8280 | 10800 | 35.0 |
|   |   |   |   | $t_{1/2}$ (hr.) | 4 | 25.4 | 11.9 | 10.1 | 27.8 | 35.8 | 46.8 |
| 4 | 32 | 0 | 1 | $T_{max}$ (hr.) | 10 | 8.60 | 3.78 | 2.00 | 9.00 | 12.0 | 43.9 |
|   |   |   |   | $C_{max}$ (ng/mL) | 10 | 214 | 90.8 | 58.2 | 224 | 353 | 42.5 |
|   |   |   |   | $AUC_{0-24\ hr}$ (hr.*ng/mL) | 10 | 3590 | 1580 | 999 | 3640 | 6590 | 44.1 |
| 4 | 32 | 0 | 28 | $T_{max}$ (hr.) | 10 | 4.30 | 3.59 | 0.00 | 4.00 | 12.0 | 83.5 |
|   |   |   |   | $C_{max}$ (ng/mL) | 10 | 620 | 309 | 190 | 620 | 1110 | 49.9 |
|   |   |   |   | $AUC_{0-24\ hr}$ (hr.*ng/mL) | 10 | 9410 | 5060 | 2830 | 8760 | 16600 | 53.7 |
|   |   |   |   | $AUC_{0-t}$ (hr.*ng/mL) | 4 | 24700 | 13600 | 8730 | 24300 | 41500 | 54.9 |
|   |   |   |   | $AUC_{0-\infty}$ (hr.*ng/mL) | 4 | 24800 | 13600 | 8810 | 24400 | 41700 | 54.8 |
|   |   |   |   | $t_{1/2}$ (hr.) | 4 | 48.7 | 14.8 | 27.3 | 53.2 | 61.1 | 30.4 |
| 5 | 8 | 200 | 1 | $T_{max}$ (hr.) | 10 | 9.00 | 3.16 | 6.00 | 9.00 | 12.0 | 35.1 |
|   |   |   |   | $C_{max}$ (ng/mL) | 10 | 10.1 | 56.2 | 35.2 | 86.5 | 182 | 55.9 |
|   |   |   |   | $AUC_{0-24\ hr}$ (hr.*ng/mL) | 10 | 1470 | 853 | 323 | 1390 | 2670 | 58.1 |
| 5 | 8 | 50 | 28 | $T_{max}$ (hr.) | 9 | 6.67 | 3.61 | 0.00 | 6.00 | 12.0 | 54.1 |
|   |   |   |   | $C_{max}$ (ng/mL) | 9 | 152 | 76.9 | 48.0 | 171 | 275 | 50.5 |
|   |   |   |   | $AUC_{0-24\ hr}$ (hr.*ng/mL) | 9 | 2120 | 1410 | 366 | 2250 | 4230 | 66.7 |
|   |   |   |   | $AUC_{0-t}$ (hr.*ng/mL) | 3 | 3010 | 1990 | 1040 | 2970 | 5010 | 66.0 |
|   |   |   |   | $AUC_{0-\infty}$ (hr.*ng/mL) | 3 | 3070 | 2030 | 1060 | 3020 | 5120 | 66.2 |
|   |   |   |   | $t_{1/2}$ (hr.) | 3 | 18.0 | 8.28 | 8.85 | 20.3 | 24.9 | 45.9 |
| 6 | 16 | 200 | 1 | $T_{max}$ (hr.) | 10 | 8.40 | 3.10 | 6.00 | 6.00 | 12.0 | 36.9 |
|   |   |   |   | $C_{max}$ (ng/mL) | 10 | 152 | 89.7 | 7.27 | 171 | 263 | 59.1 |
|   |   |   |   | $AUC_{0-24\ hr}$ (hr.*ng/mL) | 10 | 2310 | 1430 | 94.4 | 2470 | 4280 | 62.1 |
| 6 | 16 | 50 | 28 | $T_{max}$ (hr.) | 10 | 6.30 | 4.52 | 0.00 | 6.00 | 12.0 | 71.8 |
|   |   |   |   | $C_{max}$ (ng/mL) | 10 | 262 | 170 | 98.4 | 213 | 578 | 64.8 |
|   |   |   |   | $AUC_{0-24\ hr}$ (hr.*ng/mL) | 10 | 4390 | 3270 | 1480 | 3340 | 10800 | 74.4 |
|   |   |   |   | $AUC_{0-t}$ (hr.*ng/mL) | 4 | 9440 | 8800 | 3410 | 6010 | 22300 | 93.2 |
|   |   |   |   | $AUC_{0-\infty}$ (hr.*ng/mL) | 4 | 9590 | 8860 | 3610 | 6080 | 22600 | 92.4 |
|   |   |   |   | $t_{1/2}$ (hr.) | 4 | 52.8 | 20.5 | 26.4 | 57.8 | 69.4 | 38.7 |

Abbreviations: Max = maximum; Min = minimum; N = number of animals; SD = standard deviation.
All TK parameters are shown to 3 significant digits.

FIGS. 13A, 13B, 13C and 13D show delivery of various dose levels of AMXT 1501 dicaprate in enterically-coated tablets orally to beagle dogs. These figures show approximately dose-proportional increases in plasma levels of AMXT 1501 at dose levels of 8, 16 and 32 mg/kg/day after Day 1 and Day 28. These dose levels were equivalent to 1, 2 and 4 tablets of AMXT 1501 dicaprate (80 mg AMXT 1501 free base content per tablet) to these animals, which had an average 10 kg body weight. The PK parameters $C_{max}$ and $AUC_{0-24\ hr}$ both showed dose-proportionality. These data demonstrate that pharmacological dosing with AMXT 1501 dicaprate in enterically-coated tablets provides a predictable and reliable delivery method for this polyamine active pharmaceutical.

Example 10

Pharmaceutical Formulation of AMXT 1501 Dicaprate

Table 22 below shows the composition of the enterically-coated tablet pharmaceutical containing AMXT 1501 dicaprate. Modern pharmaceuticals commonly contain tableting formulation ingredients such as these to increase the functionality and oral delivery of the resulting active drug(s). Descriptions and functions of these common formulation ingredients, commonly known as excipients are given below.

TABLE 22

Solid Oral Dosage Composition

| Item No. | Ingredient/Component No. | Function of Ingredient | Concentration (% W/W) | Amount/Tablet mg |
|---|---|---|---|---|
| 1 | AMXT 1501 Dicaprate | Active | 32.75 | 131.0 |
| 2 | Co-processed Starch, NF (StarCap 1500) | Filler/Diluent | 23.40 | 93.6 |
| 3 | Microcrystalline Cellulose NF, PH Eur., JP (Avicel PH102) | Filler/Diluent | 33.98 | 135.9 |
| 4 | Ac-Di-Sol Croscarmellose Sodium NF, PH. Eur., JP | Disintegrant | 6.90 | 27.6 |
| 5 | Hydrophobic Colloidal Silica NF, Ph. Eur. (Aerosil R972) | Glidant | 1.49 | 3.95 |
| 6 | Magnesium Stearate, NF (Hyqual Vegetable Source) | Lubricant | 1.49 | 3.95 |
| | TOTAL | | 100 | 400 |

Following mixing of the dry ingredients listed above, this powdered formulation is loaded into an appropriate tablet press to produce the uncoated tablets. Quality control testing is performed and content of active drug is evaluated (Assay %) together with Content Uniformity (CU) across a sample of uncoated tablets. Coating of the tablets with the enteric-coating is performed using a rotating pan coating apparatus (see Example 4). AMXT 1501 dicaprate tablets for use as pharmaceuticals are coated with Opadry™ hydroxy propylmethyl cellulose (HPMC, Colorcon) as described in Example 4 above.

In general, compressed tablets may be prepared by compressing with a suitable machine, known as a tablet press, after pre-mixing the formulation ingredients in a free-flowing form such as a powder or granules and mixed with fillers, binders, inert diluents, lubricating excipients together with disintegrants to aid dissolution of the tablets in the gastro-intestinal system of the treated subject. The resulting pressed tablets can undergo an additional enteric coating step to provide a pH-sensitive barrier and enables the coated tablet to stay intact until reaching the higher pH environment of the lower gastrointestinal tract.

Fillers in tablet pharmaceuticals are used to dilute the active agent and to enable precise control of the dose of active drug being administered. Common fillers or diluents in common use include lactose, mannitol, xylitol, dextrose, sucrose, sorbital, compressible sugar, microcrystalline cellulose (MCC), powdered cellulose, cornstarch, starch, pregelatinated starch, dextran, calcium carbonate, polyethylene glycol and hydroxypropyl methyl cellulose.

Disintegrants in tablet pharmaceuticals are used in modern pharmaceutical formulations to aid in the dissociation of excipients from the active drug in the gastrointestinal track of treated subjects. Examples of commonly used disintegrants include calcium carboxymethylcellulose, providone, crospovidone (polyvinylpolypyrrolidone), methyl cellulose, microcrystalline cellulose, croscarmellose sodium, hydroxypropyl cellulose, starch, pregelatinized starch and sodium alginate.

Lubricants in tablet pharmaceuticals are used to aid processing of powder pre-mixed for milling equipment including tablet presses. Examples of lubricants include calcium stearate, glyceryl monostearate, glyceryl palmitostearate, hydrogenated vegetable oil, light mineral oil, magnesium stearate, polyethylene glycol, sodium lauryl sulfate steric acid, and talc.

Glidants in tablet pharmaceutical preparations are used to improve flow of powders and aid in manufacturing using various processing equipment including tablet presses. Glidants in common use include silicon dioxide, talc cornstarch, and hydrophobic colloidal silica.

Although any methods and materials similar or equivalent to those described herein can also be used in the practice or testing of the present invention, a limited number of the exemplary methods and materials are described herein.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. The following patent documents are incorporated herein by reference, in their entireties: U.S. Pat. Nos. 7,662,999, 7,432,302, 7,411,002, 7,388,112, 7,208,528, 7,199,267, 7,160,923, 6,963,010, 6,914,079, 6,872,852, 6,646,149, 6,172,261 and RE43327, and US Pat. Publ. Nos. 2011/256161 and 2006/122279. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A salt of formula AMXT 1501:(caprate)$_2$, wherein AMXT 1501 has formula

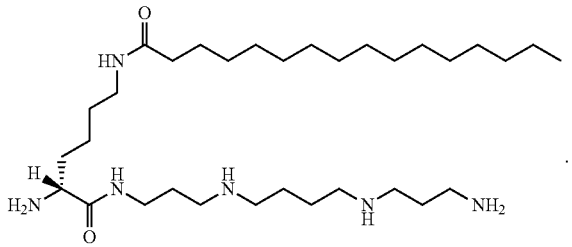

(AMXT 1501)

2. The salt of claim 1 having chemical structure (I)

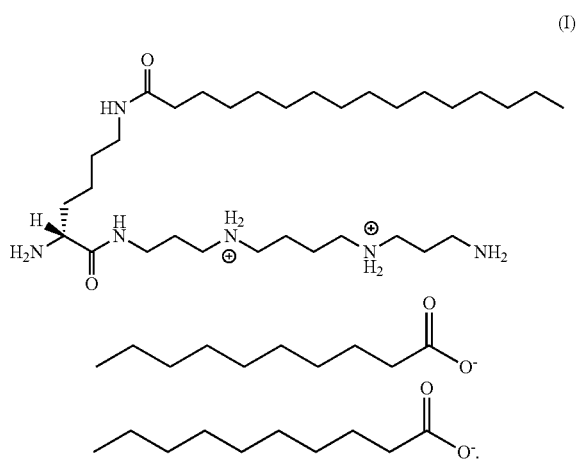

(I)

3. The salt of claim 1 which is not in admixture with more than 5 wt % of any other solid or liquid chemical.

4. A pharmaceutical composition comprising the salt of formula AMXT 1501:(caprate)$_2$ according to claim 1 and a pharmaceutically acceptable inert component.

5. The pharmaceutical composition of claim 4 in a solid oral dosage form.

6. The pharmaceutical composition of claim 5 wherein the solid dosage form is enterically coated.

7. A method of forming the salt of formula AMXT 1501:(caprate)$_2$ according to claim 1, the method comprising:

combining AMXT-1501, capric acid and a solvent so as to provide a solution; and isolating a solid residue from the solution, wherein the solid residue comprises AMXT 1501:(caprate)$_2$.

8. The method of claim 7 wherein the solvent comprises water, methanol or a combination thereof.

9. The method of claim 7 wherein 1.8-2.2 moles of capric acid are combined with each 1.0 mole of AMXT-1501.

10. The method of claim 7 wherein the solid residue is formed by precipitation from the solution.

11. A method of treating cancer comprising administering to a subject in need thereof a therapeutically effective amount of AMXT 1501:(caprate)$_2$ of claim 1.

12. The method of claim 11 wherein the therapeutically effective amount of AMXT 1501:(caprate)$_2$ is administered to the subject as a solid oral dosage form.

* * * * *